United States Patent
Sakakibara et al.

(10) Patent No.: US 9,520,569 B2
(45) Date of Patent: Dec. 13, 2016

(54) ARYL COMPOUNDS FOR APPLICATION IN A HIGHLY POLAR SOLVENT

(71) Applicant: Sumitomo Chemical Company, Limited, Tokyo (JP)

(72) Inventors: Ken Sakakibara, Ibaraki (JP); Masanobu Tanaka, Ibaraki (JP); Rui Ishikawa, Ibaraki (JP); Hideyuki Higashimura, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 219 days.

(21) Appl. No.: 14/351,317

(22) PCT Filed: Oct. 11, 2012

(86) PCT No.: PCT/JP2012/076307
§ 371 (c)(1),
(2) Date: Apr. 11, 2014

(87) PCT Pub. No.: WO2013/058160
PCT Pub. Date: Apr. 25, 2013

(65) Prior Publication Data
US 2014/0231717 A1 Aug. 21, 2014

(30) Foreign Application Priority Data

Oct. 17, 2011 (JP) ................. 2011-227669

(51) Int. Cl.
*H01B 1/00* (2006.01)
*H01L 51/00* (2006.01)
*C08G 61/00* (2006.01)
*H01B 1/12* (2006.01)
*C07C 229/64* (2006.01)
*C08G 61/12* (2006.01)
(Continued)

(52) U.S. Cl.
CPC ......... *H01L 51/0059* (2013.01); *C07C 229/64* (2013.01); *C08G 61/12* (2013.01); *C08L 65/00* (2013.01); *C09D 165/00* (2013.01); *H01B 1/12* (2013.01); *H01L 51/006* (2013.01); *H01L 51/0035* (2013.01); *H01L 51/0039* (2013.01); *H01L 51/0043* (2013.01); *H01L 51/0052* (2013.01); *H01L 51/0067* (2013.01); *H01L 51/0068* (2013.01); *C08G 2261/135* (2013.01); *C08G 2261/1412* (2013.01); *C08G 2261/1424* (2013.01); *C08G 2261/1426* (2013.01); *C08G 2261/3142* (2013.01); *C08G 2261/3162* (2013.01); *C08G 2261/411* (2013.01); *C08G 2261/5222* (2013.01); *C08G 2261/5242* (2013.01); *C08G 2261/76* (2013.01); *C08G 2261/91* (2013.01); *C08G 2261/95* (2013.01); *H01L 51/5012* (2013.01); *H01L 51/5056* (2013.01)

(58) Field of Classification Search
CPC ............. H01B 1/00; H01B 1/12; H01B 1/121; H01B 1/124; H01L 51/5012; C08G 61/12; C08G 63/685
See application file for complete search history.

(56) References Cited

U.S. PATENT DOCUMENTS 2,596,156 A    5/1952   Krimmel
6,169,163 B1   1/2001   Woo et al.
(Continued)

FOREIGN PATENT DOCUMENTS

CN    1555103 A    12/2004
CN    1827666 A    9/2006
(Continued)

OTHER PUBLICATIONS

Tipnis et al. "Printing efficient solar cells," SPIE Newsroom, Dec. 15, 2008.*
Int'l Search Report issued Jan. 8, 2013 in Int'l Application No. PCT/JP2012/076307.
Yan et al, "High-Performance Hole-Transport Layers for Polymer Light-Emitting Diodes. Implementation of Organosiloxane Cross-Linking Chemistry in Polymeric Electroluminescent Devices," Journal of the American Chemical Society, vol. 127, pp. 3172-3183 (2005).
Office Action issued Nov. 25, 2014 in JP Application No. 2013-539617.

*Primary Examiner* — Mark Kopec
(74) *Attorney, Agent, or Firm* — Panitch Schwarze Belisario & Nadel LLP

(57) ABSTRACT

The present invention provides a compound that has high solubility in a highly polar solvent and is usefully usable for an application method using a highly polar solvent, the compound that can manufacture an electroluminescent device having high light-emitting efficiency. Specifically, the present invention provides a compound containing a structure represented by Formula (1):

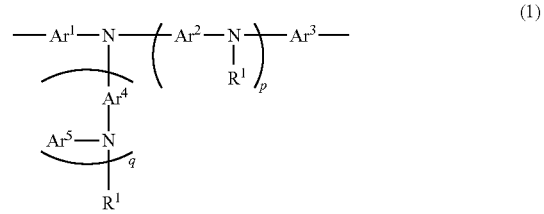

(1)

wherein:
Ar$^1$, Ar$^2$, Ar$^3$, and Ar$^4$ each independently represent a divalent aromatic group optionally having substituent(s);
Ar$^5$ represents a monovalent aromatic group optionally having substituent(s);
p and q each independently represent an integer of 0 or more; and
R$^1$ represents a given monovalent group.

17 Claims, No Drawings

(51) Int. Cl.
*C09D 165/00* (2006.01)
*C08L 65/00* (2006.01)
*H01L 51/50* (2006.01)

(56) References Cited

U.S. PATENT DOCUMENTS

| | | |
|---|---|---|
| 6,861,502 B1 | 3/2005 | Towns et al. |
| 2003/0153725 A1 | 8/2003 | Towns et al. |
| 2009/0123860 A1 | 5/2009 | Lincoln et al. |
| 2011/0006294 A1 | 1/2011 | Tanaka et al. |
| 2012/0181529 A1 | 7/2012 | Tanaka et al. |

FOREIGN PATENT DOCUMENTS

| | | |
|---|---|---|
| JP | H05-21165 A | 1/1993 |
| JP | H10-338658 A | 12/1998 |
| JP | 2002-539292 A | 11/2002 |
| JP | 2005-213199 A | 8/2005 |
| JP | 2009-239279 A | 10/2009 |
| WO | 02051958 A1 | 7/2002 |
| WO | 2006040530 A1 | 4/2006 |
| WO | 2011040388 A1 | 4/2011 |

* cited by examiner

ARYL COMPOUNDS FOR APPLICATION IN A HIGHLY POLAR SOLVENT

CROSS-REFERENCE TO RELATED APPLICATION

This application is a Section 371 of International Application No. PCT/JP2012/076307, filed Oct. 11, 2012, which was published in the Japanese language on Apr. 25, 2013, under International Publication No. WO 2013/058160 A1, and the disclosure of which is incorporated herein by reference.

TECHNICAL FIELD

The present invention relates to a compound and the like.

BACKGROUND ART

Non Patent Literature 1 discloses that a compound represented by the following formula having a triarylamine structure is used for the manufacture of an electroluminescent device. However, since the compound represented by the following formula has an extremely poor solubility in a highly polar solvent, it has been difficult to adopt the compound to an application method using a highly polar solvent (for example, a method for manufacturing a stacked structure by applying a solution containing the compound represented by the following formula and a highly polar solvent onto a layer formed of a compound which is insoluble in the highly polar solvent).

[Chemical Formula 1]

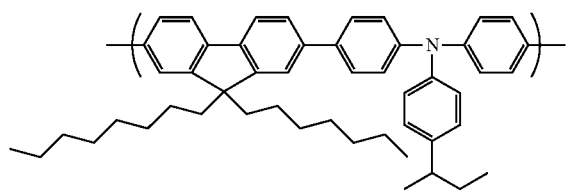

CITATION LIST

Non Patent Literature

Non Patent Literature 1: Journal of the American Chemical Society, 2005, 127, 3172-3183

SUMMARY OF THE INVENTION

Technical Problem

Therefore, an object of the present invention is to provide a compound that has high solubility in a highly polar solvent, that is usefully usable for an application method using a highly polar solvent, and that can be used to manufacture an electroluminescent device having high light-emitting efficiency.

Solution to Problem

In a first aspect, the present invention provides a compound comprising a structure represented by Formula (1).

A compound comprising a structure represented by Formula (1):

[Chemical Formula 2]

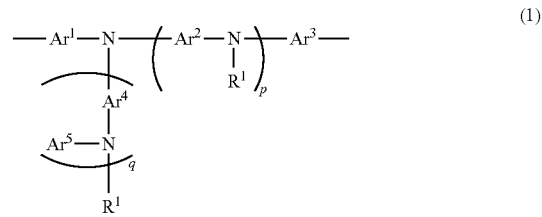

[in the formula:
$Ar^1$, $Ar^2$, $Ar^3$, and $Ar^4$ each independently represent a divalent aromatic group optionally having substituent(s) and may be bonded to each other to form a ring, when more than one $Ar^2$ is present, such $Ar^2$s may be the same as or different from each other, and when more than one $Ar^4$ is present, such $Ar^4$s may be the same as or different from each other;

$Ar^5$ represents a monovalent aromatic group optionally having substituent(s), and when more than one $Ar^5$ is present, such $Ar^5$s may be the same as or different from each other;

p and q each independently represent an integer of 0 or more; and $R^1$ represents a monovalent group represented by Formula (2), and when more than one $R^1$ is present, such $R^1$s may be the same as or different from each other:

[Chemical Formula 3]

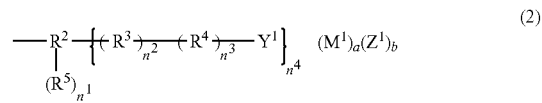

[in the formula:
$R^2$ represents a $(1+n^1+n^4)$-valent aromatic group optionally having substituent(s);

$R^3$ represents a divalent organic group optionally having substituent(s);

$R^4$ represents a divalent organic group comprising a structure which is capable of interacting with a cation through chelation, and when more than one $R^4$ is present, such $R^4$s may be bonded to each other to form a ring;

$R^5$ represents a monovalent organic group comprising a structure which is capable of interacting with a cation through chelation, and when more than one $R^5$ is present, such $R^5$s may be bonded to each other to form a ring;

$Y^1$ represents a monovalent group comprising an anion;

$n^1$ represents an integer of 0 or more, $n^2$ represents 0 or 1, $n^3$ represents an integer of 0 or more, $n^4$ represents an integer of 1 or more, and $n^1+n^3 \geq 1$ is satisfied, when more than one $R^3$ is present, such $R^3$s may be the same as or different from each other, when more than one $R^4$ is present, such $R^4$s may be the same as or different from each other, when more than one $R^5$ is present, such $R^5$s may be the same as or different from each other, and when more than one $Y^1$ is present, such $Y^1$s may be the same as or different from each other;

$M^1$ represents a cation;

$Z^1$ represents an anion;

a represents an integer of 1 or more, and b represents an integer of 0 or more, provided that a and b are selected so that electric charge of the structure represented by Formula (1) becomes zero; and when more than one $M^1$ is present, such $M^1$s may be the same as or different from each other, and when more than one $Z^1$ is present, such $Z^1$s may be the same as or different from each other.]]

In a second aspect, the present invention provides a polymer compound comprising the structure represented by Formula (1) as a constitutional unit.

In a third aspect, the present invention provides a low molecular compound comprising the structure represented by Formula (1) as a constitutional unit.

In a fourth aspect, the present invention provides a composition comprising the compound represented by Formula (1) and at least one material selected from the group consisting of a hole transport material, an electron transport material, and a light-emitting material.

In a fifth aspect, the present invention provides a stacked structure, an electroluminescent device, and a photoelectric conversion device, which comprise the compound comprising the structure represented by Formula (1) or the above composition.

In a sixth aspect, the present invention provides a compound comprising a structure represented by Formula (5) described below.

In a seventh aspect, the present invention provides a compound comprising a structure represented by Formula (7) described below.

Advantageous Effects of Invention

The present invention can provide a compound that has high solubility in a highly polar solvent and is usefully usable for an application method using a highly polar solvent, the compound capable of manufacturing an electroluminescent device having high light-emitting efficiency. The present invention can also provide an electroluminescent device and a photoelectric conversion device using a stacked structure comprising the compound.

DESCRIPTION OF EMBODIMENTS

In this specification, the "highly polar solvent" means a solvent having a solubility parameter of 9.3 or more. For example, values that can be used as the solubility parameter are described in "Solvent Handbook" by Teruzo Asahara (14th edition, Kodansha, published in 1996). Examples of the solvent (values in parentheses represent the values of solubility parameters of the respective solvents) include water (21), methanol (12.9), ethanol (11.2), 2-propanol (11.5), 1-butanol (9.9), tert-butyl alcohol (10.5), acetonitrile (11.8), 1,2-ethanediol (14.7), N,N-dimethylformamide (11.5), dimethylsulfoxide (12.8), acetic acid (12.4), nitrobenzene (11.1), nitromethane (11.0), 1,2-dichloroethane (9.7), dichloromethane (9.6), chlorobenzene (9.6), bromobenzene (9.9), dioxane (9.8), propylene carbonate (13.3), pyridine (10.4), carbon disulfide (10.0), solvent mixtures of these solvents, and the like. A solubility parameter ($\delta_m$) for a mixed solvent of a solvent 1 and a solvent 2 can be determined by "$\delta_m = \delta_1 \times \phi_1 + \delta_2 \times \phi_2$" ($\delta_1$ means the solubility parameter of the solvent 1; $\phi_1$ means the volume fraction of the solvent 1; $\delta_2$ means the solubility parameter of the solvent 2; and $\phi_2$ means the volume fraction of the solvent 2).

From the point of view that a stacked structure is manufactured by applying a solution comprising the compound of the present invention and the highly polar solvent onto a layer formed of a compound which is insoluble in the highly polar solvent, the highly polar solvent is preferably water, methanol, ethanol, 2-propanol, acetonitrile, 1,2-ethanediol, N,N-dimethylformamide, or dimethylsulfoxide, more preferably methanol, ethanol, acetonitrile, N,N-dimethylformamide, or dimethylsulfoxide, and particularly preferably methanol or N,N-dimethylformamide.

In this specification, "optionally having substituent(s)" includes both a case in which a hydrogen atom constituting a group written immediately after the term is unsubstituted and a case in which a part of or all of hydrogen atoms is/are substituted with substituent(s). Examples of the substituent include a hydroxy group, a nitro group, a fluorine atom, a hydrocarbyl group having 1 to 60 carbon atoms, a hydrocarbyloxy group having 1 to 60 carbon atoms, a hydrocarbylamino group having 1 to 60 carbon atoms, a cross-linking group, and the like. Among these substituents, since the compound of the present invention can be easily synthesized, the substituent is preferably a hydrocarbyl group having 1 to 18 carbon atoms, a hydrocarbyloxy group having 1 to 18 carbon atoms, or a cross-linking group, more preferably a hydrocarbyl group having 1 to 12 carbon atoms or a hydrocarbyloxy group having 1 to 12 carbon atoms, and further preferably a hydrocarbyl group having 1 to 8 carbon atoms or a hydrocarbyloxy group having 1 to 8 carbon atoms.

The hydrocarbyl group may be any of linear, branched, and cyclic.

Examples of the hydrocarbyl group include a methyl group, an ethyl group, a 1-propyl group, a 2-propyl group, a 1-butyl group, a 2-butyl group, an isobutyl group, a tert-butyl group, a pentyl group, a hexyl group, an octyl group, a decyl group, a dodecyl group, a 2-ethylhexyl group, a 3,7-dimethyloctyl group, a cyclopropyl group, a cyclopentyl group, a cyclohexyl group, a 1-adamantyl group, a 2-adamantyl group, a norbornyl group, a benzyl group, an α,α-dimethylbenzyl group, a 1-phenethyl group, a 2-phenethyl group, a vinyl group, a propenyl group, a butenyl group, an oleyl group, an eicosapentaenyl group, a docosahexaenyl group, a 2,2-diphenylvinyl group, a 1,2,2-triphenylvinyl group, a 2-phenyl-2-propenyl group, a phenyl group, a 2-tolyl group, a 4-tolyl group, a 4-trifluoromethylphenyl group, a 4-methoxyphenyl group, a 4-cyanophenyl group, a 2-biphenylyl group, a 3-biphenylyl group, a 4-biphenylyl group, a terphenylyl group, a 3,5-diphenylphenyl group, a 3,4-diphenylphenyl group, a pentaphenylphenyl group, a 4-(2,2-diphenylvinyl)phenyl group, a 4-(1,2,2-triphenylvinyl)phenyl group, a fluorenyl group, a 1-naphthyl group, a 2-naphthyl group, a 9-anthryl group, a 2-anthryl group, a 9-phenanthryl group, a 1-pyrenyl group, a chrysenyl group, a tetracenyl group, and a coronyl group.

Since the compound of the present invention can be easily synthesized, the hydrocarbyl group is:

preferably a methyl group, an ethyl group, a 1-propyl group, a 2-propyl group, a 1-butyl group, a 2-butyl group, an isobutyl group, a tert-butyl group, a pentyl group, a hexyl group, an octyl group, a decyl group, a dodecyl group, a 2-ethylhexyl group, a 3,7-dimethyloctyl group, a benzyl group, an α,α-dimethylbenzyl group, a 1-phenethyl group, a 2-phenethyl group, a vinyl group, a propenyl group, a butenyl group, an oleyl group, an eicosapentaenyl group, a docosahexaenyl group, a 2,2-diphenylvinyl group, a 1,2,2-triphenylvinyl group, a 2-phenyl-2-propenyl group, a phenyl group, a 2-tolyl group, a 4-tolyl group, a 4-trifluoromethylphenyl group, a 4-methoxyphenyl group, a 4-cyanophenyl group, a 2-biphenylyl group, a 3-biphenylyl group, a 4-biphenylyl group, a terphenylyl group, a 3,5-diphenylphenyl group, a 3,4-diphenylphenyl group, a pentaphenylphenyl group, a 4-(2,2-diphenylvinyl)phenyl group, a 4-(1,2,2-triphenylvinyl)phenyl group, a fluorenyl group, a 1-naphthyl group, a 2-naphthyl group, a 9-anthryl group, a 2-anthryl group, or a 9-phenanthryl group, more preferably a methyl group, an ethyl group, a 1-propyl group, a 2-propyl group, a 1-butyl group, a 2-butyl group, an isobutyl group, a tert-butyl group, a pentyl group, a hexyl group, an octyl group, 2-ethylhexyl group, a 3,7-dimethyloctyl group, a benzyl group, or a phenyl group, and further preferably a methyl group, an ethyl group, a 1-propyl group, a 2-propyl group, a 1-butyl group, a 2-butyl group, an isobutyl group, a tert-butyl group, a pentyl group, a hexyl group, or an octyl group.

The hydrocarbyloxy group may be any of linear, branched, and cyclic.

Examples of the hydrocarbyloxy group include a methoxy group, an ethoxy group, a 1-propanoxy group, a 2-propanoxy group, a 1-butoxy group, a 2-butoxy group, an isobutoxy group, a tert-butoxy group, a pentyloxy group, a hexyloxy group, an octyloxy group, a decyloxy group, a dodecyloxy group, a 2-ethylhexyloxy group, a 3,7-dimethyloctyloxy group, a cyclopropanoxy group, a cyclopentyloxy group, a cyclohexyloxy group, a 1-adamantyloxy group, a 2-adamantyloxy group, a norbornyloxy group, a trifluoromethoxy group, a benzyloxy group, an α,α-dimethylbenzyloxy group, a 2-phenethyloxy group, a 1-phenethyloxy group, a phenoxy group, an alkoxyphenoxy group, an alkylphenoxy group, a 1-naphthyloxy group, a 2-naphthyloxy group, and a pentafluorophenyloxy group.

Since the compound of the present invention can be easily synthesized, the hydrocarbyloxy group is:

preferably a methoxy group, an ethoxy group, a 1-propanoxy group, a 2-propanoxy group, a 1-butoxy group, a 2-butoxy group, an isobutoxy group, a tert-butoxy group, a pentyloxy group, a hexyloxy group, an octyloxy group, a decyloxy group, a dodecyloxy group, a 2-ethylhexyloxy group, or a 3,7-dimethyloctyloxy group, and more preferably a methoxy group, an ethoxy group, a 1-propanoxy group, a 2-propanoxy group, a 1-butoxy group, a 2-butoxy group, an isobutoxy group, a tert-butoxy group, a pentyloxy group, a hexyloxy group, or an octyloxy group.

The hydrocarbylamino group may be any of linear, branched, and cyclic.

Examples of the hydrocarbylamino group include a methylamino group, an ethylamino group, a 1-propylamino group, a 2-propylamino group, a 1-butylamino group, a 2-butylamino group, an isobutylamino group, a tert-butylamino group, a pentylamino group, a hexylamino group, an octylamino group, a decylamino group, a dodecylamino group, a 2-ethylhexylamino group, a 3,7-dimethyloctylamino group, a cyclopropylamino group, a cyclopentylamino group, a cyclohexylamino group, a 1-adamantylamino group, a 2-adamantylamino group, a norbornylamino group, a trifluoromethylamino group, a benzylamino group, an α,α-dimethylbenzylamino group, a 2-phenethylamino group, a 1-phenethylamino group, a phenylamino group, an alkoxyphenylamino group, an alkylphenylamino group, a 1-naphthylamino group, a 2-naphthylamino group, and a pentafluorophenylamino group.

Since the compound of the present invention can be easily synthesized, the hydrocarbylamino group is:

preferably a methylamino group, an ethylamino group, a 1-propylamino group, a 2-propylamino group, a 1-butylamino group, a 2-butylamino group, an isobutylamino group, a tert-butylamino group, a pentylamino group, a hexylamino group, or an octylamino group, and more preferably a methylamino group, an ethylamino group, a 1-propylamino group, a 2-propylamino group, a 1-butylamino group, or a 2-butylamino group.

The above mentioned cross-linking group represents a substituent that can form bond(s) among two or more molecules by developing a polymerization reaction through the effect of heat, light, a thermal polymerization initiator, or a photopolymerization initiator.

Examples of the cross-linking group include a vinyl group, an ethynyl group, a butenyl group, an acryloyl group, an acrylate group, an acrylamidyl group, a methacryl group, a methacrylate group, a methacrylamido group, an ethenyloxy group, an ethenylamino group, a hydroxysilyl group, a functional group having a structure of a small ring (e.g., a cyclopropane, cyclobutane, benzocyclobutene, epoxide, oxetane, diketene, thiirane, lactone, lactam, or the like), and a functional group having a structure of a siloxane derivative.

In addition to the above cross-linking group, a combination of groups that can form an ester bond or an amido bond may be used. Examples of the combination of groups that can form an ester bond or an amido bond include a combination of an ester group and an amino group and a combination of an ester group and a hydroxy group.

In this specification, the "aromatic group" represents an atomic group remaining after removing one or more hydrogen atoms bonded to a ring of an aromatic hydrocarbon, an atomic group remaining after removing one or more hydrogen atoms bonded to a ring of an aromatic heterocyclic compound, and an atomic group remaining after removing one or more hydrogen atoms bonded to a ring of a compound in which two or more compounds selected from aromatic hydrocarbons and aromatic heterocyclic compounds are bonded directly or through —NH—, —O—, or —S—.

In this specification, the "organic group" represents a group comprising a carbon atom and a hydrogen atom, and examples of the organic group include the above hydrocarbyl group having 1 to 60 carbon atoms, hydrocarbyloxy group having 1 to 60 carbon atoms, and hydrocarbylamino group having 1 to 60 carbon atoms.

In this specification, the "structure that can interact with a cation through chelation" means a structure in which two or more atoms (which may be one kind of atom or two or more kinds of atoms) selected from an oxygen atom, a nitrogen atom, a phosphorus atom, and a sulfur atom can form a coordination bond or an electrostatic interaction with a cation optionally having substituent(s). Examples of the cation include a metal cation, an ammonium cation, a phosphonium cation, a sulfonium cation, a sulfoxonium cation, and an iodonium cation.

In this specification, the "constitutional unit" means one or more units present in a polymer compound and is preferably present in the polymer compound as a "repeating unit" (i.e., two or more units present in the polymer compound).

In this specification, the "low molecular compound" means a compound whose molecular weight is less than 2,000, and the "polymer compound" means a compound whose molecular weight is 2,000 or more. When a compound is polydispersed, the molecular weight means a weight average molecular weight calculated by polystyrene conversion using gel permeation chromatography (GPC).

The "first compound" of the present invention is a compound comprising the structure represented by Formula (1).

The compound includes both a polymer compound comprising the structure represented by Formula (1) as a constitutional unit and a low molecular compound comprising the structure represented by Formula (1). A compound comprising structures represented by Formula (3) and Formula (4) described below is included in the form of the compound comprising the structure represented by Formula (1).

The "second compound" of the present invention is a compound of a structure represented by Formula (5) described below. The compound includes both a polymer compound comprising the structure represented by Formula (5) as a constitutional unit and a low molecular compound comprising the structure represented by Formula (5).

The "third compound" of the present invention is a compound comprising a structure represented by Formula (7) described below.

<First Compound>

The first compound of the present invention comprises the structure of Formula (1). The structure of Formula (1) represents a divalent structure. Description of Formula (1) is as follows.

[Chemical Formula 4]

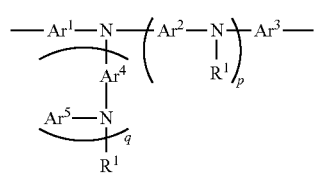

(1)

The above $Ar^1$, $Ar^2$, $Ar^3$, and $Ar^4$ are each independently a divalent aromatic group optionally having substituent(s) and may be bonded to each other to form a ring. When more than one $Ar^2$ is present, they may be the same as or different from each other. When more than one $Ar^4$ is present, they may be the same as or different from each other.

When not forming a ring, $Ar^1$, $Ar^2$, $Ar^3$, and $Ar^4$ are preferably an atomic group remaining after removing two hydrogen atoms bonded to a ring of a molecule represented by any one of Formulae 1-1 to 1-47.

Among these, since the light-emitting efficiency of an electroluminescent device using the compound of the present invention is higher, $Ar^1$ and $Ar^2$ are more preferably an atomic group remaining after removing two hydrogen atoms bonded to a ring of a molecule selected from the group consisting of molecules represented by Formulae 1-1, 1-2, 1-10, 1-12, 1-16, 1-20, 1-22, 1-23, 1-26, 1-27, 1-28, 1-35, 1-42, 1-43, 1-44, 1-45, and 1-46, further preferably an atomic group remaining after removing two hydrogen atoms bonded to a ring of a molecule selected from the group consisting of molecules represented by Formulae 1-1, 1-10, 1-22, 1-23, 1-26, 1-27, 1-28, 1-35, and 1-44, and particularly preferably an atomic group remaining after removing two hydrogen atoms bonded to a ring of a molecule represented by Formulae 1-1 or 1-10.

[Chemical Formula 5]

1-1

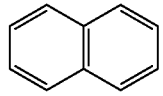

1-2

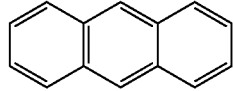

1-3

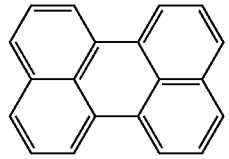

1-4

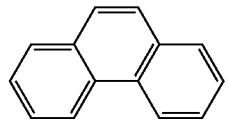

1-5

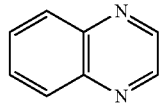

1-6

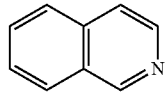

1-7

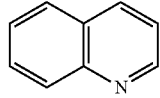

1-8

1-9

1-10

1-11

1-12

1-13

1-14

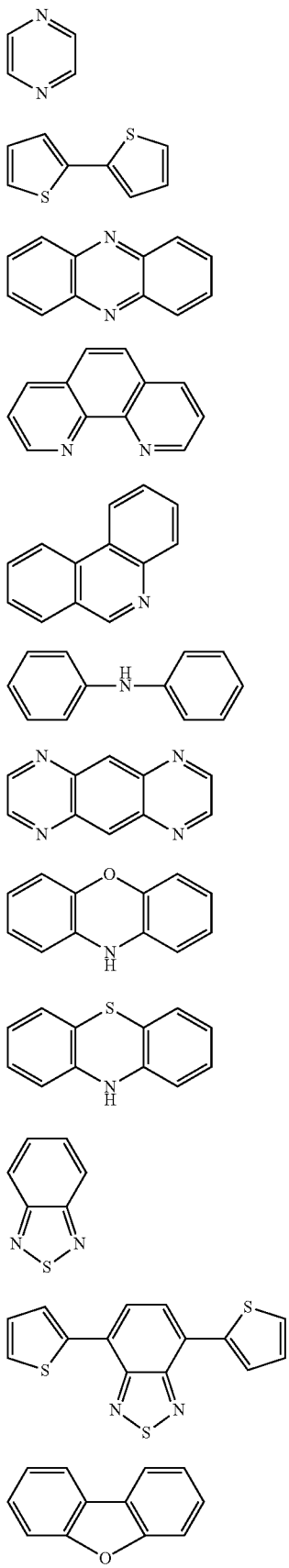
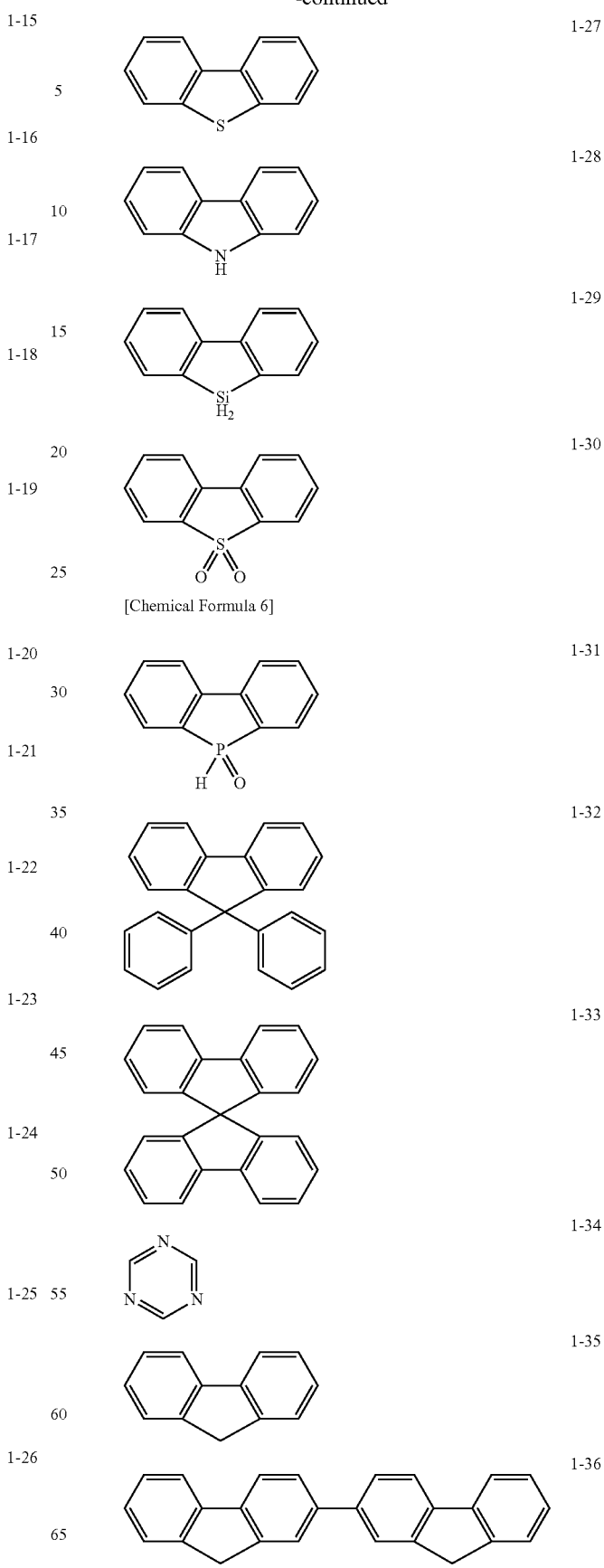

1-37
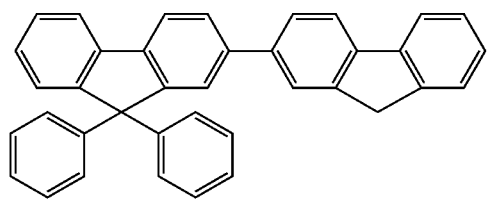

1-38
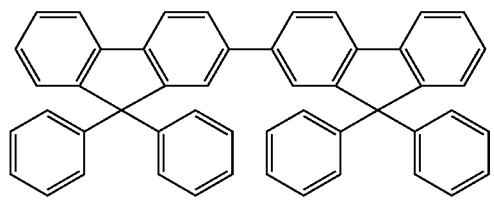

1-39
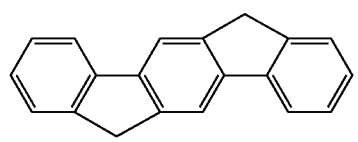

1-40
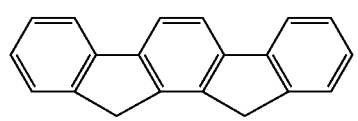

1-41
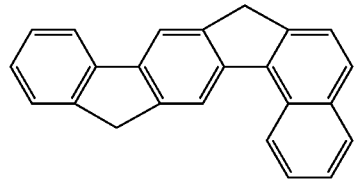

1-42
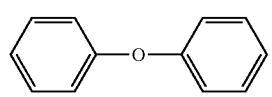

1-43
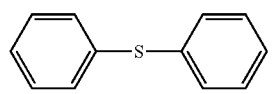

1-44
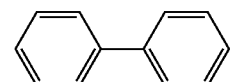

1-45
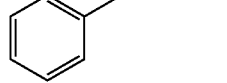

1-46
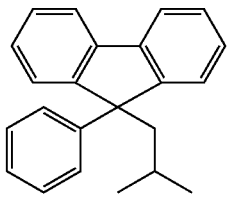

1-47
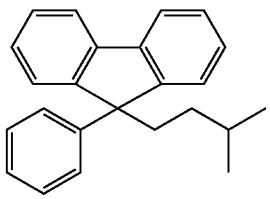

When forming a ring, for example, $Ar^1$ and $Ar^2$, $Ar^1$ and $Ar^3$, $Ar^1$ and $Ar^4$, $Ar^2$ and $Ar^3$, $Ar^2$ and $Ar^4$, and $Ar^3$ and $Ar^4$ may be bonded to each other to form a ring, and it is preferable that $Ar^1$ and $Ar^2$, $Ar^1$ and $Ar^3$, and $Ar^2$ and $Ar^3$ are bonded to each other to form a ring.

Since the light-emitting efficiency of an electroluminescent device using the compound of the present invention is higher, when forming a ring, $Ar^1$, $Ar^2$, $Ar^3$, and $Ar^4$ are preferably an atomic group remaining after removing two hydrogen atoms bonded to a ring of a molecule represented by any one of Formulae 1-1 to 1-15, more preferably an atomic group remaining after removing two hydrogen atoms bonded to a ring of a molecule represented by any one of Formulae 1-1, 1-2, and 1-6 to 1-15, and further preferably an atomic group remaining after removing two hydrogen atoms bonded to a ring of a molecule represented by any one of Formulae 1-1, 1-2, and 1-10.

The above $Ar^5$ is a monovalent aromatic group optionally having substituent(s), and when more than one $Ar^5$ is present, they may be the same as or different from each other.

The above $Ar^5$ is preferably an atomic group remaining after removing one hydrogen atom bonded to a ring of a molecule represented by any one of Formulae 1-1 to 1-47. Among these, since the light-emitting efficiency of an electroluminescent device using the compound of the present invention is higher, $Ar^5$ is more preferably an atomic group remaining after removing one hydrogen atom bonded to a ring of a molecule represented by any one of Formulae 1-1, 1-2, 1-10, 1-12, 1-16, 1-20, 1-22, 1-23, 1-26, 1-27, 1-28, 1-35, 1-42, 1-43, 1-44, 1-45, and 1-46, further preferably an atomic group remaining after removing one hydrogen atom bonded to a ring of a molecule represented by any one of Formulae 1-1, 1-10, 1-22, 1-23, 1-26, 1-27, 1-28, 1-35, and 1-44, and particularly preferably an atomic group remaining after removing one hydrogen atom bonded to a ring of a molecular represented by Formulae 1-1 or 1-10.

The above p and q each independently represent an integer of 0 or more.

The above p is preferably 0 to 4, more preferably 0 to 2, and further preferably 0 or 1. This is because the light-emitting efficiency of an electroluminescent device using the compound of the present invention is higher.

The above q is preferably 0 to 4, more preferably 0 to 2, and further preferably 0 or 1. This is because the light-emitting efficiency of an electroluminescent device using the compound of the present invention is higher.

The above $R^1$ represents a monovalent group represented by Formula (2), and when more than one $R^1$ is present, they may be the same as or different from each other.

The above $R^2$ is a $(1+n^1+n^4)$-valent aromatic group optionally having substituent(s).

The above $R^2$ is preferably an atomic group remaining after removing $(1+n^1+n^4)$ hydrogen atoms bonded to a ring of a molecule represented by any one of Formulae 1-1 to 1-47. Among these, since the light-emitting efficiency of an electroluminescent device using the compound of the present invention is higher, $R^2$ is more preferably an atomic group remaining after removing $(1+n^1+n^4)$ hydrogen atoms bonded to a ring of a molecule represented by any one of Formulae 1-1, 1-2, 1-10, 1-12, 1-16, 1-20, 1-22, 1-23, 1-26, 1-27, 1-28, 1-35, 1-42, 1-43, 1-44, 1-45, and 1-46, further preferably an atomic group remaining after removing $(1+n^1+n^4)$ hydrogen atoms bonded to a ring of a molecule represented by any one of Formulae 1-1, 1-10, 1-22, 1-23, 1-26, 1-27, 1-28, 1-35, and 1-44, and particularly preferably an atomic group remaining after removing $(1+n^1+n^4)$ hydrogen atoms bonded to a ring of a molecular represented by Formulae 1-1 or 1-10.

The above $R^3$ represents a divalent organic group optionally having substituent(s), and when more than one $R^3$ is present, they may be the same as or different from each other.

Examples of $R^3$ include a hydrocarbylene group optionally having substituent(s), and the number of carbon atoms is preferably in a range of 1 to 60 (the number of carbon atoms does not include the number of carbon atoms of the substituent(s)). The hydrocarbylene group may be any of linear, branched, and cyclic.

In view of the convenience of the synthesis of the compound of the present invention, $R^3$ is:

preferably a methylene group, an ethylene group, a propylene group, a butylene group, a pentylene group, a hexylene group, an octylene group, a decylene group, a dodecylene group, a 2-ethylhexylene group, a 3,7-dimethyloctylene group, a cyclopropylene group, a cyclopentylene group, a cyclohexylene group, an α,α-dimethylenebenzyl group, a 1-phenethylene group, a 2-phenethylene group, a vinylene group, a propenylene group, a butenylene group, an oleylene group, a phenylene group, a tolylene group, a biphenylene group, a terphenylene group, a 3,5-diphenylphenylene group, a 4-(1,2,2-triphenylvinyl) phenylene group, a naphthylene group, an anthrylene group, or a phenanthrylene group, more preferably a methylene group, an ethylene group, a propylene group, a butylene group, a pentylene group, a hexylene group, an octylene group, a decylene group, a dodecylene group, a 2-ethylhexylene group, a 3,7-dimethyloctylene group, a vinylene group, a propenylene group, a butenylene group, a phenylene group, a tolylene group, or a biphenylene group, further preferably a methylene group, an ethylene group, a propylene group, a butylene group, a hexylene group, an octylene group, a vinylene group, or a phenylene group, and particularly preferably an ethylene group, a propylene group, a butylene group, or a phenylene group.

The above $R^4$ represents a divalent organic group comprising a structure that can interact with a cation through chelation, and when more than one $R^4$ is present, they may be bonded to each other to form a ring. When more than one $R^4$ is present, they may be the same as or different from each other.

The $R^4$ preferably comprises a structure represented by Formula (8). The structure represented by Formula (8) represents a divalent structure.

[Chemical Formula 7]

$$\{E-A\}_{n^{11}} \qquad (8)$$

[In the formula,

E represents a divalent organic group;

A represents an oxygen atom, a nitrogen atom, a phosphorus atom, or a sulfur atom;

$n^{11}$ represents an integer of 1 or more; and when more than one E is present, they may be the same as or different from each other, and when more than one A is present, they may be the same as or different from each other.]

Examples of E include a hydrocarbylene group optionally having substituent(s), whose number of carbon atoms is preferably in a range of 1 to 60 (the number of carbon atoms does not include the number of carbon atoms of the substituent(s)). The hydrocarbylene group may be any of linear, branched, and cyclic.

In view of the convenience of the synthesis of the compound of the present invention, E is:

preferably a methylene group, an ethylene group, a propylene group, a butylene group, a pentylene group, a hexylene group, an octylene group, a decylene group, a dodecylene group, a 2-ethylhexylene group, a 3,7-dimethyloctylene group, a cyclopropylene group, a cyclopentylene group, a cyclohexylene group, an α,α-dimethylenebenzyl group, a 1-phenethylene group, a 2-phenethylene group, a vinylene group, a propenylene group, a butenylene group, an oleylene group, a phenylene group, a tolylene group, a biphenylene group, a terphenylene group, a 3,5-dimethylphenylene group, a 4-(1,2,2-triphenylvinyl) phenylene group, a naphthylene group, an anthrylene group, or a phenanthrylene group, more preferably a methylene group, an ethylene group, a propylene group, a butylene group, a pentylene group, a hexylene group, an octylene group, a decylene group, a dodecylene group, a 2-ethylhexylene group, a 3,7-dimethyloctylene group, a vinylene group, a propenylene group, a butenylene group, a phenylene group, a tolylene group, or a biphenylene group, further preferably a methylene group, an ethylene group, a propylene group, a butylene group, a hexylene group, an octylene group, a vinylene group, or a phenylene group, and particularly preferably an ethylene group, a propylene group, or a butylene group.

The above A is an oxygen atom, a nitrogen atom, a phosphorus atom, or a sulfur atom. In view of the stability (in particular, stability in the atmosphere) of the compound of the present invention, A is preferably an oxygen atom or a nitrogen atom and more preferably an oxygen atom.

The above $n^{11}$ represents an integer of 1 or more. In view of the synthesis of the compound of the present invention, $n^{11}$ is preferably 2 to 8, more preferably 2 to 6, further preferably 2 to 4, and particularly preferably 3 or 4.

In view of the synthesis and stability (in particular, stability in the atmosphere) of the compound of the present invention, $R^4$ is preferably a divalent organic group having two or more oxygen atoms. Examples of $R^4$ include an organic group remaining after removing two hydrogen atoms from a compound represented by any one of Formulae 2-1 to 2-27. Among these, in view of the synthesis of the compound of the present invention, the $R^4$ is more preferably an organic group remaining after removing two hydrogen atoms from a compound represented by any one of Formulae 2-1 to 2-8, further preferably an organic group remaining after removing two hydrogen atoms from a compound represented by any one of Formulae 2-1 to 2-4 and 2-6, and particularly preferably an organic group remaining after removing two hydrogen atoms from a compound represented by Formulae 2-3 or 2-4. The organic group remaining after removing two hydrogen atoms from a compound represented by any one of Formulae 2-1 to 2-27 optionally has substituent(s).

[Chemical Formula 8]

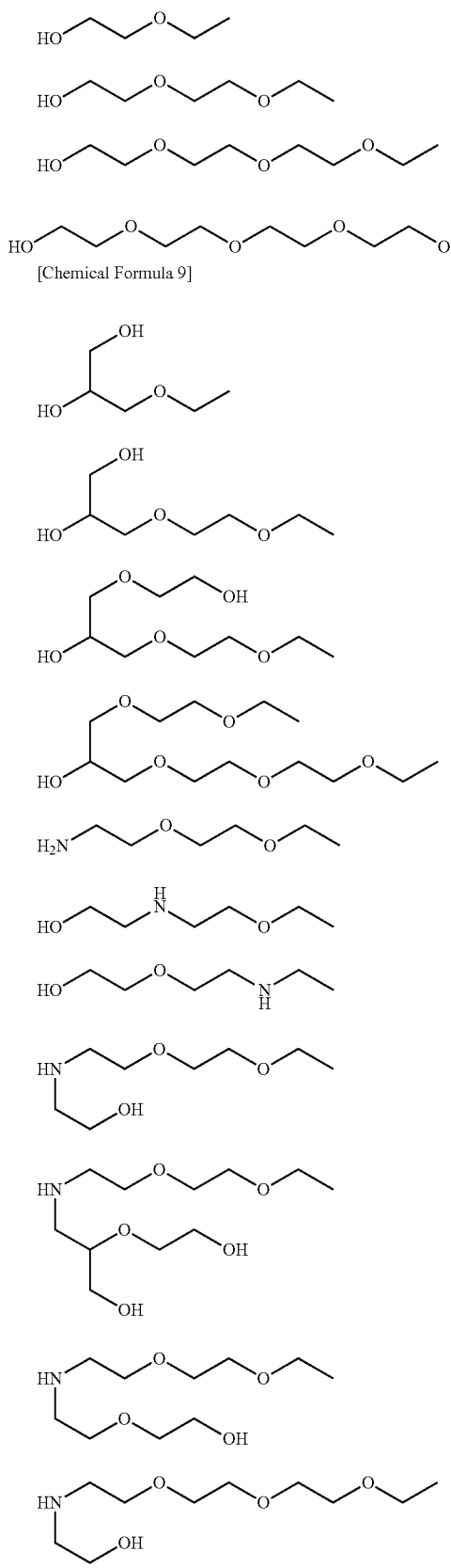

[Chemical Formula 9]

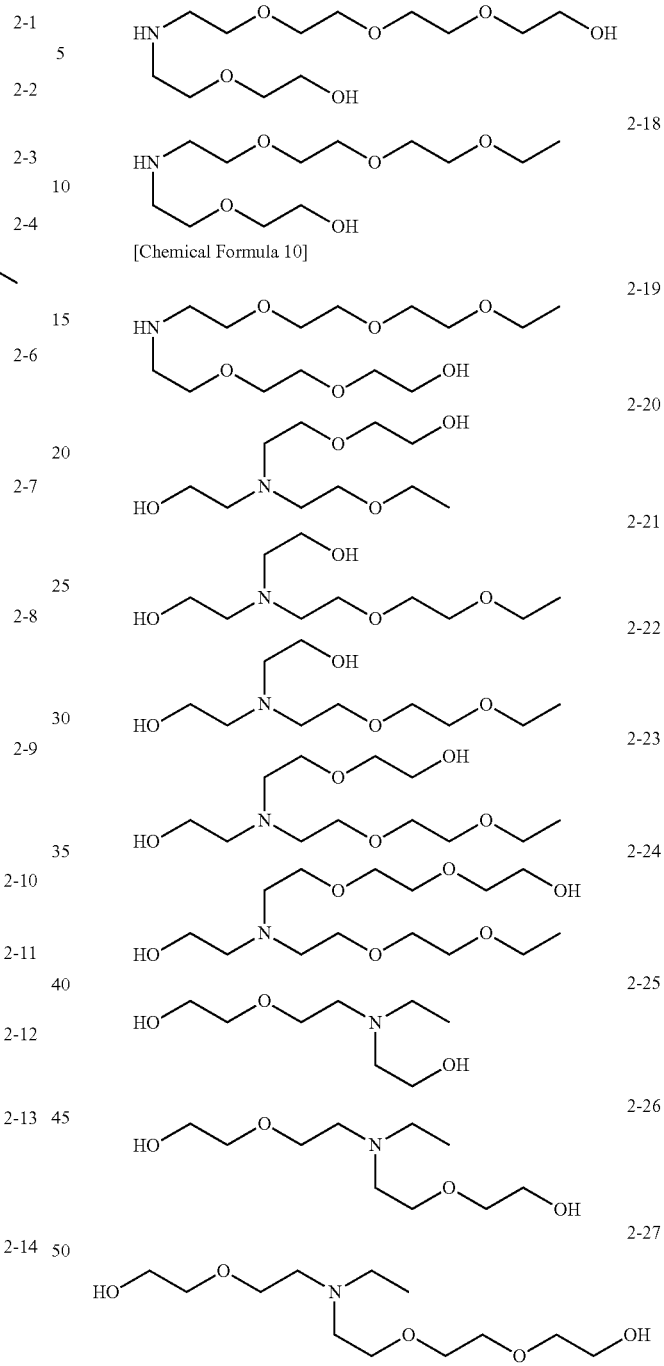

[Chemical Formula 10]

The above $R^5$ represents a divalent organic group comprising a structure that can interact with a cation through chelation, and when more than one $R^5$ is present, they may be bonded to each other to form a ring. When more than one $R^5$ is present, they may be the same as or different from each other.

The above $R^5$ is preferably a structure represented by Formula (8').

[Chemical Formula 11]

$$\mathrm{+E'\text{-}A'\text{)}_{n}\text{''}B'} \tag{8'}$$

[In the formula,

E' represents a divalent organic group;

A' represents an oxygen atom, a nitrogen atom, a phosphorus atom, or a sulfur atom;

B' represents a hydrogen atom or a monovalent organic group;

$n^{11'}$ represents an integer of 1 or more; and when more than one E' is present, they may be the same as or different from each other, and when more than one A' is present, they may be the same as or different from each other.]

Examples of E' include a hydrocarbylene group optionally having substituent(s), and the number of carbon atoms is preferably in a range of 1 to 60 (the number of carbon atoms does not include the number of carbon atoms of the substituent(s)). The hydrocarbylene group may be any of linear, branched, and cyclic.

In view of the convenience of the synthesis of the compound of the present invention, E' is:

preferably a methylene group, an ethylene group, a propylene group, a butylene group, a pentylene group, a hexylene group, an octylene group, a decylene group, a dodecylene group, a 2-ethylhexylene group, a 3,7-dimethyloctylene group, a cyclopropylene group, a cyclopentylene group, a cyclohexylene group, an α,α-dimethylenebenzyl group, a 1-phenethylene group, a 2-phenethylene group, a vinylene group, a propenylene group, a butenylene group, an oleylene group, a phenylene group, a tolylene group, a biphenylene group, a terphenylene group, a 3,5-dimethylphenylene group, a 4-(1,2,2-triphenylvinyl)phenylene group, a naphthylene group, an anthrylene group, or a phenanthrylene group, more preferably a methylene group, an ethylene group, a propylene group, a butylene group, a pentylene group, a hexylene group, an octylene group, a decylene group, a dodecylene group, a 2-ethylhexylene group, a 3,7-dimethyloctylene group, a vinylene group, a propenylene group, a butenylene group, a phenylene group, a tolylene group, or a biphenylene group, further preferably a methylene group, an ethylene group, a propylene group, a butylene group, a hexylene group, an octylene group, a vinylene group, or a phenylene group, and particularly preferably an ethylene group, a propylene group, or a butylene group.

The above A' is an oxygen atom, a nitrogen atom, a phosphorus atom, or a sulfur atom. In view of the stability (in particular, stability in the atmosphere) of the compound of the present invention, A' is preferably an oxygen atom or a nitrogen atom and more preferably an oxygen atom.

Examples of B' include a hydrogen atom and a hydrocarbyl group optionally having substituent(s), and the number of carbon atoms is preferably in a range of 1 to 60 (the number of carbon atoms does not include the number of carbon atoms of the substituent(s)). The hydrocarbyl group may be any of linear, branched, and cyclic.

In view of the convenience of the synthesis of the compound of the present invention, B' is:

preferably a hydrogen atom, a methyl group, an ethyl group, a 1-propyl group, a 2-propyl group, a 1-butyl group, a 2-butyl group, an isobutyl group, a tert-butyl group, a pentyl group, a hexyl group, an octyl group, a decyl group, a dodecyl group, a 2-ethylhexyl group, a 3,7-dimethyloctyl group, a cyclopropyl group, a cyclopentyl group, a cyclohexyl group, a 1-adamantyl group, a 2-adamantyl group, a benzyl group, an α,α-dimethylbenzyl group, a 1-phenethyl group, a 2-phenethyl group, a vinyl group, a propenyl group, a butenyl group, an oleyl group, a phenyl group, a 2-tolyl group, a 4-tolyl group, a 2-biphenyl group, a 3-biphenyl group, a 4-biphenyl group, a terphenyl group, a 3,5-diphenylphenyl group, a 4-(1,2,2-triphenylvinyl)phenyl group, a 1-naphthyl group, a 2-naphthyl group, a 9-anthryl group, a 2-anthryl group, or a 9-phenanthryl group, more preferably a hydrogen atom, a methyl group, an ethyl group, a 1-propyl group, a 2-propyl group, a 1-butyl group, a 2-butyl group, an isobutyl group, a tert-butyl group, a pentyl group, a hexyl group, an octyl group, a decyl group, a dodecyl group, a 2-ethylhexyl group, a 3,7-dimethyloctyl group, a benzyl group, a 1-adamantyl group, a 2-adamantyl group, a vinyl group, a propenyl group, a butenyl group, a phenyl group, a 2-tolyl group, a 4-tolyl group, a 2-biphenyl group, a 3-biphenyl group, or a 4-biphenyl group, further preferably a hydrogen atom, a methyl group, an ethyl group, a 1-propyl group, a 2-propyl group, a 1-butyl group, or a phenyl group, and particularly preferably a hydrogen atom or a methyl group.

The above $n^{11'}$ represents an integer of 1 or more. In view of the synthesis of the compound of the present invention, $n^{11'}$ is preferably 2 to 8, more preferably 2 to 6, further preferably 2 to 4, and particularly preferably 3 or 4.

In view of the synthesis and the stability (in particular, stability in the atmosphere) of the compound of the present invention, $R^5$ is preferably a monovalent organic group having two or more oxygen atoms. Examples of $R^5$ include an organic group remaining after removing one hydrogen atom from a compound represented by any one of Formulae 3-1 to 3-27. Among these, in view of the synthesis of the compound of the present invention, $R^5$ is more preferably an organic group remaining after removing one hydrogen atom from a compound represented by any one of Formulae 3-1 to 3-8, further preferably an organic group remaining after removing one hydrogen atom from a compound represented by any one of Formulae 3-1 to 3-4 and 3-6, and particularly preferably an organic group remaining after removing one hydrogen atom from a compound represented by Formulae 3-3 or 3-4. The organic group remaining after removing one hydrogen atom from a compound represented by any one of Formulae 3-1 to 3-27 optionally has substituent(s).

[Chemical Formula 12]

3-1

HO~~~O~

3-2

HO~~~O~~~O~

3-3

HO~~~O~~~O~~~O~

3-4

HO~~~O~~~O~~~O~~~O~

[Chemical Formula 13]

3-6

HO~~(OH)~~O~

3-7

HO~~(OH)~~O~~O~

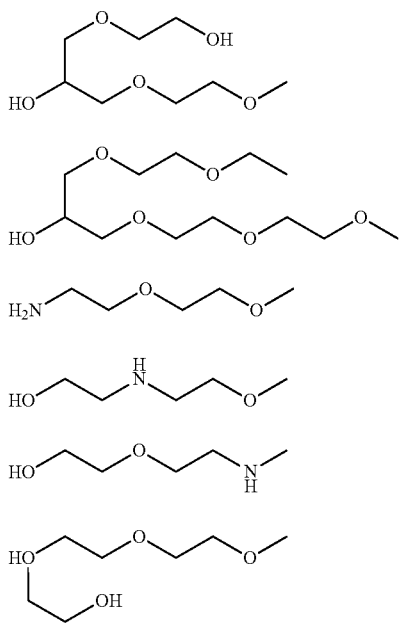
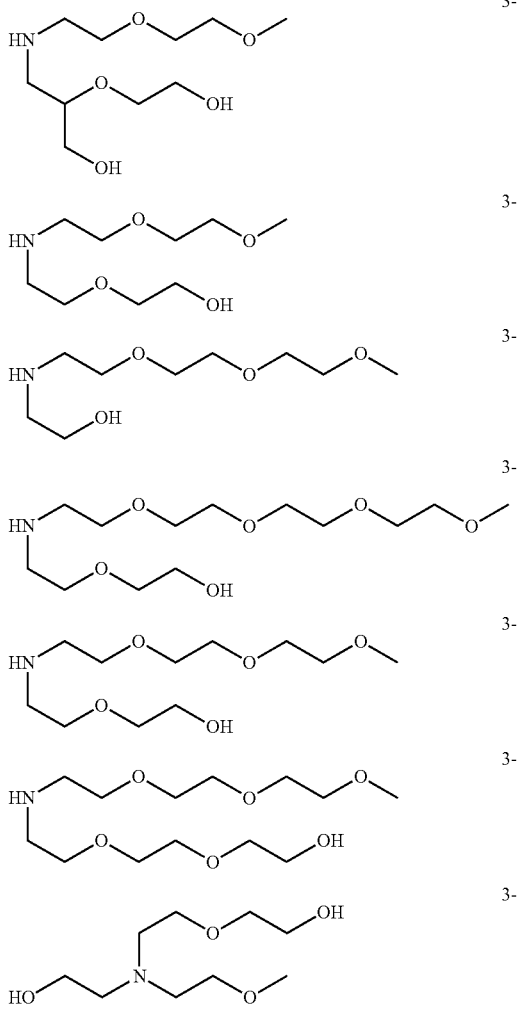
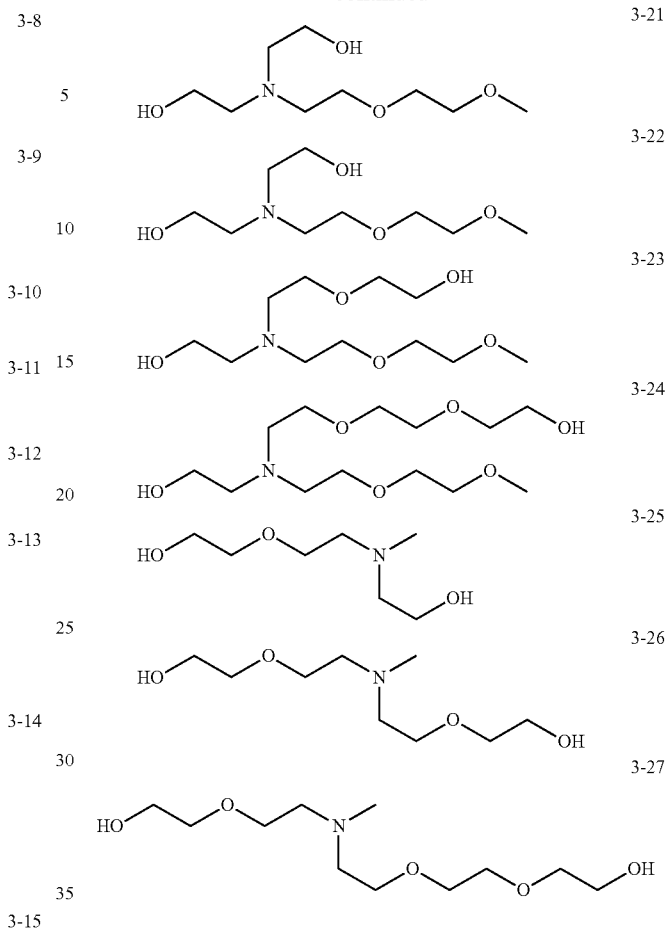

Examples of the monovalent group comprising an anion represented by $Y^1$ include $-CO_2^-$, $-SO_2^-$, $-SO_3^-$, $-O^-$, $-PO_3^{2-}$, and $-Br^a{}_3^-$. When more than one $Y^1$ is present, they may be the same as or different from each other. Among these, in view of the synthesis of the compound of the present invention, $Y^1$ is preferably $-CO_2^-$ or $-SO_3^-$ and more preferably $-CO_2^-$.

The above $R^a$ represents a hydrogen atom or a monovalent organic group. A plurality of $R^a$ may be the same as or different from each other and may be bonded to each other to form a ring.

When $R^a$ form no ring, examples of $R^a$ include a hydrogen atom and a hydrocarbyl group optionally having substituent(s), and the number of carbon atoms of the hydrocarbyl group is preferably in a range of 1 to 60 (the number of carbon atoms does not include the number of carbon atoms of the substituent(s)).

When $R^a$ form no ring, in view of the synthesis of the compound of the present invention, $R^a$ is:

preferably, a hydrogen atom, a methyl group, an ethyl group, a 1-propyl group, a 2-propyl group, a 1-butyl group, a 2-butyl group, an isobutyl group, a tert-butyl group, a pentyl group, a hexyl group, an octyl group, a decyl group, a dodecyl group, a 2-ethylhexyl group, a 3,7-dimethyloctyl group, a cyclopropyl group, a cyclopentyl group, a cyclohexyl group, a 1-adamantyl group, a 2-adamantyl group, a benzyl group, an α,α-dimethylbenzyl group, a 1-phenethyl group, a 2-phenethyl group, a vinyl group, a propenyl group, a butenyl group, an oleyl group, a phenyl group, a 2-tolyl group, a 4-tolyl group, a 2-biphenyl group, a 3-biphenyl group, a 4-biphenyl group, a terphenyl group, a 3,5-diphenylphenyl group, a 4-(1,2,2-triphenylvinyl)phenyl group, a 1-naphthyl group, a 2-naphthyl group, a 9-anthryl group, a 2-anthryl group, or a 9-phenanthryl group, more preferably a methyl group, an ethyl group, a 1-propyl group, a 2-propyl group, a 1-butyl group, a 2-butyl group, an isobutyl group, a tert-butyl group, a pentyl group, a hexyl group, an octyl group, a decyl group, a dodecyl group, a 2-ethylhexyl group, a 3,7-dimethyloctyl group, a benzyl group, a 1-adamantyl group, a 2-adamantyl group, a vinyl group, a propenyl group, a butenyl group, a phenyl group, a 2-tolyl group, a 4-tolyl group, a 2-biphenyl group, a 3-biphenyl group, or a 4-biphenyl group, further preferably a methyl group, an ethyl group, a 1-propyl group, a 2-propyl group, a 1-butyl group, or a phenyl group, and particularly preferably a methyl group or a phenyl group.

When $R^a$ form a ring, for example, two $R^a$ form a hydrocarbylene group optionally having substituent(s), and the number of carbon atoms of the hydrocarbylene group is preferably in a range of 3 to 60 (the number of carbon atoms does not include the number of carbon atoms of the substituent(s)).

In view of the synthesis of the compound of the present invention, a group that the two $R^a$ form a ring is:

preferably a propylene group, a butylene group, a pentylene group, a hexylene group, an octylene group, a decylene group, a dodecylene group, a 2-ethylhexylene group, a 3,7-dimethyloctylene group, or an α,α-dimethylenebenzyl group, more preferably a propylene group, a butylene group, a pentylene group, a hexylene group, an octylene group, a decylene group, a dodecylene group, a 2-ethylhexylene group, or a 3,7-dimethyloctylene group, further preferably a propylene group, a butylene group, a hexylene group, or an octylene group, and particularly preferably a propylene group or a butylene group.

The above $n^1$ represents an integer of 0 or more (e.g., 0 to 4). It is preferable that $n^1$ is 1 or 2.

The above $n^2$ represents 0 or 1. It is preferable that $n^2$ is 0.

The above $n^3$ represents an integer of 0 or more (e.g., 0 to 4). It is preferable that $n^3$ is 0 or 1.

With respect to $n^1$ and $n^3$, $n^1+n^3 \geq 1$ is satisfied; $n^3$ is preferably 1 when $n^1$ is 0; and $n^3$ is preferably 0 when $n^1$ is 1.

Examples of the cation represented by $M^1$ include a metal cation, an ammonium cation optionally having substituent(s), a phosphonium cation having substituent(s), a sulfonium cation having substituent(s), a sulfoxyonium cation having substituent(s), and an iodonium cation having substituent(s). When more than one $M^1$ is present, they may be the same as or different from each other.

Since the charge injectability and charge transportability of the compound of the present invention are excellent, $M^1$ is preferably Li$^+$, Na$^+$, K$^+$, Rb$^+$, Cs$^+$, (R$^b$)$_4$N$^+$, Be$^{2+}$, Mg$^{2+}$, Ca$^{2+}$, Sr$^{2+}$, or Ba$^{2+}$, more preferably Li$^+$, Na$^+$, K$^+$, Rb$^+$, Cs$^+$, (R$^b$)$_4$N$^+$, Mg$^{2+}$, or Ca$^{2+}$, further preferably Li$^+$, Na$^+$, K$^+$, Rb$^+$, Cs$^+$, or (R$^b$)$_4$N$^+$, and particularly preferably Li$^+$, Na$^+$, K$^+$, or Cs$^+$.

The above $R^b$ represents a hydrogen atom or a monovalent organic group. $R^b$ may be the same as or different from each other and may be bonded to each other to form a ring.

When $R^b$ form no ring, examples of $R^b$ include a hydrogen atom, and a hydrocarbyl group optionally having substituent(s), and the number of carbon atoms of the hydrocarbyl group is preferably in a range of 1 to 60 (the number of carbon atoms does not include the number of carbon atoms of the substituent(s)).

When $R^b$ form no ring, in view of the synthesis of the compound of the present invention, $R^b$ is:

preferably a hydrogen atom, a methyl group, an ethyl group, a 1-propyl group, a 2-propyl group, a 1-butyl group, a 2-butyl group, an isobutyl group, a tert-butyl group, a pentyl group, a hexyl group, an octyl group, a decyl group, a dodecyl group, a 2-ethylhexyl group, a 3,7-dimethyloctyl group, a cyclopropyl group, a cyclopentyl group, a cyclohexyl group, a 1-adamantyl group, a 2-adamantyl group, a benzyl group, an α,α-dimethylbenzyl group, a 1-phenethyl group, a 2-phenethyl group, a vinyl group, a propenyl group, a butenyl group, an oleyl group, a phenyl group, a 2-tolyl group, a 4-tolyl group, a 2-biphenyl group, a 3-biphenyl group, a 4-biphenyl group, a terphenyl group, a 3,5-diphenylphenyl group, a 4-(1,2,2-triphenylvinyl)phenyl group, a 1-naphthyl group, a 2-naphthyl group, a 9-anthryl group, a 2-anthryl group, or a 9-phenanthryl group, more preferably a methyl group, an ethyl group, a 1-propyl group, a 2-propyl group, a 1-butyl group, a 2-butyl group, an isobutyl group, a tert-butyl group, a pentyl group, a hexyl group, an octyl group, a decyl group, a dodecyl group, a 2-ethylhexyl group, a 3,7-dimethyloctyl group, a benzyl group, a 1-adamantyl group, a 2-adamantyl group, a vinyl group, a propenyl group, a butenyl group, a phenyl group, a 2-tolyl group, a 4-tolyl group, a 2-biphenyl group, a 3-biphenyl group, or a 4-biphenyl group further preferably a methyl group, an ethyl group, a 1-propyl group, a 2-propyl group, a 1-butyl group, or a phenyl group, and particularly preferably a methyl group or a 1-butyl group.

When $R^b$ form a ring, for example, two $R^b$ form a hydrocarbylene group optionally having substituent(s), and the number of carbon atoms of the hydrocarbylene group is preferably in a range of 3 to 60 (the number of carbon atoms does not include the number of carbon atoms of the substituent(s)).

In view of the synthesis of the compound of the present invention, a group that the two $R^b$ form a ring is:

preferably a propylene group, a butylene group, a pentylene group, a hexylene group, an octylene group, a decylene group, a dodecylene group, a 2-ethylhexylene group, a 3,7-dimethyloctylene group, or an α,α-dimethylenebenzyl group, more preferably a propylene group, a butylene group, a pentylene group, a hexylene group, an octylene group, a decylene group, a dodecylene group, a 2-ethylhexylene group, or a 3,7-dimethyloctylene group, further preferably a propylene group, a butylene group, a hexylene group, or an octylene group, and particularly preferably a propylene group or a butylene group.

The above $Z^1$ represents an anion, in particular, a counter anion. When more than one $Z^1$ is present, they may be the same as or different from each other.

Examples of $Z^1$ include F$^-$, Cl$^-$, Br$^-$, I$^-$, OH$^-$, CH$_3$SO$_3^-$, C$_6$H$_5$SO$_3^-$, p-H$_3$CC$_6$H$_4$SO$_3^-$, p-BrC$_6$H$_4$SO$_3^-$, o-O$_2$NC$_6$H$_4$SO$_3^-$, p-O$_2$NC$_6$H$_4$SO$_3^-$, C$_4$H$_9$SO$_3^-$, C$_6$H$_5$CH$_2$SO$_3^-$, CH$_3$CO$_2^-$, C$_6$H$_5$CO$_2^-$, p-O$_2$NC$_6$H$_4$CO$_2^-$, C$_4$H$_9$CO$_2^-$, C$_6$H$_5$CH$_2$CO$_2^-$, CF$_3$SO$_3^-$, CF$_3$CO$_2^-$, ClO$^-$, ClO$_2^-$, ClO$_3^-$, ClO$_4^-$, SCN$^-$, CN$^-$, NO$_3^-$, SO$_4^{2-}$, HSO$_4^-$, PO$_4^{3-}$, HPO$_4^{2-}$, H$_2$PO$_4^-$, BPh$_4^-$, B[3,5-(CF$_3$)$_2$C$_6$H$_3$]$_4^-$, B[N-Imidazolyl]$_4^-$, BF$_4^-$, and PF$_6^-$.

Among these, in view of the synthesis of the compound of the present invention, $Z^1$ is:

preferably CF$_3$SO$_3^-$, CF$_3$CO$_2^-$, BPh$_4^-$, B[3,5-(CF$_3$)$_2$C$_6$H$_3$]$_4^-$, B[N-Imidazolyl]$_4^-$, BF$_4^-$, or PF$_6^-$, more preferably B[3,5-(CF$_3$)$_2$C$_6$H$_3$]$_4^-$, B[N-Imidazolyl]$_4^-$, BF$_4^-$, or PF$_6^-$, and further preferably B[N-Imidazolyl]$_4^-$.

The above a represents an integer of 1 or more. In view of the synthesis of the compound of the present invention, the a is preferably 1 or more and 3 or less.

The above b represents an integer of 0 or more. In view of the synthesis of the compound of the present invention, the b is preferably 0 or more and 2 or less.

Described is a low molecular compound which is the compound comprising the structure represented by Formula (1) and which is the first compound of the present invention. Examples of the low molecular compound include a compound represented by any one of Formulae 4-1 to 4-36. Among these, in view of the synthesis of the low molecular compound, the low molecular compound is preferably a compound represented by any one of Formulae 4-1, 4-4, 4-5, 4-8, 4-9, 4-12, 4-13, 4-16, 4-17, 4-20, 4-21, 4-24, 4-25, 4-28, 4-29, 4-324-33, and 4-36, more preferably a compound represented by any one of Formulae 4-1, 4-4, 4-9, 4-12, 4-17, 4-20, 4-21, 4-24, 4-25, and 4-28, further preferably a compound represented by any one of Formulae 4-1, 4-4, 4-9, and 4-12, and particularly preferably a compound represented by Formulae 4-9 or 4-12. The compound represented by any one of Formulae 4-1 to 4-36 may have substituent(s).

[Chemical Formula 15]

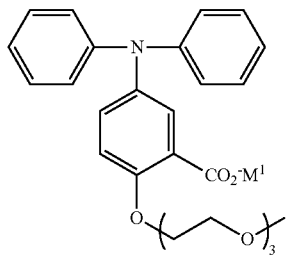

4-1: $M^1 = Li^+$
4-2: $M^1 = Na^+$
4-3: $M^1 = K^+$
4-4: $M^1 = Cs^+$

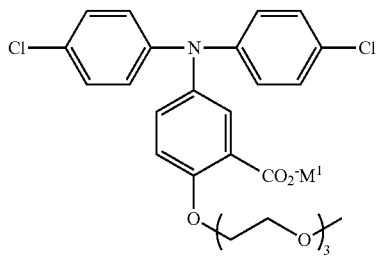

4-5: $M^1 = Li^+$
4-6: $M^1 = Na^+$
4-7: $M^1 = K^+$
4-8: $M^1 = Cs^+$

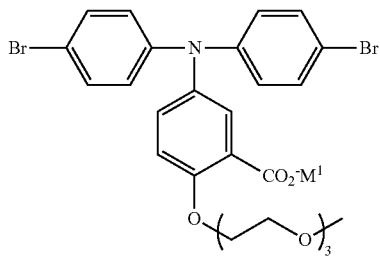

4-9: $M^1 = Li^+$
4-10: $M^1 = Na^+$
4-11: $M^1 = K^+$
4-12: $M^1 = Cs^+$

-continued

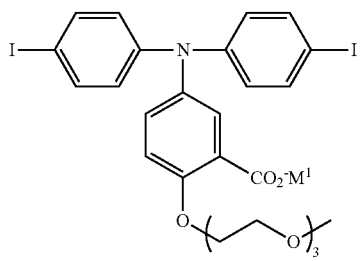

4-13: $M^1 = Li^+$
4-14: $M^1 = Na^+$
4-15: $M^1 = K^+$
4-16: $M^1 = Cs^+$

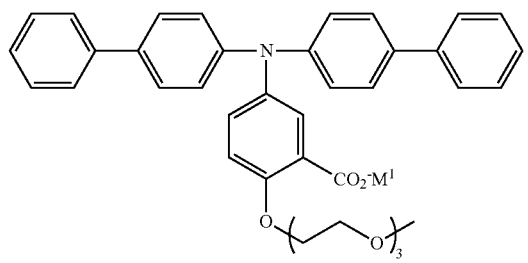

4-17: $M^1 = Li^+$
4-18: $M^1 = Na^+$
4-19: $M^1 = K^+$
4-20: $M^1 = Cs^+$

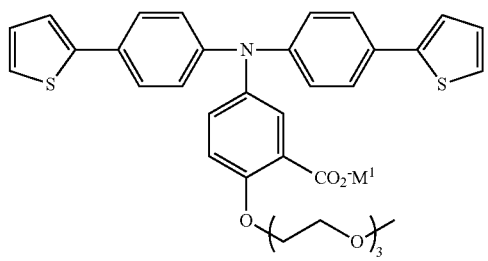

4-21: $M^1 = Li^+$
4-22: $M^1 = Na^+$
4-23: $M^1 = K^+$
4-24: $M^1 = Cs^+$

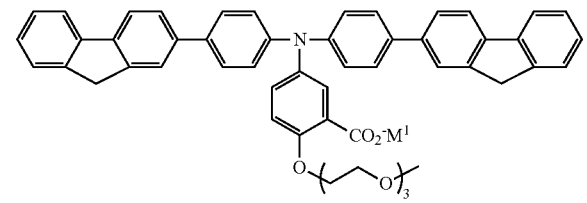

4-25: $M^1 = Li^+$
4-26: $M^1 = Na^+$
4-27: $M^1 = K^+$
4-28: $M^1 = Cs^+$

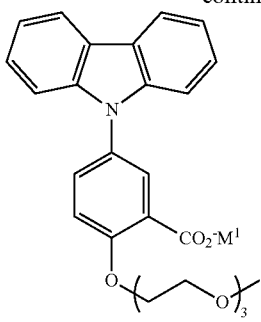

4-29: $M^1 = Li^+$
4-30: $M^1 = Na^+$
4-31: $M^1 = K^+$
4-32: $M^1 = Cs^+$

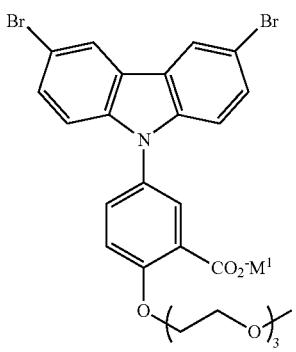

4-33: $M^1 = Li^+$
4-34: $M^1 = Na^+$
4-35: $M^1 = K^+$
4-36: $M^1 = Cs^+$

The compound comprising the structure represented by Formula (1) which is the first compound of the present invention is preferably a compound comprising a structure represented by Formula (3). This is because an electroluminescent device using a stacked structure increases in performance (in particular, the light-emitting efficiency is higher). The structure represented by Formula (3) represents a divalent structure.

[Chemical Formula 16]

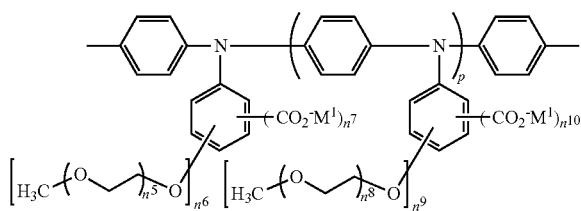

(3)

[In the formula:

p and $M^1$ represent the same meaning as described above;

$n^5$ and $n^8$ each independently represent an integer of 1 or more; and $n^6$, $n^7$, $n^9$, and $n^{10}$ each independently represent an integer of 1 to 4, and $n^6+n^7 \leq 5$ and $n^9+n^{10} \leq 5$ are satisfied.]

It is preferable that $n^5$ and $n^8$ are each 3 or 4. This is because an electroluminescent device using a stacked structure increases in performance (in particular, the light-emitting efficiency is higher).

It is preferable that $n^6$, $n^7$ $n^9$, and $n^{10}$ are each 1 or 2. This is because an electroluminescent device using a stacked structure increases in performance (in particular, the light-emitting efficiency is higher).

The compound comprising the structure represented by Formula (3) which is the first compound of the present invention is preferably a compound comprising a structure represented by Formula (4), since the light-emitting efficiency of an electroluminescent device using the compound of the present invention is higher. The structure represented by Formula (4) represents a divalent structure.

[Chemical Formula 17]

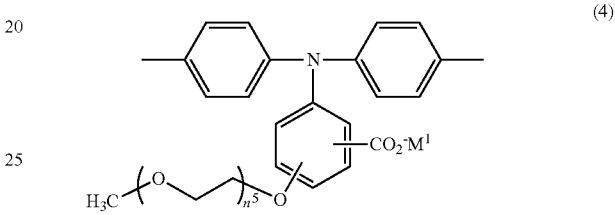

(4)

[In the formula, $M^1$ and $n^5$ represent the same meaning as described above.]

The compound comprising the structure represented by Formula (4) which is the first compound of the present invention is preferably a compound comprising a structure represented by Formula (4'), since the light-emitting efficiency of an electroluminescent device using the compound of the present invention is higher. The structure represented by Formula (4') represents a divalent structure.

[Chemical Formula 18]

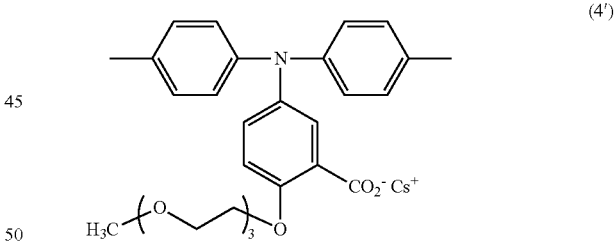

(4')

The polymer compound which is the first compound of the present invention may comprise one or more structures selected from the group consisting of the structures represented by Formulae (1), (3), (4), and (4') as a constitutional unit and may comprise another constitutional unit in addition to the above constitutional units. Examples of the other constitutional unit include a structure represented by Formula (9). The structure represented by Formula (9) represents a divalent structure.

[Chemical Formula 19]

$$-\!\!\left(\!R^7\!\right)\!\!- \quad (9)$$

$R^7$ is a divalent organic group optionally having substituent(s) (which is different from the constitutional units represented by Formulae (1), (3), (4), and (4')), and examples of R⁷ include an atomic group remaining after removing two hydrogen atoms bonded to a ring of a molecule represented by any one of Formulae 7-1 to 7-124.

Among these, in view of the synthesis of the compound of the present invention, $R^7$ is:

preferably an atomic group remaining after removing two hydrogen atoms bonded to a ring of a molecule represented by any one of Formulae 7-1, 7-2, 7-3, 7-10, 7-12, 7-20, 7-32, 7-34, 7-35, 7-36, 7-37, 7-38, 7-50, 7-53, 7-54, 7-57, 7-58, 7-61, 7-66, 7-69, 7-70, 7-73, 7-76, 7-77, 7-80, 7-81, 7-84, 7-85, 7-88, 7-89, 7-92, 7-93, 7-96, 7-97, 7-100, 7-101, 7-104, 7-105, 7-108, 7-109, 7-112, 7-113, 7-116, 7-117, 7-120, 7-121, and 7-124, more preferably an atomic group remaining after removing two hydrogen atoms bonded to a ring of a molecule represented by any one of Formulae 7-1, 7-2, 7-10, 7-32, 7-35, 7-38, 7-58, 7-61, 7-76, 7-85, 7-88, 7-97, 7-100, 7-109, 7-112, 7-121, and 7-124, further preferably an atomic group remaining after removing two hydrogen atoms bonded to a ring of a molecule represented by any one of Formulae 7-1, 7-10, 7-32, 7-35, 7-58, 7-61, 7-76, 7-85, 7-88, 7-109, and 7-112, and particularly preferably an atomic group remaining after removing two hydrogen atoms bonded to a ring of a molecule represented by any one of Formulae 7-58, 7-61, 7-76, 7-85, and 7-88. In the following formulae, $M^1$ represents the same meaning as described above.

[Chemical Formula 20]

[Chemical Formula 21]

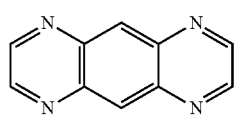
7-21
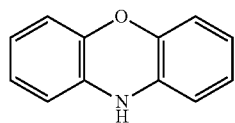
7-22
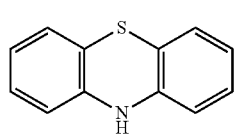
7-23
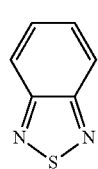
7-24
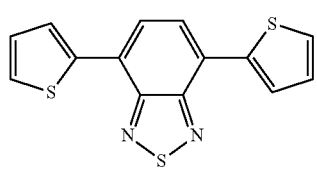
7-25
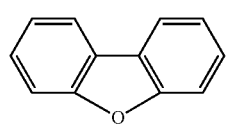
7-26
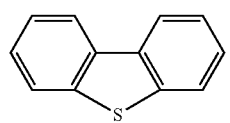
7-27
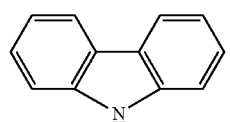
7-28
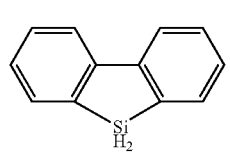
7-29
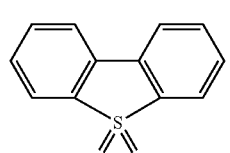
7-30
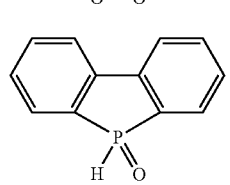
7-31
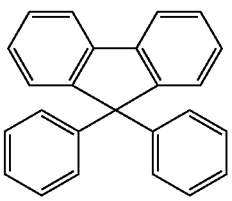
7-32
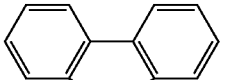
7-33
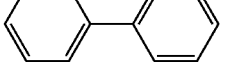
7-34
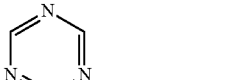
7-35
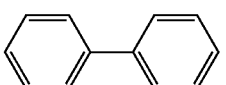
7-36
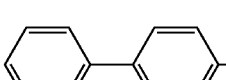
7-37
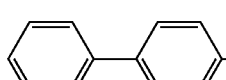
7-38
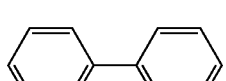
7-39
7-40

-continued
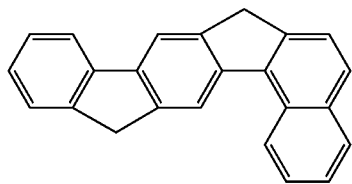
[Chemical Formula 22]
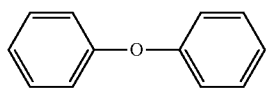
7-42
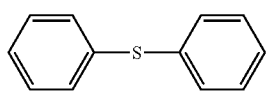
7-43
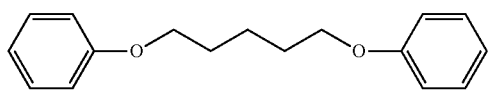
7-44
7-45
7-46
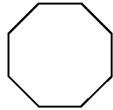
7-47
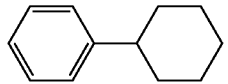
7-48
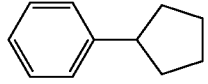
7-49
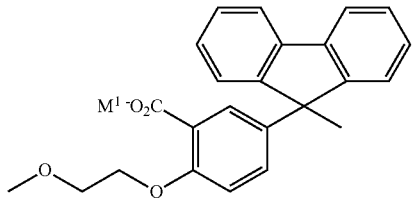
7-50 M¹ = Li⁺
7-51 M¹ = Na⁺
7-52 M¹ = K⁺
7-53 M¹ = Cs⁺
7-41
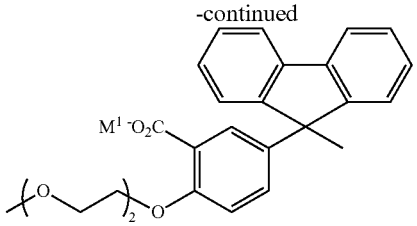
7-54 M¹ = Li⁺
7-55 M¹ = Na⁺
7-56 M¹ = K⁺
7-57 M¹ = Cs⁺
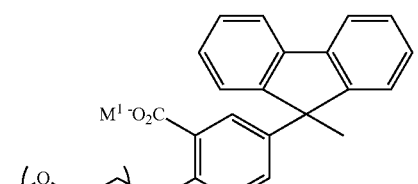
7-58 M¹ = Li⁺
7-59 M¹ = Na⁺
7-60 M¹ = K⁺
7-61 M¹ = Cs⁺
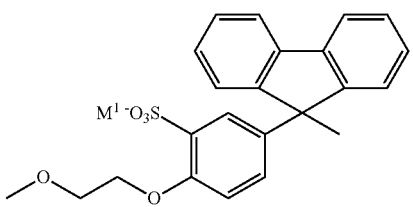
7-62 M¹ = Li⁺
7-63 M¹ = Na⁺
7-64 M¹ = K⁺
7-65 M¹ = Cs⁺
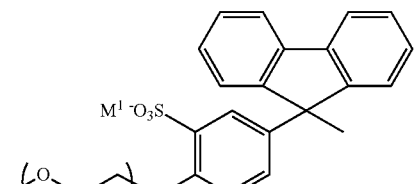
7-66 M¹ = Li⁺
7-67 M¹ = Na⁺
7-68 M¹ = K⁺
7-69 M¹ = Cs⁺
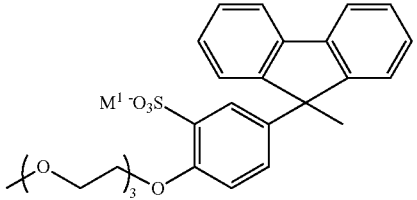
7-70 M¹ = Li⁺
7-71 M¹ = Na⁺
7-72 M¹ = K⁺
7-73 M¹ = Cs⁺

7-74

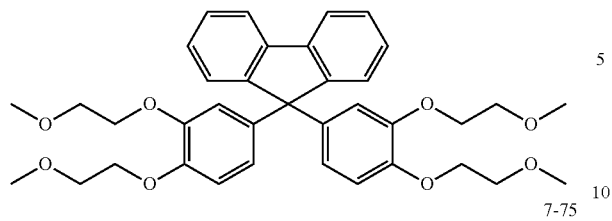

7-75

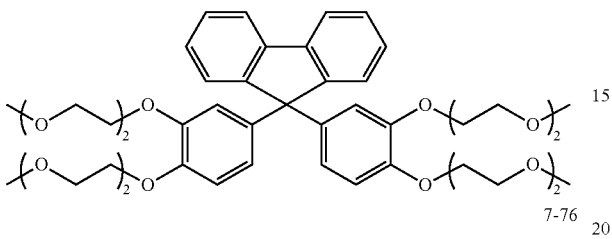

7-76

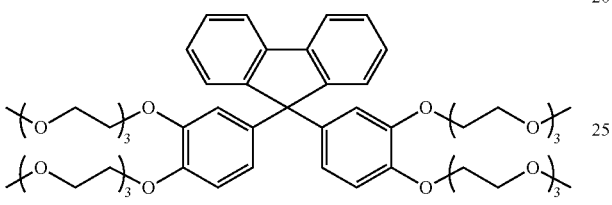

[Chemical Formula 23]

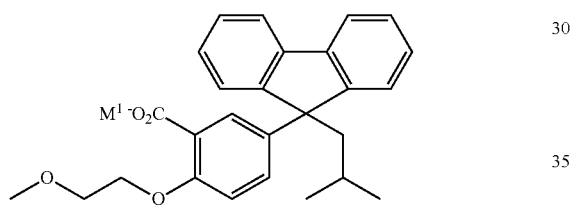

7-77 M$^1$ = Li$^+$
7-78 M$^1$ = Na$^+$
7-79 M$^1$ = K$^+$
7-80 M$^1$ = Cs$^+$

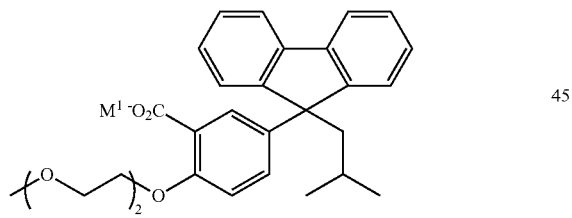

7-81 M$^1$ = Li$^+$
7-82 M$^1$ = Na$^+$
7-83 M$^1$ = K$^+$
7-84 M$^1$ = Cs$^+$

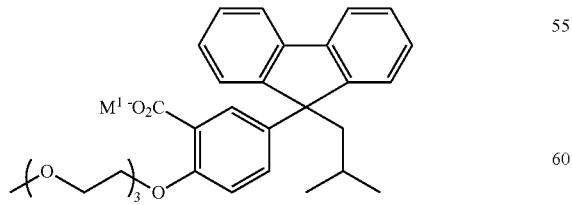

7-85 M$^1$ = Li$^+$
7-86 M$^1$ = Na$^+$
7-87 M$^1$ = K$^+$
7-88 M$^1$ = Cs$^+$

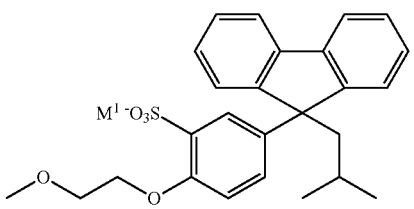

7-89 M$^1$ = Li$^+$
7-90 M$^1$ = Na$^+$
7-91 M$^1$ = K$^+$
7-92 M$^1$ = Cs$^+$

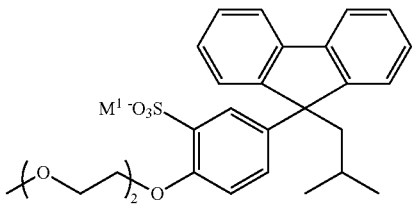

7-93 M$^1$ = Li$^+$
7-94 M$^1$ = Na$^+$
7-95 M$^1$ = K$^+$
7-96 M$^1$ = Cs$^+$

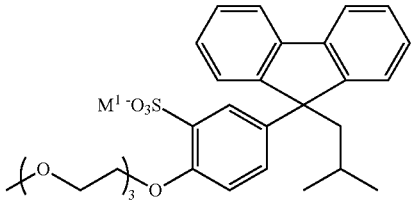

7-97 M$^1$ = Li$^+$
7-98 M$^1$ = Na$^+$
7-99 M$^1$ = K$^+$
7-100 M$^1$ = Cs$^+$

[Chemical Formula 24]

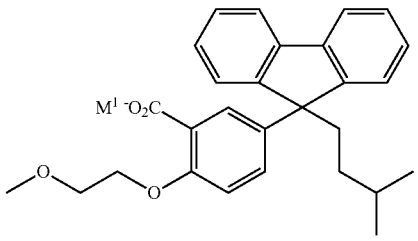

7-101 M$^1$ = Li$^+$
7-102 M$^1$ = Na$^+$
7-103 M$^1$ = K$^+$
7-104 M$^1$ = Cs$^+$

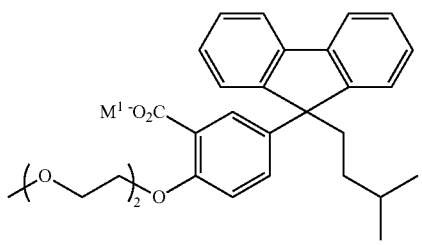

7-105 M¹ = Li⁺
7-106 M¹ = Na⁺
7-107 M¹ = K⁺
7-108 M¹ = Cs⁺

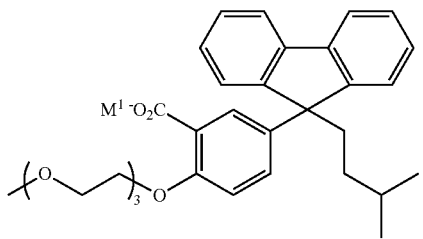

7-109 M¹ = Li⁺
7-110 M¹ = Na⁺
7-111 M¹ = K⁺
7-112 M¹ = Cs⁺

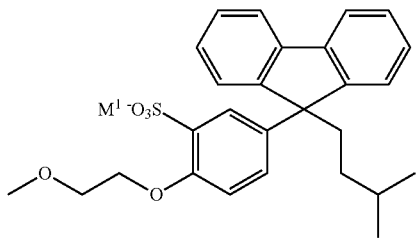

7-113 M¹ = Li⁺
7-114 M¹ = Na⁺
7-115 M¹ = K⁺
7-116 M¹ = Cs⁺

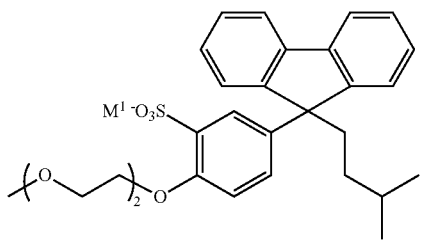

7-117 M¹ = Li⁺
7-118 M¹ = Na⁺
7-119 M¹ = K⁺
7-120 M¹ = Cs⁺

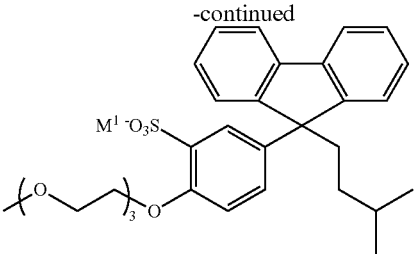

7-121 M¹ = Li⁺
7-122 M¹ = Na⁺
7-123 M¹ = K⁺
7-124 M¹ = Cs⁺

In the polymer compound which is the first compound of the present invention, the ratio of the sum of the constitutional units of the structures represented by Formulae (1), (3), (4), and (4') with respect to all constitutional units comprised in the polymer compound is generally in a range of 0.1% by mole or more and 100% by mole or less. In view of increasing solubility in an organic solvent, the ratio is preferably in a range of 0.1% by mole or more and 80% by mole or less, more preferably in a range of 0.1% by mole or more and 65% by mole or less, and further preferably in a range of 0.1% by mole or more and 50% by mole or less.

In the polymer compound which is the first compound of the present invention, the constitutional unit other than the constitutional units of the structures represented by Formulae (1), (3), (4), and (4') is preferably the constitutional unit represented by Formula (9), and any constitutional unit other than the constitutional unit represented by Formula (9) may be comprised.

Since solubility in an organic solvent and film formability are favorable, the molecular weight of the polymer compound which is the first compound of the present invention is preferably $4 \times 10^3$ or more and $2 \times 10^6$ or less, more preferably $1 \times 10^4$ or more and $1 \times 10^6$ or less, and further preferably $1.5 \times 10^4$ or more and $4 \times 10^5$ or less. The molecular weight of the first compound can be calculated by considering the molecular weight of the second compound of the present invention described below, which is a precursor of the first compound, and a method for manufacturing the first compound from the second compound.

<Second Compound>

The "second compound" of the present invention is a compound comprising a structure represented by Formula (5). The structure represented by Formula (5) represents a divalent structure. The compound encompasses both a polymer compound comprising the structure represented by Formula (5) as a constitutional unit and a low molecular compound comprising the structure represented by Formula (5). Described below is the structure represented by Formula (5).

[Chemical Formula 25]

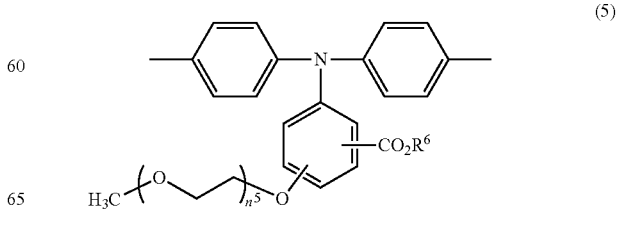

(5)

[In the formula, $n^5$ represents an integer of 1 or more, and $R^6$ represents a monovalent organic group.]

Examples of $R^6$ include a hydrocarbyl group optionally having substituent(s), and the number of carbon atoms of the hydrocarbyl group is preferably in a range of 1 to 60 (the number of carbon atoms does not include the number of carbon atoms of the substituent(s).) The hydrocarbyl group may be any of linear, branched, and cyclic. Since the compound of the present invention can be synthesized conveniently, $R^6$ is:

preferably a methyl group, an ethyl group, a neopentyl group, a 1-propyl group, a 2-propyl group, a 1-butyl group, a 2-butyl group, an isobutyl group, a tert-butyl group, a pentyl group, a hexyl group, an octyl group, a decyl group, a dodecyl group, a 2-ethylhexyl group, a 3,7-dimethyloctyl group, a cyclopropyl group, a cyclopentyl group, a cyclohexyl group, a 1-adamantyl group, a 2-adamantyl group, a benzyl group, an α,α-dimethylbenzyl group, a 1-phenethyl group, a 2-phenethyl group, a vinyl group, a propenyl group, a butenyl group, an oleyl group, a phenyl group, a 2-tolyl group, a 4-tolyl group, a 2-biphenyl group, a 3-biphenyl group, a 4-biphenyl group, a terphenyl group, a 3,5-diphenylphenyl group, a 4-(1,2,2-triphenylvinyl)phenyl group, a 1-naphthyl group, a 2-naphthyl group, a 9-anthryl group, a 2-anthryl group, or a 9-phenanthryl group, more preferably a methyl group, an ethyl group, a neopentyl group, a 1-propyl group, a 2-propyl group, a 1-butyl group, a 2-butyl group, an isobutyl group, a tert-butyl group, a pentyl group, a hexyl group, an octyl group, a decyl group, a dodecyl group, a 2-ethylhexyl group, a 3,7-dimethyloctyl group, a benzyl group, a 1-adamantyl group, a 2-adamantyl group, a vinyl group, a propenyl group, a butenyl group, a phenyl group, a 2-tolyl group, a 4-tolyl group, a 2-biphenyl group, a 3-biphenyl group, or a 4-biphenyl group, further preferably a methyl group, an ethyl group, a neopentyl group, a tert-butyl group, or a phenyl group, and particularly preferably an ethyl group.

In view of the synthesis of the compound of the present invention, the compound comprising the structure represented by Formula (5) which is the second compound of the present invention is preferably a compound comprising a structure represented by Formula (5'). The structure represented by Formula (5') represents a divalent structure.

[Chemical Formula 26]

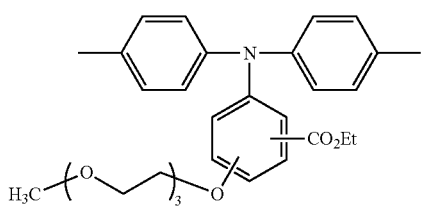

(5')

The compound comprising the structure represented by Formula (5') which is the second compound of the present invention is preferably a compound comprising a structure represented by Formula (5"). The structure represented by Formula (5") represents a divalent structure.

[Chemical Formula 27]

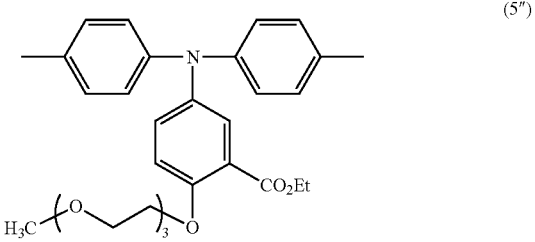

(5")

The polymer compound which is the second compound of the present invention may comprise one or more structures selected from the group consisting of the structures represented by Formulae (5), (5'), and (5") as a constitutional unit and may comprise another constitutional unit in addition to these. Examples of the other constitutional unit include a structure represented by Formula (10). The structure represented by Formula (10) represents a divalent structure.

[Chemical Formula 28]

(10)

$R^8$ is a divalent organic group optionally having substituent(s) (which is different from the constitutional units represented by Formulae (5), (5'), and (5")), and examples of $R^8$ include an atomic group remaining after removing two hydrogen atoms bonded to a ring of a molecule represented by any one of Formulae 8-1 to 8-124.

Among these, since the light-emitting efficiency of an electroluminescent device using the first compound obtained from the second compound of the present invention as a precursor is higher, $R^8$ is:

preferably an atomic group remaining after removing two hydrogen atoms bonded to a ring of a molecule represented by any one of Formulae 8-1, 8-2, 8-3, 8-10, 8-12, 8-20, 8-32, 8-34, 8-35, 8-36, 8-37, 8-38, 8-51, 8-55, 8-59, 8-71, 8-76, 8-78, 8-82, 8-86, 8-102, 8-106, and 8-110, more preferably an atomic group remaining after removing two hydrogen atoms bonded to a ring of a molecule represented by any one of Formulae 8-1, 8-10, 8-35, 8-38, 8-59, 8-76, 8-86, and 8-110, further preferably an atomic group remaining after removing two hydrogen atoms bonded to a ring of a molecule represented by any one of Formulae 8-1, 8-10, 8-59, 8-76, 8-86, and 8-110, and particularly preferably an atomic group remaining after removing two hydrogen atoms bonded to a ring of a molecule represented by any one of Formulae 8-1, 8-10, 8-59, 8-86, and 8-110.

[Chemical Formula 29]

8-1

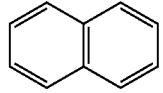

8-2

-continued
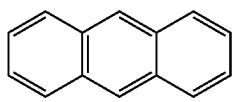
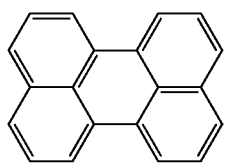
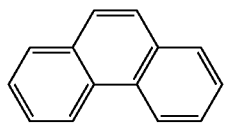
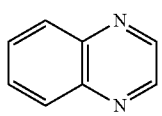
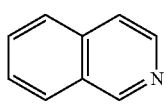
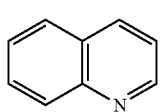
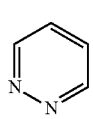
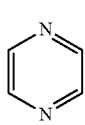
-continued
8-3
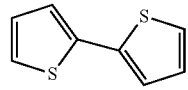
8-4
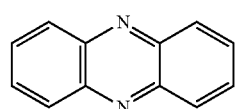
8-5
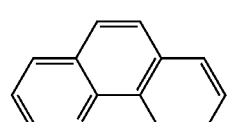
8-6
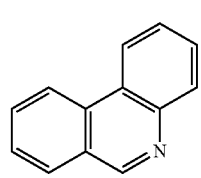
8-7
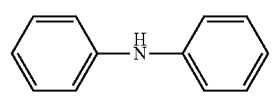
8-8
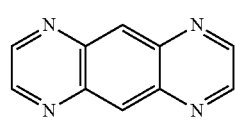
8-9
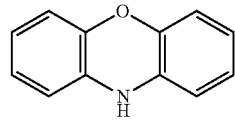
8-10
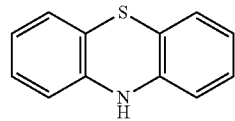
8-11
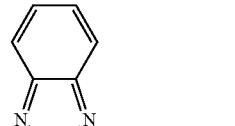
8-12
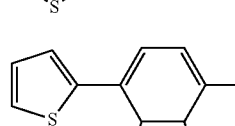
8-13
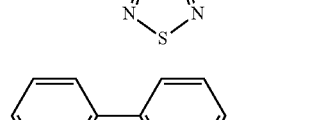
8-14
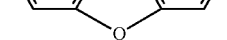
8-15
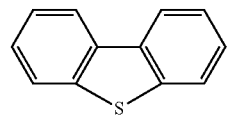

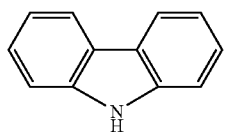
8-28
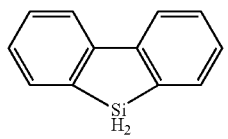
8-29
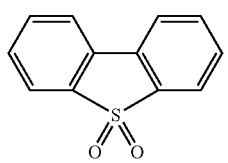
8-30
[Chemical Formula 30]
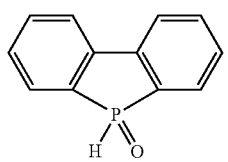
8-31
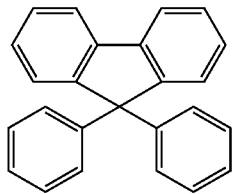
8-32
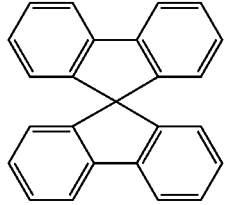
8-33
8-34
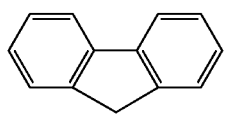
8-35
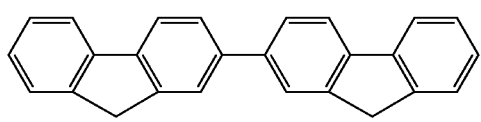
8-36
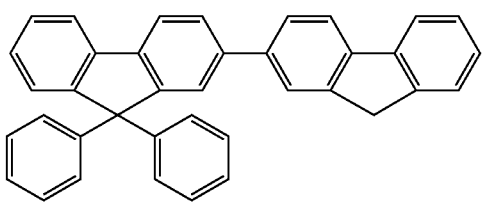
8-37
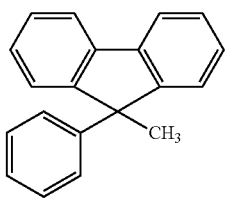
8-38
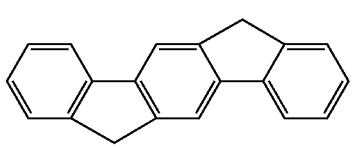
8-39
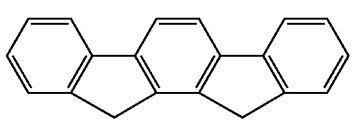
8-40
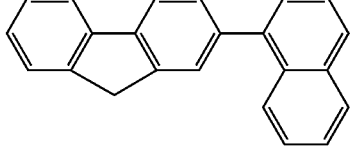
8-41
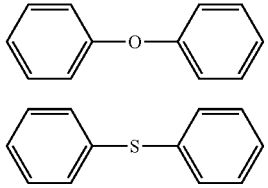
8-42
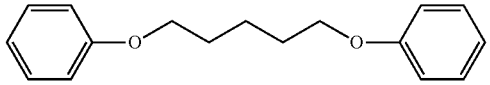
8-43
8-44
8-45
8-46
8-47
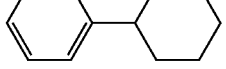
8-48

-continued
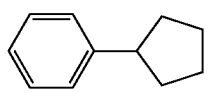
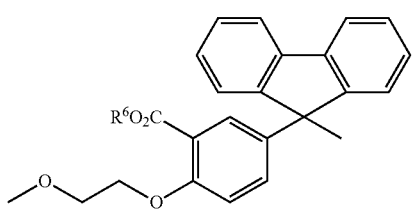
8-50 R⁶ = Me
8-51 R⁶ = Et
8-52 R⁶ = ᵗBu
8-53 R⁶ = Ph
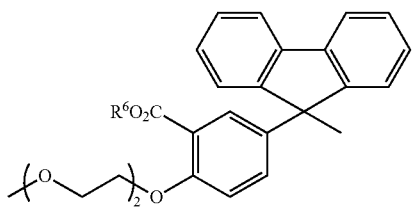
8-54 R⁶ = Me
8-55 R⁶ = Et
8-56 R⁶ = ᵗBu
8-57 R⁶ = Ph
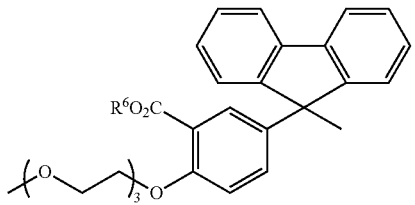
8-58 R⁶ = Me
8-59 R⁶ = Et
8-60 R⁶ = ᵗBu
8-61 R⁶ = Ph
[Chemical Formula 31]
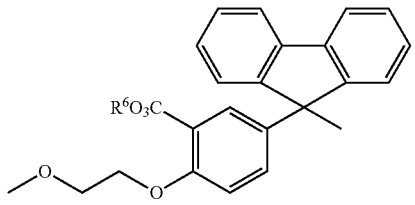
8-62 R⁶ = Me
8-63 R⁶ = Et
8-64 R⁶ = Ph
8-65 R⁶ = ⁿᵉᵒPent
-continued
8-49
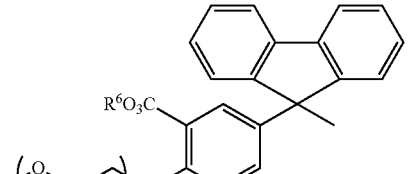
8-66 R⁶ = Me
8-67 R⁶ = Et
8-68 R⁶ = Ph
8-69 R⁶ = ⁿᵉᵒPent
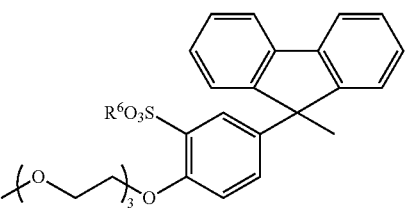
8-70 R⁶ = Me
8-71 R⁶ = Et
8-72 R⁶ = Ph
8-73 R⁶ = ⁿᵉᵒPent
8-74
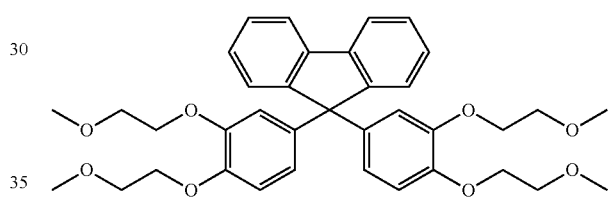
8-75
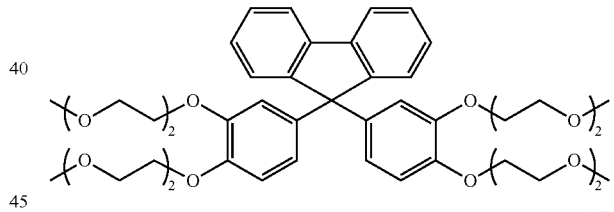
8-76
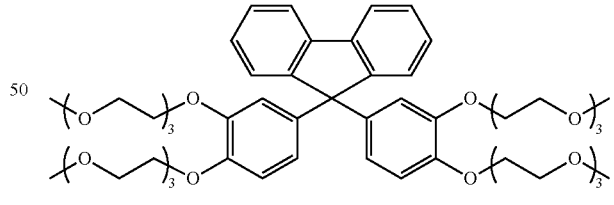
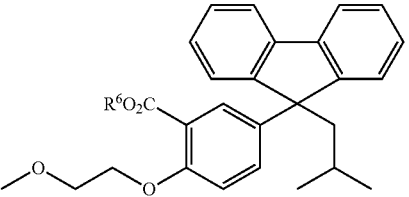
8-77 R⁶ = Me
8-78 R⁶ = Et
8-79 R⁶ = Ph
8-80 R⁶ = ⁿᵉᵒPent -continued
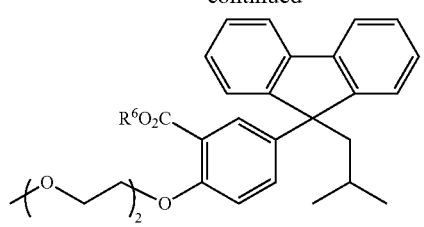
8-81 R⁶ = Me
8-82 R⁶ = Et
8-83 R⁶ = Ph
8-84 R⁶ = ⁿᵉᵒPent
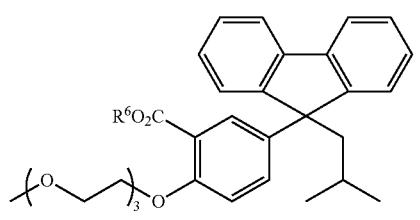
8-85 R⁶ = Me
8-86 R⁶ = Et
8-87 R⁶ = Ph
8-88 R⁶ = ⁿᵉᵒPent
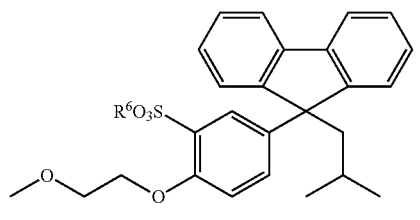
8-89 R⁶ = Me
8-90 R⁶ = Et
8-91 R⁶ = Ph
8-92 R⁶ = ⁿᵉᵒPent
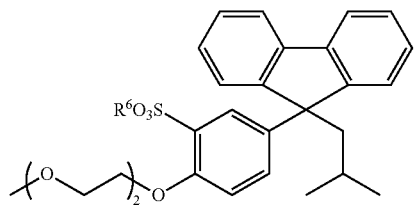
8-93 R⁶ = Me
8-94 R⁶ = Et
8-95 R⁶ = Ph
8-96 R⁶ = ⁿᵉᵒPent
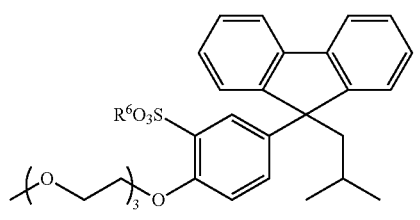
8-97 R⁶ = Me
8-98 R⁶ = Et
8-99 R⁶ = Ph
8-100 R⁶ = ⁿᵉᵒPent
-continued
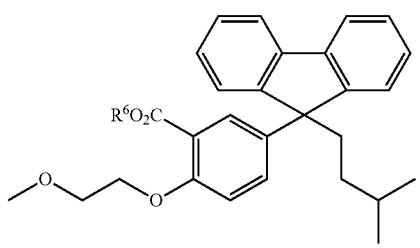
8-101 R⁶ = Me
8-102 R⁶ = Et
8-103 R⁶ = Ph
8-104 R⁶ = ⁿᵉᵒPent
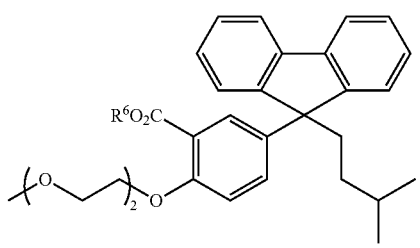
8-105 R⁶ = Me
8-106 R⁶ = Et
8-107 R⁶ = Ph
8-108 R⁶ = ⁿᵉᵒPent
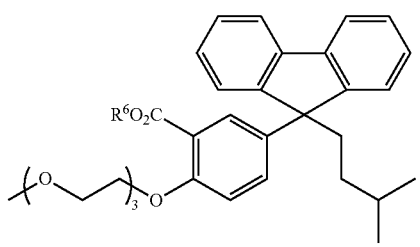
8-109 R⁶ = Me
8-110 R⁶ = Et
8-111 R⁶ = Ph
8-112 R⁶ = ⁿᵉᵒPent
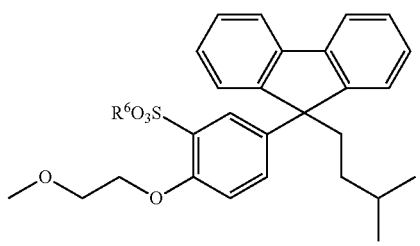
8-113 R⁶ = Me
8-114 R⁶ = Et
8-115 R⁶ = Ph
8-116 R⁶ = ⁿᵉᵒPent

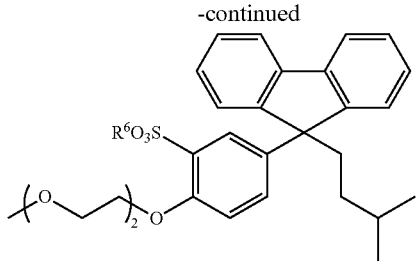

8-117 $R^6$ = Me
8-118 $R^6$ = Et
8-119 $R^6$ = Ph
8-120 $R^6$ = $^{neo}$Pent

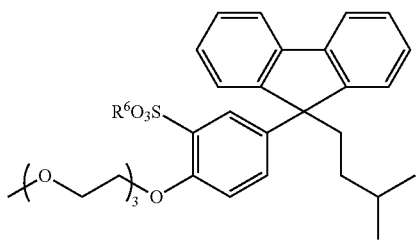

8-121 $R^6$ = Me
8-122 $R^6$ = Et
8-123 $R^6$ = Ph
8-124 $R^6$ = $^{neo}$Pent

In the polymer compound which is the second compound of the present invention, the ratio of the sum of the constitutional units of the structures represented by Formulae (5), (5'), and (5") with respect to all constitutional units comprised in the polymer compound is generally in a range of 0.1% by mole or more and 100% by mole or less. In view of increasing solubility in an organic solvent, the ratio is preferably in a range of 0.1% by mole or more and 80% by mole or less, more preferably in a range of 0.1% by mole or more and 65% by mole or less, and further preferably in a range of 0.1% by mole or more and 50% by mole or less.

In the second compound of the present invention, the constitutional unit other than the constitutional units of the structures represented by Formulae (5), (5'), and (5") is preferably the constitutional unit represented by Formula (10), and any constitutional unit other than the constitutional unit represented by Formula (10) may be comprised.

Since solubility in an organic solvent and film formability are favorable, the molecular weight of the polymer compound which is the second compound of the present invention is preferably $4\times10^3$ or more and $4\times10^6$ or less, more preferably $1\times10^4$ or more and $1\times10^6$ or less, and further preferably $1.5\times10^4$ or more and $4\times10^5$ or less. The molecular weight of the second compound means a weight average molecular weight calculated by polystyrene conversion using gel permeation chromatography (GPC).

A compound represented by Formula (6) which is the second compound of the present invention is particularly useful as a base material for the polymer compound comprising the structures represented by Formulae (5), (5'), or (5") as constitutional units. Described below is the compound represented by Formula (6).

[Chemical Formula 32]

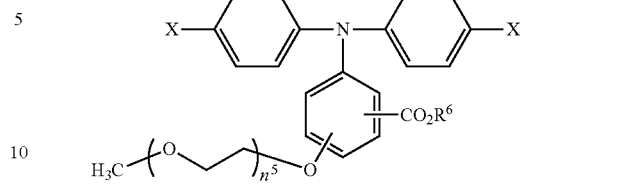

(6)

[In the formula,
$n^5$ and $R^6$ represent the same meaning as described above;
X represents a chlorine atom, a bromine atom, an iodine atom, a p-toluenesulfonate group, a trifluoromethanesulfonate group, a methanesulfonate group, a dihydroxyboryl group, or a dialkoxyboryl group, and when two X exist, they may be the same as or different from each other.]

In view of the synthesis of the polymer compound which is the second compound of the present invention, X is preferably a chlorine atom, a bromine atom, or an iodine atom, more preferably a bromine atom or an iodine atom, and further preferably a bromine atom.

Since the compound represented by Formula (6) can be synthesized conveniently, X is also preferably a dihydroxyboryl group or a dialkoxyboryl group. The dialkoxyboryl group means a group in which two hydroxy groups of a dihydroxyboryl group and an alkyl group form an ester bond of boric acid via an oxygen atom. The dialkoxyboryl group is preferably a pinacolatoboryl group, a 1,3-propanediolateboryl group, or a dimethoxyboryl group. This is because the compound represented by Formula (6) is thermodynamically stable.

In view of the synthesis of the compound of the present invention, the compound represented by Formula (6) is preferably a compound represented by Formula (6').

[Chemical Formula 33]

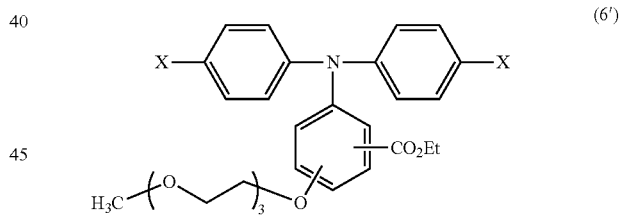

(6')

[In the formula, X means the same meaning as described above.]

In view of the synthesis of the compound of the present invention, the compound represented by Formula (6') is preferably a compound represented by Formula (6").

[Chemical Formula 34]

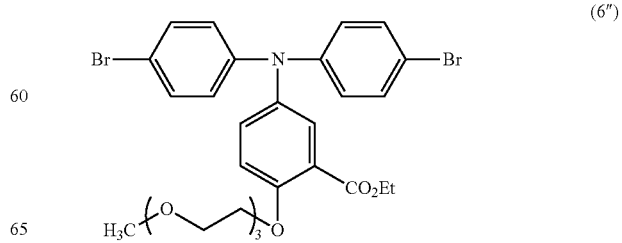

(6")

Examples of the low molecular compound which is the compound comprising the structure represented by Formula (5) and which is the second compound of the present invention include a compound represented by any one of Formulae 9-1 to 9-14.

Among these, since the light-emitting efficiency of an electroluminescent device using the first compound obtained from the second compound of the present invention, which is a precursor of the first compound, is higher, the low molecular compound is preferably a compound represented by any one of Formulae 9-1, 9-2, 9-3, 9-4, 9-7, 9-10, 9-11, 9-12, and 9-13, more preferably a compound represented by any one of Formulae 9-3, 9-4, 9-10, 9-11, and 9-12, and further preferably a compound represented by Formulae 9-3 or 9-12. The compound represented by any one of Formulae 9-1 to 9-14 may have substituent(s).

[Chemical Formula 35]

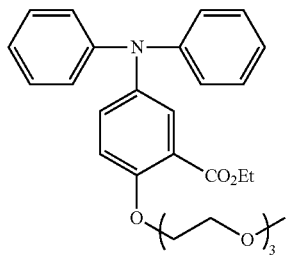
9-1

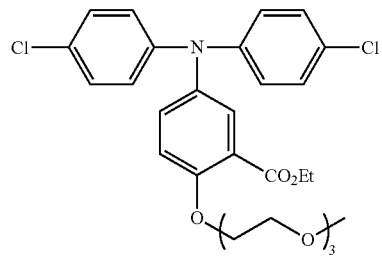
9-2

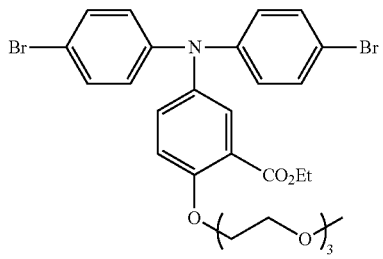
9-3

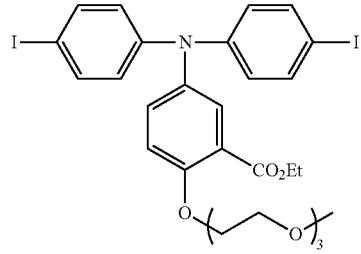
9-4

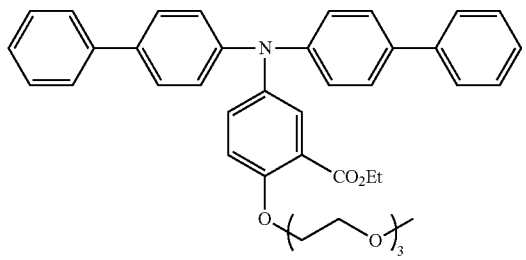
9-5

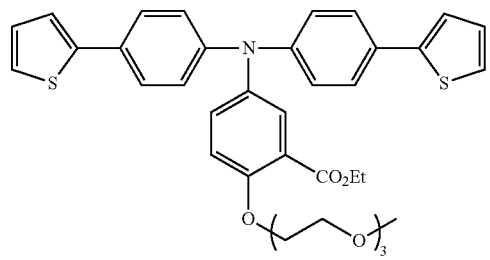
9-6

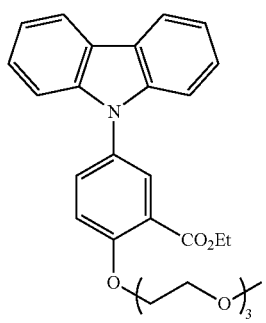
9-7

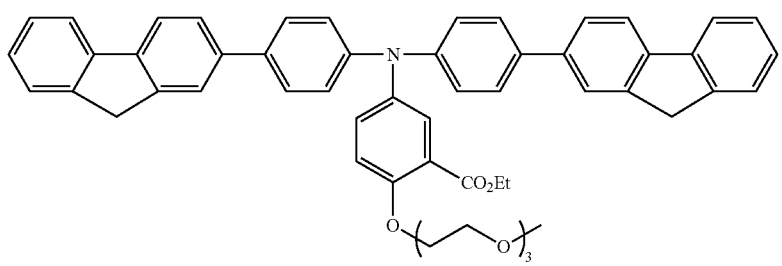
9-9

-continued

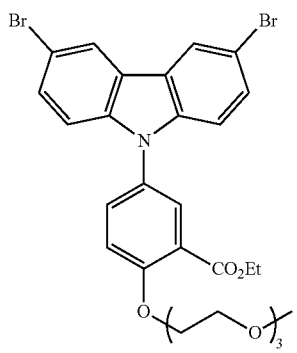
9-10

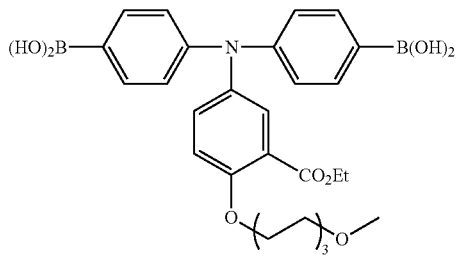
9-11

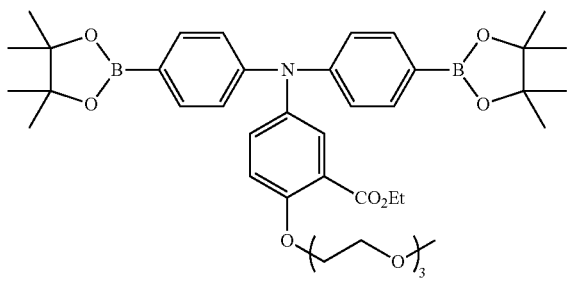
9-12

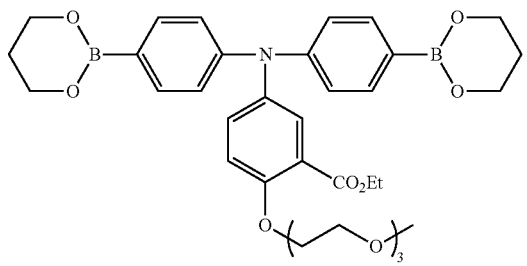
9-13

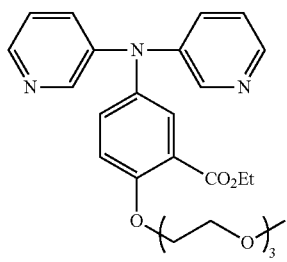
9-14

<Third Compound>

A compound represented by Formula (7) which is the third compound is particularly useful as a base material for the polymer compound which is the second compound of the present invention represented by Formulae (6), (6'), or (6"). Described below is the compound represented by Formula (7).

[Chemical Formula 36]

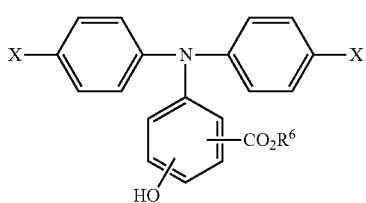
(7)

[In the formula, $R_6$ represents a monovalent organic group;

X represents a chlorine atom, a bromine atom, an iodine atom, a p-toluenesulfonate group, a trifluoromethanesulfonate group, a methanesulfonate group, a dihydroxyboryl group, or a dialkoxyboryl group, and the existing two X may be the same as or different from each other.]

The monovalent organic group represented by $R_6$ is the same as described above.

In view of the synthesis of the compound of the present invention, the compound represented by Formula (7) is preferably a compound represented by Formula (7').

[Chemical Formula 37]

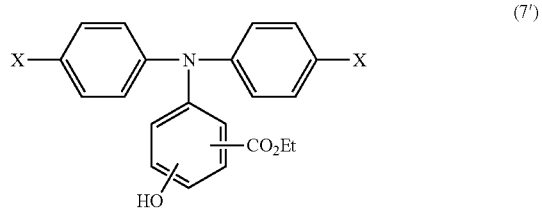
(7')

[In the formula, X means the same as described above.]

In view of the synthesis of the compound of the present invention, the compound represented by Formula (7') is preferably a compound represented by Formula (7").

[Chemical Formula 38]

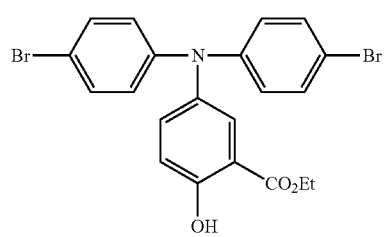
(7")

<Method for Manufacturing the Compound of the Present Invention>

Next, described is a method for manufacturing the first compound, the second compound, and the third compound of the present invention with an example given below.

The third compound of the present invention is manufactured as a precursor of the second compound of the present invention. For example, the third compound can be manufactured as follows.

At first, an amino group is introduced into an aromatic compound having both an alkoxy group and an ester group on its aromatic ring. After introducing an aryl group into the amino group, the above X is introduced into the aryl group. The alkoxy group and the ester group on the aromatic ring are converted into a hydroxy group and a carboxy group, respectively. The carboxy group is esterified, thereby enabling to manufacture the third compound.

Next, the second compound of the present invention is manufactured as a precursor of the first compound of the present invention.

When the second compound is a polymer compound, the second compound can be manufactured by a method that couples a compound manufactured from the third compound using a general organic synthesis reaction (e.g., a known condensation reaction, a nucleophilic substitution reaction, a rearrangement reaction, the Diels-Alder reaction, an aromatic electrophilic substitution reaction, or the like) and a compound having a plurality of leaving groups with a known condensation reaction, or a method that, using a known condensation reaction, couples compounds each other that manufactured from the third compound using a general organic synthesis reaction.

When the second compound is a low molecular compound, the second compound can be manufactured from the third compound using a reaction used in a general organic synthesis reaction. Examples of the reaction may include a known condensation reaction, a nucleophilic substitution reaction, a rearrangement reaction, the Diels-Alder reaction, an aromatic electrophilic substitution reaction, and the like.

The manufacture of the polymer compound which is the second compound of the present invention is preferably a method that couples a compound manufactured from the third compound using a general organic synthesis reaction (e.g., a known condensation reaction, a nucleophilic substitution reaction, a rearrangement reaction, the Diels-Alder reaction, an aromatic electrophilic substitution reaction, or the like) and a compound having a plurality of leaving groups with a known condensation reaction. Examples of the condensation reaction include a method that condenses by the Suzuki coupling reaction with a palladium (Pd) catalyst. Examples of the other condensation method include a method that condenses a Grignard reagent and an aryl halide by the Kumada-Tamao coupling reaction in the presence of a Ni catalyst, a method that condenses with a zero-valent nickel complex (Ni(0) complex), a method that condenses with an oxidizing agent such as $FeCl_3$, a method that oxidatively condenses electrochemically, and the like.

An organic solvent for use in the Suzuki coupling reaction is, which is dependent on the compounds used, generally preferably subjected to a sufficient deoxidization treatment in order to reduce the deterioration of a palladium catalyst, and the reaction preferably proceeds under an inert gas atmosphere.

Finally, the first compound of the present invention is manufactured from the second compound. The first compound of the present invention, in both cases of a polymer compound and a low molecular compound, can be manufactured by hydrolyzing the second compound of the present invention which is a precursor of the first compound.

Examples of the manufacture of the first compound of the present invention include a hydrolysis reaction using a metal hydroxide, an alkylammonium hydroxide, and the like. Preferably used is the hydrolysis reaction using a metal hydroxide since the hydrolysis reaction proceeds smoothly.

<Composition>

The composition of the present invention comprises the first compound of the present invention and at least one material selected from the group consisting of a hole transport material, an electron transport material, and a light-emitting material, as other components. Preferably used as the hole transport material, the electron transport material, and the light-emitting material are a material constituting a hole transport layer other than the first compound of the present invention, a material constituting an electron transport layer other than the first compound of the present invention, and a material constituting a light-emitting layer other than the first compound of the present invention, which are described below. In the composition of the present invention, the hole transport material, the electron transport material, and the light-emitting material may be used each singly, or two or more of them may be used in combination.

The content of the first compound of the present invention in the composition of the present invention is generally 0.0001 to 95 parts by weight with the total weight of the first compound of the present invention, the hole transport material, the electron transport material, and the light-emitting material as 100 parts by weight. In view of film formability, the content is preferably 0.0001 to 50 parts by weight.

The composition of the present invention also includes a composition comprising the first compound of the present invention and a solvent described below, as well as a composition comprising the first compound of the present invention, at least one material, as other components, selected from the group consisting of the hole transport material, the electron transport material and the light-emitting material, and the solvent described below.

The content of the solvent in the composition of the present invention is not particularly limited and may be determined in accordance with the type of the solvent, the film forming method for the first compound of the present invention, the molecular weight of the first compound of the present invention, or the like. For example, when a film is formed by an application method, in view of film formability, the content of the solvent in the composition of the present invention is preferably 1,000 to 1,000,000 parts by weight with respect to the total weight other than the solvent as 100 parts by weight.

<Stacked Structure>

The present invention provides a stacked structure comprising the first compound of the present invention or the composition thereof.

The stacked structure of the present invention comprises a first electrode, a second electrode, and a light-emitting layer or a charge separation layer provided between the first electrode and the second electrode. The first compound of the present invention or the composition thereof is comprised in the light-emitting layer or the charge separation layer, in a layer arranged between the light-emitting layer or the charge separation layer and the first electrode, or in a layer arranged between the light-emitting layer or the charge separation layer and the second electrode.

The stacked structure can be used for an electroluminescent device or a photoelectric conversion device. When the stacked structure is used for the electroluminescent device, the stacked structure is provided with the light-emitting layer. When the stacked structure is used for the photoelectric conversion device, the stacked structure is provided with the charge separation layer.

Since the compound used in the present invention has an excellent injectability or transportability of electron, when a layer comprising the compound is used for an electroluminescent device, the device having high light-emitting efficiency can be obtained. When a layer comprising the compound is used for a photoelectric conversion device, the cell having high conversion efficiency can be obtained.

<Electroluminescent Device>

The electroluminescent device using the stacked structure of the present invention comprises an anode, a cathode, and a light-emitting layer provided between the anode and the cathode and may further comprise an optional layer (a layer provided between the anode and the light-emitting layer, and/or a layer provided between the cathode and the light-emitting layer). The first compound of the present invention is comprised in the light-emitting layer or the optional layer, or is comprised in both the light-emitting layer and the optional layer. The electroluminescent device generally comprises a substrate.

One aspect of the electroluminescent device of the present invention includes providing the anode on the substrate, stacking the light-emitting layer thereon, and further stacking the cathode thereon. Another aspect includes providing the cathode on the substrate, stacking the light-emitting layer thereon, and further stacking the anode thereon. The electroluminescent device may comprise optional layers having other functions such as a passivation film, a buffer film, and a reflective film and is preferably isolated from the open air by being covered with a sealing film or a sealing substrate. The electroluminescent device of the present invention may be any type of what is called the bottom emission type that emits light from the substrate side, what is called the top emission type that emits light from the side opposite to the substrate, and the double-sided emission type.

As described above, the layer comprising the first compound of the present invention can be used for the light-emitting layer, the layer between the anode and the light-emitting layer, the layer between the cathode and the light-emitting layer, or the like in the electroluminescent device, and the layer can be functioned as the light-emitting layer, a charge injection layer, a charge transport layer, or the like.

Example of the method for forming the layer comprising the first compound of the present invention include a method for forming a film using a composition comprising a solvent in addition to the first compound of the present invention (hereinafter a solution).

The solvent for use in the film formation from such solution is preferably a "highly polar solvent" whose solubility parameter is 9.3 or more. This is because a stacked structure can be manufactured by applying a solution comprising the compound and the solvent onto a layer formed of a compound which is insoluble in the solvent. Specific examples of the highly polar solvent include water, methanol, ethanol, 2-propanol, 1-butanol, tert-butyl alcohol, acetonitrile, 1,2-ethanediol, N,N-dimethylformamide, dimethylsulfoxide, acetic acid, nitrobenzene, nitromethane, 1,2-dichloroethane, dichloromethane, chlorobenzene, bromobenzene, dioxane, propylene carbonate, pyridine, carbon disulfide, and a mixed solvent thereof. Among these, the highly polar solvent is preferably water, methanol, ethanol, 2-propanol, acetonitrile, 1,2-ethanediol, N,N-dimethylformamide, dimethylsulfoxide, or a mixed solvent thereof, more preferably methanol, ethanol, acetonitrile, N,N-dimethylformamide, dimethylsulfoxide, or a mixed solvent thereof, and particularly preferably methanol, N,N-dimethylformamide, or a mixed solvent thereof.

Examples of the film forming method from the solution include application methods such as spin coating, casting, microgravure coating, gravure coating, bar coating, roll coating, wire-bar coating, dip coating, slit coating, cap coating, spray coating, screen printing, flexo printing, offset printing, inkjet printing, and nozzle coating.

The film thickness of the layer comprising the first compound of the present invention may be appropriately selected so as to give suitable values of drive voltage and light-emitting efficiency, since its optimum value varies depending on the compound used. It is preferable that at least a thickness that produces no pinhole is needed. In view of decreasing the drive voltage of the electroluminescent device, the film thickness is preferably 1 nm to 1 µm, more preferably 2 nm to 500 nm, and further preferably 2 nm to 200 nm.

The electroluminescent device of the present invention, which comprises the anode, the cathode, and the light-emitting layer, may further comprise the optional layer as described above. For example, the element may comprise one or more of a hole injection layer and a hole transport layer between the anode and the light-emitting layer. When the hole injection layer is present, the device may comprise the hole transport layer between the light-emitting layer and the hole injection layer.

The device may comprise one or more of an electron injection layer and an electron transport layer between the cathode and the light-emitting layer. When the electron injection layer is present, the device may comprise the electron transport layer between the light-emitting layer and the electron injection layer. The layer comprising the first compound of the present invention may be used for the hole injection layer, the hole transport layer, the light-emitting layer, the electron injection layer, and the electron transport layer.

The anode supplies holes to the hole injection layer, the hole transport layer, the light-emitting layer, or the like, while the cathode supplies electrons to the electron injection layer, the electron transport layer, the light-emitting layer, or the like.

The light-emitting layer refers to, when applying an electric field, a layer having a function of receiving holes from a layer adjacent to the light-emitting layer on the anode side, a function of receiving electrons from a layer adjacent to the light-emitting layer on the cathode side, a function of moving the received charges (holes and electrons) through the force of the electric field, and a function of leading the recombination of the holes and the electrons to light emission.

The hole injection layer and the hole transport layer refer to a layer having any of a function of receiving holes from the anode, a function of transporting holes, a function of supplying holes to the light-emitting layer, and a function of blocking electrons injected from the cathode. The electron injection layer and the electron transport layer refer to a layer having any of a function of receiving electrons from the cathode, a function of transporting electrons, and a function of blocking holes injected from the anode. The electron transport layer and the hole transport layer are collectively called a charge transport layer. The electron injection layer and the hole injection layer are collectively called a charge injection layer.

In other words, the electroluminescent device of the present invention may have, for example, the following layer structure (a), or may have a layer structure remaining after omitting one or more layers of the hole injection layer, the hole transport layer, the electron transport layer, and the electron injection layer from the structure (a). The symbol "-" means that the layers are stacked adjacent to one another.

(a) Anode-Hole injection layer-Hole transport layer-Light-emitting layer-Electron transport layer-Electron injection layer-Cathode In the layer structure (a), the layer comprising the first compound of the present invention can be used as one or more layers selected from the group consisting of the hole injection layer, the hole transport layer, the light-emitting layer, the electron transport layer, and the electron injection layer.

In the layer structure (a), only when the layer comprising the first compound of the present invention is used as the light-emitting layer, the electroluminescent device of the present invention can have a layer structure (a') that omits all of the hole injection layer, the hole transport layer, the electron transport layer, and the electron injection layer.

(a') Anode-Light-emitting layer-Cathode

Specific preferable examples of the layer structure of the electroluminescent device of the present invention include the following ones. In the following layer structures, the layer comprising the first compound of the present invention can be used as one or more layers selected from the group consisting of the hole injection layer, the hole transport layer, the light-emitting layer, the electron transport layer, and the electron injection layer.

(b) Anode-Hole transport layer-Light-emitting layer-Cathode (c) Anode-Light-emitting layer-Electron transport layer-Cathode (d) Anode-Hole transport layer-Light-emitting layer-Electron transport layer-Cathode In the present invention, examples of the electroluminescent device provided with the charge injection layer (the electron injection layer or the hole injection layer) include an electroluminescent device provided with the electron injection layer adjacent to the cathode and an electroluminescent device provided with the hole injection layer adjacent to the anode. Specific examples include the following (e) to (p) structures.

(e) Anode-Hole injection layer-Light-emitting layer-Cathode (f) Anode-Light-emitting layer-Electron injection layer-Cathode (g) Anode-Hole injection layer-Light-emitting layer-Electron injection layer-Cathode (h) Anode-Hole injection layer-Hole transport layer-Light-emitting layer-Cathode (i) Anode-Hole transport layer-Light-emitting layer-Electron injection layer-Cathode (j) Anode-Hole injection layer-Hole transport layer-Light-emitting layer-Electron injection layer-Cathode (k) Anode-Hole injection layer-Light-emitting layer-Electron transport layer-Cathode (l) Anode-Light-emitting layer-Electron transport layer-Electron injection layer-Cathode (m) Anode-Hole injection layer-Light-emitting layer-Electron transport layer-Electron injection layer-Cathode (n) Anode-Hole injection layer-Hole transport layer-Light-emitting layer-Electron transport layer-Cathode (o) Anode-Hole transport layer-Light-emitting layer-Electron transport layer-Electron injection layer-Cathode (p) Anode-Hole injection layer-Hole transport layer-Light-emitting layer-Electron transport layer-Electron injection layer-Cathode The layer comprising the first compound of the present invention is preferably the electron injection layer and/or the electron transport layer.

In order to improve the adhesiveness with the electrodes and improve the injection of electric charges (i.e., holes or electrons) from the electrodes, the electroluminescent device of the present invention may further comprise an insulating layer adjacent to the electrodes. In order to improve the adhesiveness of interfaces, prevent mixing at the interfaces, or the like, a thin buffer layer is optionally imposed at the interface of the charge transport layer (the hole transport layer and the electron transport layer) or the light-emitting layer. The order, number, and thickness of the layers to be stacked can be appropriately used by considering the light-emitting efficiency and lifetime of the electroluminescent device.

Described next more specifically are materials of the layers constituting the electroluminescent device and manufacturing methods therefor.

<Substrate>

The substrate constituting the electroluminescent device of the present invention may be any substrate that generally forms an electrode and does not change when organic layers are formed, and examples of the substrate include glass, plastic, a polymer film, a metal film, a silicon substrate, and a stacked body of these. The substrate is commercially available or can be manufactured by a known method.

When the electroluminescent device of the present invention constitutes a pixel of a display device, the substrate may have thereon a circuit for driving the pixel or have a planarized film on this drive circuit. When the planarized film is arranged, the center line average roughness (Ra) of the planarized film preferably satisfies "Ra<10 nm." Ra can be measured based on JIS-B0601-2001 of Japanese Industrial Standards (JIS) with reference to JIS-B0651 to JIS-B0656, JIS-B0671-1, and the like.

<Anode>

In view of supplying holes to an organic semiconductor material used for the hole injection layer, the hole transport layer, the light-emitting layer, or the like, the surface of the anode constituting the electroluminescent device of the present invention at the light-emitting layer side preferably has a work function of 4.0 eV or more. For the material of the anode, may be used metals, alloys, electroconductive compounds such as metal oxides and metal sulfides, and mixtures thereof. Specific examples include electroconductive metal oxides such as tin oxide, zinc oxide, indium oxide, indium tin oxide (ITO), indium zinc oxide (IZO), and molybdenum oxide; metals such as gold, silver, chromium, and nickel; mixtures of these electroconductive metal oxides and metals; and the like.

The anode may have a single-layered structure composed of one or two or more of these materials or a multilayered structure composed of a plurality of layers having the same composition or different compositions. When it has a multilayered structure, it is more preferable to use a material having a work function of 4.0 eV or more on the outermost layer at the light-emitting layer side.

A method for manufacturing the anode is not particularly limited and any known methods can be used. Examples of the method include vacuum deposition, sputtering, ion plating, plating, and the like.

The film thickness of the anode is generally 10 nm to 10 μm and preferably 40 nm to 500 nm. In view of preventing faulty electric connection such as short circuit, the center line average roughness (Ra) of the surface of the anode at the light-emitting layer side preferably satisfies "Ra<10 nm" and more preferably "Ra<5 nm."

After being formed by the above method, the anode may be subjected to a surface treatment with, for example, a solution comprising an electron accepting compound such as UV ozone, a silane coupling agent, or 2,3,5,6-tetrafluoro-7,7,8,8-tetracyanoquinodimethane. This is because the surface treatment improves electric connection with an organic layer to be brought into contact with the anode.

When the anode is used as a light reflective electrode in the electroluminescent device of the present invention, the anode preferably has a multilayered structure composed of a combination of a light reflective layer made of a highly light reflective metal and a high work-function material layer comprising a material having a work function of 4.0 eV or more.

Specific examples of the structure of the anode are as follows. In order to obtain sufficient light reflectance, the film thickness of the highly light reflective metal layer such as Al, Ag, an Al alloy, a Ag alloy, and a Cr alloy is preferably 50 nm or more and more preferably 80 nm or more. The film thickness of the high work-function material layer such as ITO, IZO, and $MoO_3$ is generally in a range of 5 nm to 500 nm.

(i) Ag—$MoO_3$
(ii) (Ag—Pd—Cu alloy)-(ITO and/or IZO)
(iii) (Al—Nd alloy)-(ITO and/or IZO)
(iv) (Mo—Cr alloy)-(ITO and/or IZO)
(v) (Ag—Pd—Cu alloy)-(ITO and/or IZO)-$MoO_3$ <Hole Injection Layer>

In the electroluminescent device of the present invention, examples of the material constituting the hole injection layer other than the compound according to the present invention include carbazole derivatives, phenylenediamine derivatives, arylamine derivatives, starburst type amines, phthalocyanine derivatives, aromatic tertiary amine compounds, styrylamine compounds, polysilane-based compounds, poly(N-vinylcarbazole) derivatives, organic silane derivatives, and polymers comprising these.

Other examples include electroconductive metal oxides such as vanadium oxide, tantalum oxide, tungsten oxide, molybdenum oxide, ruthenium oxide, and aluminum oxide; electroconductive polymers and oligomers such as polyaniline, aniline-based copolymers, thiophene oligomers, and polythiophene; organic electroconductive materials such as poly(3,4-ethylenedioxythiophene)-polystyrenesulfonic acid, and polypyrrole and polymers comprising these; and amorphous carbon.

Also preferably used are acceptor organic compounds such as tetracyanoquinodimethane derivatives (e.g., 2,3,5,6-tetrafluoro-7,7,8,8-tetracyanoquinodimethane), 1,4-naphthoquinone derivatives, diphenoquinone derivatives, and polynitro compounds; and silane coupling agents such as octadecyltrimethoxysilane.

The above materials may be a single component or a composition composed of a plurality of components. The hole injection layer may be a single-layered structure composed of one or two or more of the above materials or a multilayered structure composed of a plurality of layers having the same composition or different compositions.

Various known methods can be used as a method for manufacturing the hole injection layer. For inorganic compound materials, examples of the method include vacuum deposition, sputtering, ion plating, and the like. For low molecular organic materials, examples of the method include vacuum deposition, transfer processes such as laser transfer and thermal transfer, a film forming method from a solution (also may be used is a mixed solution with a macromolecular binder described below), and the like. For macromolecular organic materials, examples of the method include a film forming method from a solution.

When the hole injection material is a low molecular material such as an arylamine derivative and a triphenyldiamine derivative, the hole injection layer can be manufactured using vacuum deposition.

The hole injection layer can also be formed using a mixed solution into which the low molecular hole injection material and a polymer compound binder are dispersed. The polymer compound binder to be mixed preferably does not extremely inhibit charge transport and preferably does not exhibit strong absorption of visible light. Specific examples of the polymer compound binder include poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethylacrylate, polymethylmethacrylate, polystyrene, polyvinylchloride, and polysiloxane.

The solvent for use in the film formation from a solution is not particularly limited so long as it dissolves the hole injection material. Examples of the solvent include water; chlorine-containing solvents such as chloroform, methylene chloride, and dichloroethane; ether solvents such as tetrahydrofuran; aromatic hydrocarbon solvents such as toluene and xylene; ketone solvents such as acetone and methyl ethyl ketone; and ester solvents such as ethyl acetate, butyl acetate, ethyl cellosolve acetate; and the like.

As the film forming method from a solution, can be used application methods, for example, coatings from a solution such as spin coating, casting, microgravure coating, gravure coating, bar coating, roll coating, wire-bar coating, dip coating, slit coating, capillary coating, spray coating, and nozzle coating; and printing methods such as gravure printing, screen printing, flexo printing, offset printing, reversal printing, and inkjet printing. In view of easiness of pattern formation, preferable are printing methods such as gravure printing, screen printing, flexo printing, offset printing, reversal printing, and inkjet printing, and nozzle coating.

When a compound layer such as the hole transport layer and the light-emitting layer is formed following the hole injection layer, and particularly when both layers are formed by an application method, a layered structure may not be formed, since the layer applied first dissolves in a solvent comprised in a solution for a layer applied later. In this case, a method that makes a lower layer insoluble in solvent may be employed. Examples of the method that makes the lower layer insoluble in solvent include a method that attaches cross-linking groups to a polymer compound and cross-links the polymer compound to be insolubilized, a method that mixes a low molecular compound having an aromatic-ring-containing cross-linking group represented by aromatic bisazide as a cross-linking agent and cross-links the low molecular compound to be insolubilized, a method that mixes a low molecular compound having an aromatic-ring-free cross-linking group represented by an acrylate group as a cross-linking agent and cross-links the low molecular compound to be insolubilized, a method that exposes the lower layer to ultraviolet light for cross-linking, thereby insolubilizing the lower layer in an organic solvent to be used in the manufacture of an upper layer; a method that heats the lower layer for cross-linking, thereby insolubilizing the lower layer in the organic solvent to be used in the manufacture of the upper layer; and the like. The heating temperature when heating the lower layer is generally about from 100° C. to 300° C. The heating time is generally about from 1 minute to 1 hour.

As another method for stacking the upper layer without dissolving the lower layer except cross-linking, there is a method that uses solutions different in polarity for the manufacture of the adjacent layers. For example, there is a method that uses for the lower layer a polymer compound which is soluble in a hydrophilic solvent represented by water, alcohol, N,N-dimethylformamide, dimethylsulfoxide, and N-methylpyrrolidone and is insoluble in an oleophilic solvent such as xylene and toluene and uses for the upper layer a polymer compound which is soluble in the oleophilic solvent, thereby preventing the lower layer from dissolving even by the application.

The film thickness of the hole injection layer, whose optimum value varies depending on the material used, may be selected so as to give suitable values of the drive voltage and light-emitting efficiency of the electroluminescent device. At least a thickness that produces no pinhole is needed. An excessively large thickness is unfavorable since the drive voltage of the device increases. Thus, the film thickness of the hole injection layer is, for example, 1 nm to 1 μm, preferably 2 nm to 500 nm, and further preferably 10 nm to 100 nm.

<Hole Transport Layer>

In the electroluminescent device of the present invention, examples of the material constituting the hole transport layer other than the first compound of the present invention include carbazole derivatives, pyrazoline derivatives, pyrazolone derivatives, phenylenediamine derivatives, arylamine derivatives, amino-substituted chalcone derivatives, hydrazone derivatives, stilbene derivatives, silazane derivatives, aromatic tertiary amine compounds, styrylamine compounds, polysilane-based compounds, poly(N-vinylcarbazole) derivatives, organic silane derivatives, and polymers comprising these structures. Other examples include electroconductive polymers and oligomers such as aniline-based copolymers, thiophene oligomers, and polythiophene; and organic electroconductive materials such as polypyrrole.

The above materials may be a single component or a composition composed of a plurality of components. The hole transport layer may be a single-layered structure composed of one or two or more of the above materials or a multilayered structure composed of a plurality of layers having the same composition or different compositions.

Specifically, compounds that can be used as the hole transport layer are disclosed in Japanese Patent Application Laid-open No. S63-70257, Japanese Patent Application Laid-open No. S63-175860, Japanese Patent Application Laid-open No. H02-135359, Japanese Patent Application Laid-open No. H02-135361, Japanese Patent Application Laid-open No. H02-209988, Japanese Patent Application Laid-open No. H03-37992, Japanese Patent Application Laid-open No. H03-152184, Japanese Patent Application Laid-open No. H05-263073, Japanese Patent Application Laid-open No. H06-1972, WO2005/52027, Japanese Patent Application Laid-open No. 2006-295203, or the like. Among these, preferably used is a polymer comprising a divalent aromatic amine residue as a repeating unit.

The polymer comprising a divalent aromatic amine as a repeating unit may comprise another repeating unit. Examples of the other repeating unit include arylene groups such as a phenylene group and a fluorenediyl group, and the like. More preferably, the polymer comprises a cross-linking group as a repeating unit.

A method for manufacturing the hole transport layer may be a similar method to those for the manufacture of the hole injection layer. Examples of the film forming method from a solution include the above application methods and printing methods such as spin coating, casting, bar coating, slit coating, spray coating, nozzle coating, gravure printing, screen printing, flexo printing, and inkjet printing. For a sublimation compound material, examples of the method include vacuum deposition, transfer processes, and the like. Examples of the solvent for use in the film formation from a solution include similar solvents to those exemplified in the film forming method for the hole injection layer described above.

When a compound layer such as the light-emitting layer is formed by an application method following the hole transport layer, when the lower layers dissolve in a solvent comprised in a solution for a layer applied later, examples of the method include similar methods to those exemplified in the film forming method for the hole injection method described above.

The film thickness of the hole transport layer, whose optimum value varies depending on the material used, may be selected so as to give suitable values of the drive voltage and light-emitting efficiency of the electroluminescent device. At least a thickness that produces no pinhole is needed. An excessively large thickness is unfavorable since the drive voltage of the device increases. Thus, the film thickness of the hole transport layer is, for example, 1 nm to 1 μm, preferably 2 nm to 500 nm, and further preferably 5 nm to 100 nm.

<Light-Emitting Layer>

When the light-emitting layer of the electroluminescent device of the present invention comprises a polymer compound, preferably can be used, as the polymer compound material, conjugated polymer compounds such as polyfluorene derivatives, polyparaphenylene vinylene derivatives, polyphenylene derivatives, polyparaphenylene derivatives, polythiophene derivatives, polydialkylfluorene, polyfluorenebenzothiadiazole, and polyalkylthiophene.

The light-emitting layer of the electroluminescent device of the present invention may be composed of a composition comprising a non-conjugated polymer compound and a light-emitting compound such as the organic dye and the metal complex. Examples of the non-conjugated polymer compound include polyethylene, polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resins, ketone resins, phenoxy resins, polyamide, ethyl cellulose, vinyl acetate, ABS resins, polyurethane, melamine resins, unsaturated polyester resins, alkyd resins, epoxy resins, silicone resins, and the like. The non-conjugated polymer compound may have, on the side chain thereof, a structure represented by one or more derivatives or compounds selected from the group consisting of carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne compounds, porphyrin compounds, and organic silane derivatives.

When the light-emitting layer of the electroluminescent device of the present invention comprises a low molecular compound, examples of the low molecular compound include low molecular dye compounds such as rubrene, perylene, 9,10-diphenylanthracene, tetraphenylbutadiene, Nile Red, coumarin 6, carbazole, and quinacridone; naphthalene derivatives; anthracene and derivatives thereof; perylene and derivatives thereof; dyes based on polymethine, xanthene, coumarin, cyanine, and indigo; metal complexes of 8-hydroxyquinoline and derivatives thereof; metal complexes of phthalocyanine and derivatives thereof; aromatic amines; tetraphenylcyclopentadiene and derivatives thereof; tetraphenylbutadiene and derivatives thereof; and the like.

When the light-emitting layer of the electroluminescent device of the present invention comprises a metal complex emitting phosphorescence, examples of the metal complex include tris(2-phenylpyridine)iridium, thienylpyridine ligand-containing iridium complexes, phenylquinoline ligand-containing iridium complexes, triazacyclononane skeleton-containing terbium complexes, and the like.

Specific examples of the polymer compound for use in the light-emitting layer include polyfluorene and derivatives and copolymers thereof, polyarylene and derivatives and copolymers thereof, polyarylene vinylene and derivatives and copolymers thereof, and aromatic amines and derivatives and copolymers thereof disclosed in, for example, WO97/09394, WO98/27136, WO99/54385, WO00/22027, WO01/19834, GB2340304A, GB2348316, U.S. Pat. No. 573,636, U.S. Pat. No. 5,741,921, U.S. Pat. No. 5,777,070, EP0707020, Japanese Patent Application Laid-open No. H09-111233, Japanese Patent Application Laid-open No. H10-324870, Japanese Patent Application Laid-open No. 2000-80167, Japanese Patent Application Laid-open No. 2001-123156, Japanese Patent Application Laid-open No. 2004-168999, Japanese Patent Application Laid-open No. 2007-162009, and "Development and Constituent Materials of Organic EL Device (CMC Publishing Co., Ltd., published in 2006)," or the like. Specific examples of the low molecular compound for use in the light-emitting layer include compounds disclosed in Japanese Patent Application Laid-open No. S57-51781, "Organic Thin Film Work Function Data Collection [2nd Edition] (CMC Publishing Co., Ltd., published in 2006)," and "Development and Constituent Materials of Organic EL Device (CMC Publishing Co., Ltd., published in 2006)," or the like.

The polymer compound and the low molecular compound may be a single component or a composition composed of a plurality of components. The light-emitting layer may be a single-layered structure composed of one or two or more of the polymer compound and the low molecular compound, or a multilayered structure composed of a plurality of layers having the same composition or different compositions.

A method for forming the light-emitting layer may be a similar method to those for the manufacture of the hole injection layer. Examples of the film forming method from a solution include application methods and printing methods such as spin coating, casting, bar coating, slit coating, spray coating, nozzle coating, gravure printing, screen printing, flexo printing, and inkjet printing. For a sublimation compound material, examples of the method include vacuum deposition, transfer processes, or the like. Examples of the solvent for use in the film formation from a solution include those exemplified in the film forming method for the hole injection layer.

In the formation of a compound layer such as the electron transport layer by an application method following the light-emitting layer, when the lower layers dissolve in a solvent comprised in a solution for a layer applied later, the lower layers can be made solvent-insoluble by a similar method to those exemplified in the film forming method for the hole injection layer.

The film thickness of the light-emitting layer, whose optimum value varies depending on the material used, may be selected so as to give suitable values of the drive voltage and light-emitting efficiency of the electroluminescent device. At least a thickness that produces no pinhole is needed. An excessively large thickness is unfavorable since the drive voltage of the device increases. Thus, the film thickness of the light-emitting layer is, for example, 5 nm to 1 μm, preferably 10 nm to 500 nm, and further preferably 30 nm to 200 nm.

<Electron Transport Layer>

In the electroluminescent device of the present invention, known materials can be used as the material constituting the electron transport layer other than the first compound of the present invention. Examples of the material include triazole derivatives, oxazole derivatives, oxadiazole derivatives, imidazole derivatives, fluorenone derivatives, benzoquinone and derivatives thereof, naphtoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, anthraquinodimethane derivatives, distyrylpyrazine derivatives, aromatic tetracarboxylic acid anhydrides of naphthalene, perylene, and the like, metal complexes of 8-quinolinol derivatives, various metal complexes represented by metal complexes having benzoxazole or benzothiazole as a ligand, metal complexes of 8-hydroxyquinoline and derivatives thereof, polyquinoline and derivatives thereof, polyquinoxaline and derivatives thereof, and polyfluorene and derivatives thereof.

Among these, preferable are triazole derivatives, oxadiazole derivatives, benzoquinone and derivatives thereof, anthraquinone and derivatives thereof, 8-hydroxyquinoline derivatives and metal complexes thereof, polyquinoline and derivatives thereof, polyquinoxaline and derivatives thereof, and polyfluorene and derivatives thereof.

The above materials may be a single component or a composition composed of a plurality of components. The electron transport layer may be a single-layered structure composed of one or two or more of the above materials or a multilayered structure composed of a plurality of layers having the same composition or different compositions.

A method for manufacturing the hole transport layer may be a similar method to those for the manufacture of the hole injection layer. Examples of the film forming method from a solution include application methods and printing methods such as spin coating, casting, bar coating, slit coating, spray coating, nozzle coating, gravure printing, screen printing, flexo printing, and inkjet printing. For a sublimation compound material, examples of the method include vacuum deposition, transfer processes, and the like.

Examples of the solvent for use in the film formation from a solution include similar solvents to those exemplified in the film forming method for the hole injection layer described above.

In the formation of a compound layer such as the electron injection layer by an application method following the electron transport layer, when the lower layers dissolve in a solvent comprised in a solution for a layer applied later, adopted may be a similar method to those exemplified in the film forming method for the hole injection layer as described above.

The film thickness of the electron transport layer, whose optimum value varies depending on the material used, may be selected so as to give suitable values of the drive voltage and light-emitting efficiency of the electroluminescent device. At least a thickness that produces no pinhole is needed. An excessively large thickness is unfavorable since the drive voltage of the device increases. Thus, the film thickness of the electron transport layer is, for example, 1 nm to 1 µm, preferably 2 nm to 500 nm, and further preferably 5 nm to 100 nm.

<Electron Injection Layer>

In the electroluminescent device of the present invention, known materials can be used as the material constituting the electron injection layer other than the first compound of the present invention. Examples of the material include triazole derivatives, oxazole derivatives, oxadiazole derivatives, imidazole derivatives, fluorenone derivatives, benzoquinone and derivatives thereof, naphtoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, anthraquinodimethane derivatives, distyrylpyrazine derivatives; aromatic tetracarboxylic acid anhydrides of naphthalene, perylene, and the like; metal complexes of 8-quinolinol derivatives; and various metal complexes represented by metal complexes having benzoxazole or benzothiazole as a ligand.

The above materials may be a single component or a composition composed of a plurality of components. The electron injection layer may be a single-layered structure composed of one or two or more of the above materials or a multilayered structure composed of a plurality of layers having the same composition or different compositions.

A method for manufacturing the electron injection layer is not limited and may be a similar method to those for the manufacture of the hole injection layer. Examples of the film forming method from a solution include application methods and printing methods such as spin coating, casting, bar coating, slit coating, spray coating, nozzle coating, gravure printing, screen printing, flexo printing, and inkjet printing. For a sublimation compound material, examples of the method include vacuum deposition, transfer processes, or the like.

Examples of the solvent for use in the film formation from a solution include similar solvents to those exemplified in the film forming method for the hole injection layer described above.

The film thickness of the electron injection layer, whose optimum value varies depending on the material used, may be selected so as to give suitable values of the drive voltage and light-emitting efficiency of the electroluminescent device. At least a thickness that produces no pinhole is needed. An excessively large thickness is unfavorable since the drive voltage of the device increases. Thus, the film thickness of the electron injection layer is, for example, 1 nm to 1 µm, preferably 2 nm to 500 nm, and further preferably 5 nm to 100 nm.

<Cathode>

In the electroluminescent device of the present invention, the cathode is adjacent to the light-emitting layer, the electron transport layer, or the electron injection layer and has a function of supplying electrons to these layers. The cathode may be a single-layered structure composed of a single material or a plurality of materials or may be a multilayered structure composed of a plurality of layers. When it is a multilayered structure, it is preferably a two-layer structure composed of a first cathode layer and a cover cathode layer, or a three-layer structure composed of a first cathode layer, a second cathode layer and a cover cathode layer. The first cathode layer refers to a layer present closest to the light-emitting layer among the cathodes. The cover cathode layer refers to a layer that covers the first cathode layer when it has the two-layer structure and to a layer that covers the first cathode layer and the second cathode layer when it has the three-layer structure. In view of electron supplying ability, the material of the first cathode layer preferably has a work function of 3.5 eV or less. Also preferable as the first cathode material are metal oxides, metal fluorides, metal carbonates, metal composite oxides, or the like having a work function of 3.5 eV or less. Preferably used as the material of the cover cathode layer is metals, metal oxides, or the like having low resistivity and high corrosion resistance against water.

Specific examples of the first cathode layer material include one or more materials selected from the group consisting of alkali metals and alkaline-earth metals, alloys containing one or more of the metals, oxides, halides, carbonates, and composite oxides of the metals, combinations thereof, and the like.

Examples of the alkali metal include lithium, sodium, potassium, rubidium, cesium, and the like. Examples of the oxide, halide, carbonate, and composite oxide of the alkali metal include lithium oxide, sodium oxide, potassium oxide, rubidium oxide, cesium oxide, lithium fluoride, sodium fluoride, potassium fluoride, rubidium fluoride, cesium fluoride, lithium carbonate, sodium carbonate, potassium carbonate, rubidium carbonate, cesium carbonate, potassium molybdate, potassium titanate, potassium tungstate, and cesium molybdate, and the like.

Examples of the alkaline-earth metal include magnesium, calcium, strontium, barium, and the like. Examples of the oxide, halide, carbonate, and composite oxide of the alkaline-earth metal include magnesium oxide, calcium oxide, strontium oxide, barium oxide, magnesium fluoride, calcium fluoride, strontium fluoride, barium fluoride, magnesium carbonate, calcium carbonate, strontium carbonate, barium carbonate, barium molybdate, barium tungstate, and the like.

Examples of the alloy containing one or more metals selected from the group consisting of alkali metals and alkaline-earth metals include a Li—Al alloy, a Mg—Ag alloy, an Al—Ba alloy, a Mg—Ba alloy, a Ba—Ag alloy, and a Ca—Bi—Pb—Sn alloy.

Examples of the material of the second cathode layer include similar materials to the materials of the first cathode layer. A composition comprising any of the materials exemplified as the first cathode layer and any of the materials exemplified as the materials constituting the electron injection layer can also be used as the first cathode layer.

Specific examples of the cover cathode layer include low-resistance metals such as gold, silver, copper, aluminum, chromium, tin, lead, nickel, and titanium; alloys containing these metals; electroconductive metal oxides such as tin oxide, zinc oxide, indium oxide, indium tin oxide (ITO), indium zinc oxide (IZO), and molybdenum oxide; mixtures of any of the electroconductive metal oxides and any of the metals; electroconductive carbon such as graphene, fullerene, and carbon nano tubes; and the like.

Specific examples of the cathode having a multilayered structure include the two-layer structure (the first cathode layer/the cover cathode layer) such as Mg/Al, Ca/Al, Ba/Al, NaF/Al, KF/Al, RbF/Al, CsF/Al, Na$_2$CO$_3$/Al, K$_2$CO$_3$/Al, and Cs$_2$CO$_3$/Al; and the three-layer structure (the first cathode layer/the second cathode layer/the cover cathode layer) such as LiF/Ca/Al, NaF/Ca/Al, KF/Ca/Al, RbF/Ca/Al, CsF/Ca/Al, Ba/Al/Ag, KF/Al/Ag, KF/Ca/Ag, and K$_2$CO$_3$/Ca/Ag. The symbol "/" means that the layers are adjacent to each other. The material of the second cathode layer preferably has a reduction action on the material of the first cathode layer.

The presence or absence and degree of the reduction action between materials can be estimated, for example, from bond dissociation energy ($D_0$) between compounds. That is, in the reduction reaction of the material constituting the first cathode layer with the material constituting the second cathode layer, when they are a combination of materials to provide positive bond dissociation energy, the material of the second cathode layer has a reduction action on the material of the first cathode layer. For the bond dissociation energy, "Handbook on Electrochemistry, 5th edition (Maruzen Co., Ltd., published in 2000)" and "Thermodynamic Database MALT (Kagaku Gijutsu-Sha, published in 1992)" can be referred to.

Various known methods can be used as a method for manufacturing the cathode, and examples of the method include vacuum deposition, sputtering, ion plating, and the like.

When used as the cathode is a metal, a metal oxide, a metal fluoride, or a metal carbonate, vacuum deposition is frequently used. When used as the cathode is a high boiling-point metal oxide, a metal composite oxide, an electroconductive metal oxide represented by indium tin (ITO), sputtering and ion plating are frequently used.

When a film of a composition with a different material is formed, co-evaporation, sputtering, ion plating, and the like are frequently used. In particular, when a film of a composition of a low molecular organic compound and a metal, an oxide, a fluoride, or a carbonate of a metal is formed, co-evaporation is preferable.

The film thickness of the cathode, whose optimum value varies depending on the material used and the layer structure, may be selected so as to give suitable values of the drive voltage, light-emitting efficiency, and lifetime of the electroluminescent device. Generally, the film thickness of the first cathode layer is in a range of 0.5 nm to 20 nm, and the film thickness of the cover cathode layer is in the range of 10 nm to 1 μm. For example, when Ba or Ca is used as the first cathode layer, and when Al is used as the cover cathode layer, it is preferable that the film thickness of Ba or Ca is 2 nm to 10 nm and that the film thickness of Al is 10 nm to 500 nm. When NaF or KF is used as the first cathode layer, and when Al is used as the cover cathode layer, it is preferable that the film thickness of NaF or KF is 1 nm to 8 nm and that the film thickness of Al is 10 nm to 500 nm.

In the electroluminescent device of the present invention, when the cathode is used as an optically transparent electrode, the visible light transmittance of the cover cathode layer is preferably 40% or more and more preferably 50% or more. The visible light transmittance is achieved by using a transparent electroconductive metal oxide such as indium tin oxide (ITO), indium zinc oxide (IZO), and molybdenum oxide as the cover cathode layer material. The visible light transmittance is also achieved by making the film thickness of the cover cathode layer 30 nm or less, the cover cathode layer using a low-resistance metal such as gold, silver, copper, aluminum, chromium, tin, and lead, or an alloy containing these metals. For example, a cathode structure employing Ba of 5 nm as the first cathode layer and Ag of 15 nm as the cover cathode layer achieves a visible light transmittance of 50% or more.

In order to improve the visible light transmittance, an antireflective layer may be arranged on the cover cathode layer. A material that can be used as the antireflective layer preferably has a refractive index of about 1.8 to 3.0, and examples of the material include ZnS, ZnSe, $WO_3$, and the like. The film thickness of the antireflective layer, which varies depending on the combination of materials, is generally in a range of 10 nm to 150 nm. For example, the visible light transmittance is improved by about 10% by stacking $WO_3$ with a thickness of 21 nm as the antireflective layer on the cathode structure having Ba of 5 nm as the first cathode layer and Ag of 15 nm as the cover cathode layer.

<Insulating Layer>

An optional insulating layer having a film thickness of 5 nm or less that the electroluminescent device of the present invention has functions of improving adhesiveness with an electrode, improving injection of charges (i.e., holes or electrons) from the electrode, preventing mixture with an adjacent layer, and the like. Examples of the insulating layer material include metal fluorides, metal oxides, organic insulating materials (polymethylmethacrylate or the like), and the like. Examples of the electroluminescent device provided with the insulating layer having a film thickness of 5 nm or less include one provided with the insulating layer having a film thickness of 5 nm or less adjacent to the cathode and one provided with the insulating layer having a film thickness of 5 nm or less adjacent to the anode.

The electroluminescent device of the present invention can be manufactured by, for example, successively stacking layers on a substrate. Specifically, the electroluminescent device can be manufactured by providing the anode on the substrate, stacking layers such as the hole injection layer and the hole transport layer where necessary, providing thereon the light-emitting layer, providing thereon layers such as the electron transport layer and the electron injection layer, where necessary, and further providing thereon the cathode.

A display apparatus can be manufactured using the electroluminescent device of the present invention. The display apparatus has the electroluminescent device as one pixel unit. The manner of arranging the pixel units, which is not particularly limited, can be arrangement which is generally adopted in display devices such as televisions, in which many pixels are arranged on a common substrate. In the device of the present invention, the pixels arranged on the substrate can be formed within a pixel area defined by a bank, where necessary.

The device may further comprise a sealing member on the side opposite to the substrate across the light-emitting layer and the like, where necessary. The device may comprise optional components for constituting the display device such as filters including a color filter or a fluorescence conversion filter and circuits and wiring needed for driving the pixels, where necessary.

<Photoelectric Conversion Device>

The photoelectric conversion device using the stacked structure of the present invention comprises a cathode, an anode, and a charge separation layer arranged between the cathode and the anode and may further include optional layers (a layer provided between the cathode and the charge separation layer and/or a layer provided between the anode and the charge separation layer).

The first compound of the present invention is comprised in the charge separation layer or the optional layer, or is comprised in both the charge separation layer and the optional layer.

The charge separation layer of the photoelectric conversion device of the present invention comprises an electron donating compound and an electron accepting compound. Examples of the electron donating compound include conjugated polymer compounds and specifically include polymer compounds comprising a thiophenediyl group, polymer compounds comprising a fluorenediyl group, and the like. Examples of the electron accepting compound include fullerene, fullerene derivatives, and the like.

The photoelectric conversion device of the present invention is generally manufactured on a supporting substrate. The supporting substrate is not particularly limited in its material so long as it does not inhibit the characteristics as an organic photoelectric conversion device. Glass substrates, flexible film substrates, and plastic substrates may be used.

The photoelectric conversion device of the present invention can be manufactured by known methods, for example, a method described in "Synth. Met., 102, 982 (1999)" or a method described in "Science, 270, 1789 (1995)."

EXAMPLES

Described below are examples for describing the present invention in more detail. The present invention is not limited to these examples.

Structural analysis for synthesized compounds was performed by $^1$H NMR analysis using a 300 MHz NMR spectrometer manufactured by Varian, Inc. with a sample dissolved in a deuterated solvent that can dissolve the sample.

Synthesis Example 1

Synthesis of Compound (A-1)

After replacing under a nitrogen gas atmosphere within a reaction vessel, 2,7-dibromo-9-fluorenone (92.0 g, 272 mmol) and diethyl ether (3.7 L) were mixed and cooled to 0° C. Thereto was added dropwise a 1 mol/L diethyl ether solution of methylmagnesium iodide (0.545 L, 545 mmol), and the mixture was stirred for 3 hours. To the resultant reaction mixture was added an aqueous ammonium chloride solution and removed the aqueous layer, and the resultant organic layer was dried over sodium sulfate anhydride and was concentrated in vacuo. The resultant crude product was purified by silica gel column chromatography to give a target compound (A-1) (92.81 g, 262 mmol, yield: 96%).

$^1$H NMR (400 MHz, CDCl$_3$, rt): δ (ppm)=1.71 (1H), 2.02 (3H), 7.45-7.68 (4H), 7.68 (2H).

[Chemical Formula 39]

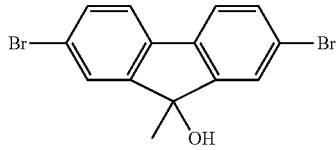

(A-1)

Synthesis Example 2

Synthesis of Compound (B-1)

After replacing under a nitrogen gas atmosphere within a reaction vessel, the compound (A-1) (83.0 g, 234 mmol), p-toluene sulfonate monohydrate (4.49 g, 23.6 mmol), and chloroform (2.5 L) were mixed and refluxed for 1 hour, and to the resultant reaction mixture was added an aqueous ammonium chloride solution and removed the aqueous layer. The resultant organic layer was dried over sodium sulfate anhydride and was concentrated in vacuo to give a target compound (B-1) (73.6 g, 219 mmol, yield: 93%).

$^1$H NMR (400 MHz, CDCl$_3$, rt): δ (ppm)=6.10 (2H), 7.48-7.53 (4H), 7.83 (2H).

[Chemical Formula 40]

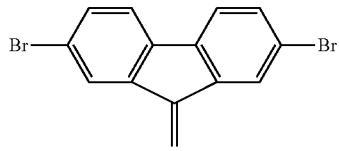

(B-1)

Synthesis Example 3

Synthesis of Compound (C-1)

After replacing under a nitrogen gas atmosphere within a reaction vessel, mixed were the compound (B-1) (70.0 g, 208 mmol), ethyl salicylate (104 g, 625 mmol), mercaptoacetic acid (4.20 g, 45.6 mmol), and methanesulfonic acid (1,214 g), and the mixture was stirred at 70° C. for 8 hours. The resultant reaction mixture was added dropwise to iced water, and the precipitated solid was collected by filtration and washed with methanol. The resultant crude product was purified by silica gel column chromatography to give a target compound (C-1) (52.14 g, 104 mmol, yield: 50%).

$^1$H NMR (400 MHz, CDCl$_3$, rt): δ (ppm)=1.44 (3H), 1.84 (1H), 4.44 (2H), 6.76 (2H), 7.29 (2H), 7.48 (2H), 7.60 (2H), 7.88 (1H), 10.8 (1H).

[Chemical Formula 41]

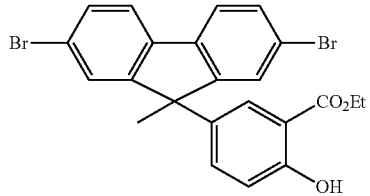

(C-1)

Synthesis Example 4

Synthesis of Compound (D-1)

After replacing under a nitrogen gas atmosphere within a reaction vessel, mixed were the compound (C-1) (41.2 g, 82.0 mmol), 2-[2-(2-methoxyethoxy)ethoxy]-ethyl-p-toluene sulfonate (75.8 g, 238 mmol), dimethylformamide (214 g), potassium carbonate (54.4 g, 394 mmol), and 1,4,7,10,13,16-hexaoxacyclooctadecane (also referred to as "18-crown-6") (4.68 g, 18 mmol), and the mixture was stirred at 105° C. for 2 hours. The resultant reaction mixture was added to water and extracted with ethyl acetate. The resultant organic layer was dried over anhydrous sodium sulfate and concentrated in vacuo, and the resultant crude product was purified by silica gel column chromatography to give a target compound (D-1) (40.2 g, 62.0 mmol, yield: 76%).

$^1$H NMR (400 MHz, CDCl$_3$, rt): δ (ppm)=1.37 (3H), 1.84 (3H), 3.36 (3H), 3.53 (2H), 3.58-3.79 (6H), 3.73 (2H), 4.12 (2H), 4.34 (2H), 6.80 (1H), 6.90 (1H), 7.28 (2H), 7.48 (2H), 7.58 (2H), 7.70 (1H).

[Chemical Formula 42]

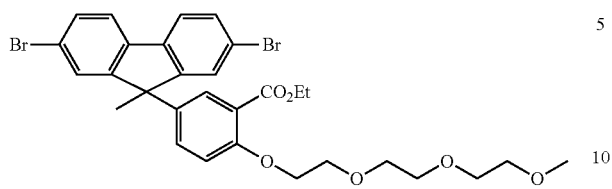

(D-1)

Synthesis Example 5

Synthesis of Compound (E-1)

After replacing under a nitrogen gas atmosphere within a reaction vessel, mixed were the compound (D-1) (28.4 g, 43.8 mmol), bis(pinacolato)diboron (24.30 g, 95.7 mol), [1,1'-bis(diphenylphosphino)ferrocene]palladium (II) dichloride with one molecule of dichloromethane (0.35 g, 0.4 mmol), 1,1'-bis(diphenylphosphino)ferrocene (0.24 g, 0.4 mmol), potassium acetate (25.60 g, 260 mmol), and 1,4-dioxane (480 mL), and the mixture was stirred at 120° C. for 17 hours. The resultant reaction mixture was filtrated and washed with ethyl acetate. The resultant filtrate was concentrated in vacuo, purified by silica gel column chromatography, and then purified by recrystallization to give a target compound (E-1) (18.22 g, 24.5 mmol, yield: 56%).

$^1$H NMR (400 MHz, CDCl$_3$, rt): δ (ppm)=1.30-1.47 (27H), 1.88 (3H), 3.35 (3H), 3.53 (2H), 3.60-3.69 (4H), 3.73 (2H), 3.84 (2H), 4.10 (2H), 4.34 (2H), 6.74 (1H), 6.87 (1H), 7.58 (2H), 7.72-7.89 (5H).

[Chemical Formula 43]

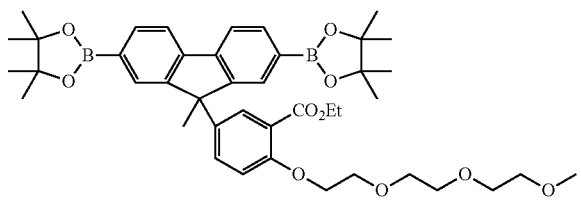

(E-1)

Synthesis Example 6

Synthesis of Compound (A-2)

After replacing under a nitrogen gas atmosphere within a reaction vessel, 2,7-dibromo-9-fluorenone (82.3 g, 244 mmol) and tetrahydrofuran (3.8 L) were mixed and cooled to 0° C. To the mixture was added dropwise a 1 mol/L tetrahydrofuran solution of iso-butylmagnesium bromide (0.475 L, 475 mmol), and the mixture was stirred for 1 hour. To the resultant reaction mixture was added an aqueous ammonium chloride solution and removed the aqueous layer, and the resultant organic layer was dried over sodium sulfate anhydride and was concentrated in vacuo. The resultant crude product was purified by silica gel column chromatography to give a target compound (A-2) (51.9 g, 131 mmol, yield: 54%).

$^1$H NMR (400 MHz, CDCl$_3$, rt): δ (ppm)=0.60 (6H), 1.17 (1H), 2.04 (1H), 2.09 (2H), 7.43-7.51 (4H), 7.62 (2H).

[Chemical Formula 44]

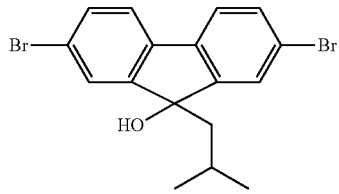

(A-2)

Synthesis Example 7

Synthesis of Compound (B-2)

After replacing under a nitrogen gas atmosphere within a reaction vessel, the compound (A-2) (49.6 g, 125 mmol), methane toluenesulfonic acid (99.1 g, 1,032 mmol), and chloroform (0.51 L) were mixed and refluxed for 1 hour. To the resultant reaction mixture was added an aqueous ammonium chloride and removed the aqueous layer. The resultant organic layer was dried over sodium sulfate anhydride and was concentrated in vacuo to give a target compound (B-2) (36.4 g, 96.3 mmol, yield: 77%)

$^1$H NMR (400 MHz, CDCl$_3$, rt): δ (ppm)=1.27 (6H), 3.41 (1H), 6.60 (1H), 7.45-7.60 (4H), 7.80 (1H), 7.97 (1H).

[Chemical Formula 45]

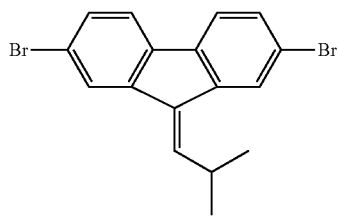

(B-2)

Synthesis Example 8

Synthesis of Compound (C-2)

After replacing under a nitrogen gas atmosphere within a reaction vessel, mixed were the compound (3-2) (36.4 g, 96.3 mmol), ethyl salicylate (32.0 g, 193 mmol), mercaptoacetic acid (1.86 g, 20.2 mmol), and methanesulfonic acid (465 g), and the mixture was stirred at 70° C. for 6 hours. The resultant reaction mixture was added dropwise to iced water, and the precipitated solid was collected by filtration and washed with methanol. The resultant crude product was purified by silica gel column chromatography to give a target compound (C-2) (39.6 g, 72.8 mmol, yield: 75.6%).

$^1$H NMR (400 MHz, CDCl$_3$, rt): δ (ppm)=0.53 (6H), 0.98 (1H), 1.44 (3H), 2.41 (2H), 4.44 (2H), 6.74 (1H), 6.80 (1H), 7.30 (2H), 7.47 (2H), 7.60 (2H), 7.84 (1H), 10.8 (1H).

[Chemical Formula 46]

(C-2)

Synthesis Example 9

Synthesis of Compound (D-2)

After replacing under a nitrogen gas atmosphere within a reaction vessel, mixed were the compound (C-2) (39.6 g, 72.8 mmol), 2-[2-(2-methoxyethoxy)ethoxy]-ethyl-p-toluene sulfonate (67.1 g, 210 mmol), dimethylformamide (198 g), potassium carbonate (48.2 g, 349 mmol), and 1,4,7,10,13,16-hexaoxacyclooctadecane (also referred to as "18-crown-6") (3.82 g, 14.5 mmol), and the mixture was stirred at 105° C. for 1 hour. The resultant reaction mixture was added to water and extracted with ethyl acetate. The resultant organic layer was dried over anhydrous sodium sulfate and concentrated in vacuo, and the resultant crude product was purified by silica gel column chromatography to give a target compound (D-2) (47.4 g, 68.6 mmol, yield: 94%).

$^1$H NMR (400 MHz, CDCl$_3$, rt): δ (ppm)=0.51 (2H), 1.00 (1H), 1.38 (3H), 2.44 (2H), 3.36 (3H), 3.53 (2H), 3.58-3.73 (6H), 3.72 (2H), 4.13 (2H), 4.34 (2H), 6.75 (1H), 6.85 (1H), 7.32 (2H), 7.48 (2H), 7.58 (2H), 7.70 (1H).

[Chemical Formula 47]

(D-2)

Synthesis Example 10

Synthesis of Compound (E-2)

After replacing under a nitrogen gas atmosphere within a reaction vessel, mixed were the compound (D-2) (18.0 g, 26.1 mmol), bis(pinacolato)diboron (14.7 g, 57.4 mol), [1,1'-bis(diphenylphosphino)ferrocene]palladium (II) dichloride with one molecule of dichloromethane (0.21 g, 0.26 mmol), 1,1'-bis(diphenylphosphino)ferrocene (0.14 g, 0.26 mmol), potassium acetate (15.4 g, 156 mmol), and 1,4-dioxane (290 mL), and the mixture was stirred at 120° C. for 24 hours. The resultant reaction mixture was filtrated and washed with ethyl acetate. The resultant filtrate was concentrated in vacuo, purified by silica gel column chromatography, and then purified by recrystallization to give a target compound (E-2) (11.6 g, 14.8 mmol, yield: 57%).

$^1$H NMR (400 MHz, CDCl$_3$, rt): δ (ppm)=0.44 (6H), 0.99 (1H), 1.30-1.43 (27H), 2.55 (2H), 3.35 (3H), 3.53 (2H), 3.60-3.69 (4H), 3.74 (2H), 3.85 (2H), 4.08 (2H), 4.34 (2H), 6.70 (1H), 6.79 (1H), 7.56 (2H), 7.75-7.83 (5H).

[Chemical Formula 48]

(E-2)

Synthesis Example 11

Synthesis of Compound (F)

A compound F was synthesized in accordance with a method described in "Tetrahedron, 2008, 64, 2772-2782."

$^1$H NMR (400 MHz, CDCl$_3$, rt): δ (ppm)=3.45 (2H), 3.83 (3H), 3.89 (3H), 6.82 (2H), 7.16 (1H).

[Chemical Formula 49]

(F)

Synthesis Example 12

Synthesis of Compound (G)

After replacing under a nitrogen gas atmosphere within a reaction vessel, mixed were the compound (F) (14.2 g, 78.3 mmol), bromobenzene (36.9 g, 23.5 mol), palladium diacetate (0.878 g, 3.91 mmol), tri-tert-butylphosphine (2.38 g, 11.7 mmol), cesium acetate (63.7 g, 196 mmol), and toluene (142 mL), and the mixture was stirred while being refluxed for 8 hours. The resultant reaction mixture was diluted with dichloromethane, filtered, and washed. The resultant filtrate was concentrated in vacuo, purified by silica gel column chromatography, and then purified by recrystallization to give a target compound (G) (18.7 g, 56.1 mmol, yield: 72%).

$^1$H NMR (400 MHz, CDCl$_3$, rt): δ (ppm)=3.83 (3H), 3.90 (3H), 6.85 (1H), 7.02-7.04 (6H), 7.21-7.25 (5H), 7.57 (1H).

[Chemical Formula 50]

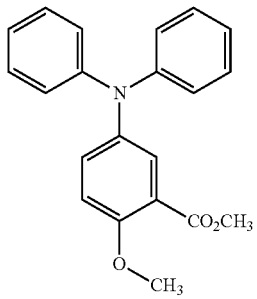

(G)

Synthesis Example 13

Synthesis of Compound (H)

After replacing under a nitrogen gas atmosphere within a reaction vessel, the compound (G) (8.81 g, 26.4 mmol), N-bromosuccinimide (9.54 g, 53.6 mol), and chloroform (340 mL) were mixed and stirred for 1 hour at room temperature. To the resultant reaction mixture was added a 5 wt % aqueous sodium thiosulfate solution (40 mL). Separation and washing, drying over sodium sulfate, and concentration in vacuo gave a compound (H) (13.9 g) as a crude product.

Similarly, after replacing under a nitrogen gas atmosphere within a reaction vessel, the compound (G) (9.49 g, 28.5 mmol), N-bromosuccinimide (10.3 g, 58.1 mol), and chloroform (390 mL) were mixed and stirred for 1 hour at room temperature. To the resultant reaction mixture was added a 5 wt % aqueous sodium thiosulfate solution (40 mL). Separation and washing, drying over sodium sulfate, and concentration in vacuo gave a compound (H) (15.0 g) as a crude product.

The resultant crude product (28.9 g in total) was dispersed into hexane (600 mL) and then stirred and filtrated to give a target compound (H) (26.0 g, 52.9 mmol, yield: 94%).

$^1$H NMR (400 MHz, CDCl$_3$, rt): δ (ppm)=3.84 (3H), 3.90 (3H), 6.87-7.52 (11H).

[Chemical Formula 51]

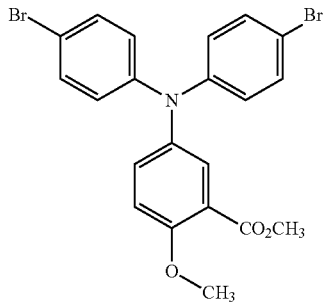

(H)

Synthesis Example 14

Synthesis of Compound (I)

After replacing under a nitrogen gas atmosphere within a reaction vessel, the compound (H) (24.3 g, 49.5 mmol), a 1 mol/L dichloromethane solution of boron tribromide (149 ml), and chloroform (366 mL) were mixed and stirred for 24 hours at room temperature. The resultant reaction mixture was diluted with water, separated and washed, dried over sodium sulfate, and concentrated in vacuo. The resultant residue was purified by silica gel column chromatography to give a target compound (I) (11.5 g, 24.8 mmol, yield: 49%).

$^1$H NMR (400 MHz, CDCl$_3$, rt): δ (ppm)=6.88-7.61 (12H), 10.3 (1H).

[Chemical Formula 52]

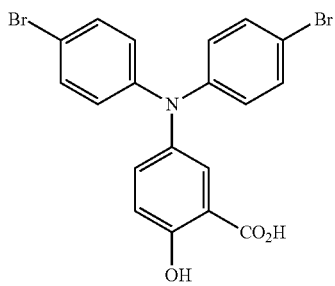

(I)

Example 1

Synthesis of Compound (J)

The compound (I) (10.2 g, 22.0 mmol), ethanol (1,500 mL), and concentrated sulfuric acid (12.7 mL) were mixed and stirred for 72 hours at 100° C. in the presence of 4 Å molecular sieves. Sodium sulfate (500 g) was added to the resultant reaction mixture, which was filtrated, washed, and then concentrated in vacuo to be about 200 mL. The resultant residue was purified by silica gel column chromatography to give a target compound (J) (9.20 g, 18.7 mmol, yield: 85%).

$^1$H NMR (400 MHz, CDCl$_3$, rt): δ (ppm)=1.36 (3H), 4.38 (2H), 6.87 (4H), 6.92 (1H), 7.20-7.33 (5H), 7.58 (1H), 10.8 (1H).

[Chemical Formula 53]

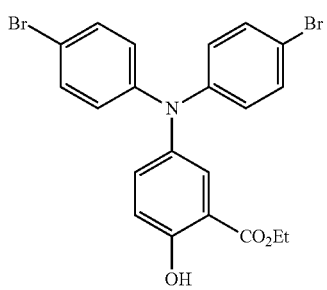

(J)

Example 2

Synthesis of Compound (K)

Mixed were the compound (J) (9.20 g, 18.7 mmol), 3,6,9-trioxadecyl p-toluenesulfonate (8.95 g, 28.1 mmol), potassium carbonate (5.18 g, 37.5 mmol), and N,N-dimethylformamide (184 g), and the mixture was stirred for 24 hours at 80° C. The resultant reaction mixture was diluted with ethyl acetate, separated and washed, and dried over sodium sulfate. The resultant solution was filtrated, and the resultant filtrate was concentrated in vacuo. The resultant residue was purified by silica gel column chromatography to give a target compound (K) (11.5 g, 18.0 mmol, yield: 96%).

$^1$H NMR (400 MHz, CDCl$_3$, rt): δ (ppm)=1.34 (3H), 3.38 (3H), 3.55 (2H), 3.65 (4H), 3.69 (2H), 3.76 (2H), 4.18 (2H), 4.30 (2H), 6.89 (5H), 7.11 (1H), 7.31 (4H), 7.48 (1H).

[Chemical Formula 54]

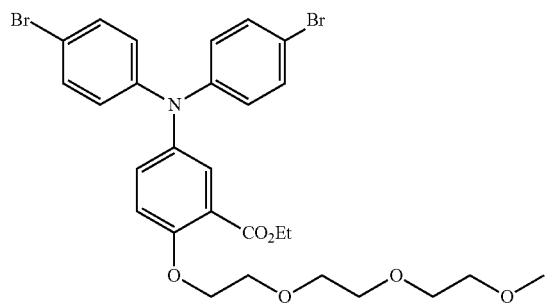

(K)

the compound (K) (20.8 mg, 0.0327 mmol), trioctylmethylammonium chloride (trade name Aliquot 336 manufactured by Aldrich) (5.50 mg, 0.0136 mmol), bis(triphenylphosphine)dichloropalladium (1.30 mg, 1.85 μmol), a 17.5 wt % aqueous sodium carbonate solution (10 mL), and toluene (20 mL), and the mixture was stirred at 105° C. for 7 and a half hours.

Thereto were added bis(triphenylphosphine)dichloropalladium (1.30 mg, 1.85 μmol), a 17.5 wt % aqueous sodium carbonate solution (1.5 mL), and phenylboronic acid (39.9 mg, 0.326 mmol), and the mixture was stirred for 6 hours. Thereto were added sodium diethyldithiocarbamate trihydrate (0.490 g) and water (10 mL), and the mixture was stirred at 80° C. for 2 hours. The resultant mixture was added dropwise to methanol, and the precipitate was collected by filtration and dried. The resultant solid was dissolved in chloroform and purified by alumina and silica gel chromatography, and the eluate was concentrated and dried. The resultant concentrate was dissolved in toluene and added dropwise to methanol. The precipitate was collected by filtration and dried to give 342 mg of a polymer compound (L-1). The weight average molecular weight calculated by polystyrene conversion of the polymer compound (L-1) was $3.3 \times 10^4$. The polymer compound (L-1) is estimated to be a polymer compound having the following constitutional unit and molar ratio from the charging ratio of the monomers.

[Chemical Formula 55]

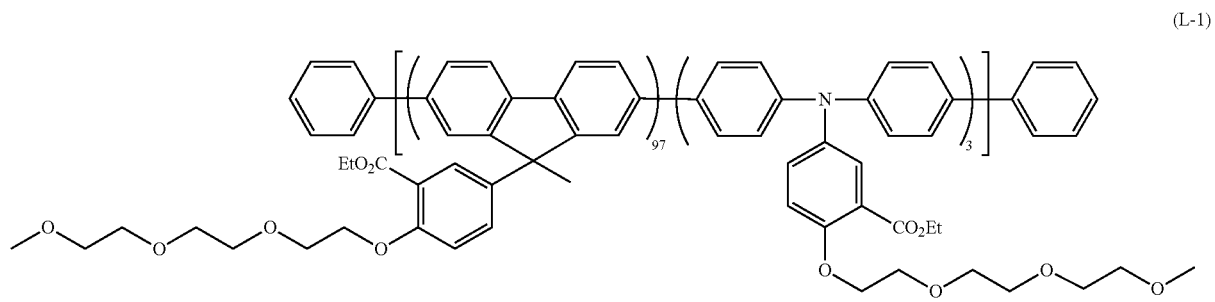

(L-1)

Example 3

Synthesis of Polymer Compound (L-1)

Into a flask were placed the compound (D-1) (331 mg, 0.510 mmol), the compound (E-1) (362 mg, 0.488 mmol),

Example 4

Synthesis of Polymer Compound (M-1)

Into a flask were placed the polymer compound (L-1) (150 mg), cesium hydroxide monohydrate (103 mg, 0.612 mmol), tetrahydrofuran (20 mL), methanol (10 mL), and water (1.2 mL), and the mixture was stirred at 65° C. After stirring for 2 hours, methanol (20 mL) was added, and the mixture was stirred for additional 2 hours. The resultant solution was concentrated, dried, dissolved in methanol, and added dropwise to 2-propanol. The resultant precipitate was collected by filtration and dried to give 142 mg of a polymer compound (M-1). The polymer compound (M-1) is estimated to be a polymer compound having the following constitutional unit and molar ratio.

additional 1 hour, the compound (E-2) (15 mg) was added, and the mixture was stirred for 1 hour.

Thereto were added bis(triphenylphosphine)dichloropalladium (1.68 mg, 2.39 μmol), a 17.5 wt % aqueous sodium carbonate solution (2.3 mL), and phenylboronic acid (39.0 mg, 0.320 mmol), and the mixture was stirred for 6 hours. Thereto were added sodium diethyldithiocarbamate trihy-

[Chemical Formula 56]

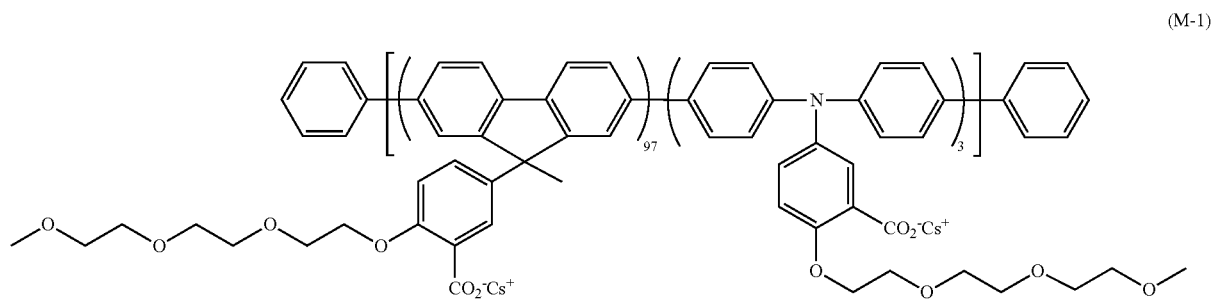

(M-1)

Example 5

Synthesis of Polymer Compound (L-2)

Into a flask were placed the compound (D-2) (439 mg, 0.560 mmol), the compound (E-2) (484 mg, 0.704 mmol), the compound (K) (61.2 mg, 0.0960 mmol), trioctylmethylammonium chloride (trade name Aliquot 336 manufactured by Aldrich) (8.10 mg, 0.0200 mmol), bis(triphenylphosphine)dichloropalladium (1.68 mg, 2.39 μmol), a 17.5 wt % aqueous sodium carbonate solution (10 mL), and toluene (20 mL), and the mixture was stirred at 105° C. After stirring for 2 hours, the compound (E-2) (55 mg) was added. After stirring for additional two hours, the compound (E-2) (50 mg) was added. After stirring for additional 1 hour, the compound (E-2) (20 mg) was added. After stirring for drate (0.720 g) and water (14 mL), and the mixture was stirred at 80° C. for 2 hours. The resultant mixture was added dropwise to methanol, and the precipitate was collected by filtration and dried. The resultant solid was dissolved in chloroform and purified by alumina and silica gel chromatography, and the eluate was concentrated and dried. The resultant concentrate was dissolved in toluene and added dropwise to methanol. The precipitate was collected by filtration and dried to give 392 mg of a polymer compound (L-2). The weight average molecular weight calculated by polystyrene conversion of the polymer compound (L-2) was $3.9 \times 10^4$. The polymer compound (L-2) is estimated to be a polymer compound having the following constitutional unit and molar ratio from the charging ratio of the monomers.

[Chemical Formula 57]

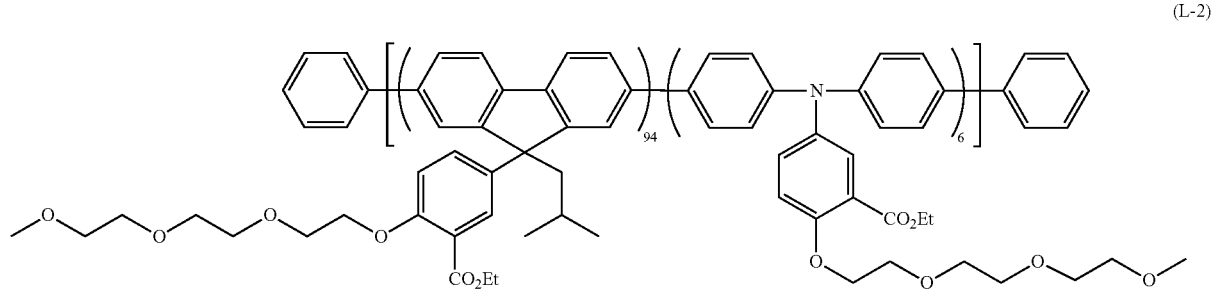

(L-2)

Example 6

Synthesis of Polymer Compound (M-2)

Into a flask were placed the polymer compound (L-2) (200 mg), cesium hydroxide monohydrate (126 mg, 0.751 mmol), tetrahydrofuran (4.0 mL), methanol (6.0 mL), and water (0.3 mL), and the mixture was stirred at 65° C. After stirring for 4 hours, the resultant solution was concentrated and then washed with water to give 211 mg of a polymer compound (M-2). The polymer compound (M-1) is estimated to be a polymer compound having the following constitutional unit and molar ratio.

Example 8

When methanol was added to the polymer compound (M-1) so as to be a 0.32 wt % methanol solution and the solution was stirred, the polymer compound (M-1) was completely dissolved.

Example 9

When methanol was added to the polymer compound (M-2) so as to be a 0.32 wt % methanol solution and the solution was stirred, the polymer compound (M-2) was completely dissolved.

[Chemical Formula 58]

(M-2)

Example 7

Synthesis of Polymer Compound (M-3)

Into a flask were placed the polymer compound (L-2) (150 mg), lithium hydroxide monohydrate (59.1 mg, 0.751 mmol), tetrahydrofuran (10 mL), methanol (10 mL), and water (0.3 mL), and the mixture was stirred at 65° C. After stirring for 4 hours, the resultant solution was concentrated, dried, dissolved in methanol, and added dropwise to 2-propanol. The resultant precipitate was collected by filtration and dried to give 136 mg of a polymer compound (M-3). The polymer compound (M-3) is estimated to be a polymer compound having the following constitutional unit and molar ratio.

Example 10

When methanol was added to the polymer compound (M-3) so as to be a 0.32 wt % methanol solution and the solution was stirred, the polymer compound (M-3) was completely dissolved.

Example 11

Synthesis of Polymer Compound (N)

After replacing under an argon gas atmosphere within a reaction vessel, mixed were the compound (K) (638 mg), methanol (20 mL), cesium hydroxide monohydrate (168 mg), and water (1.20 mL), and the mixture was stirred at 69°

[Chemical Formula 59]

(M-3)

C. for 2 hours. The resultant reaction mixture was concentrated and dried to give 624 mg of a compound (N).

$^1$H NMR (300 MHz, CD$_3$OD, rt): δ (ppm)=3.35 (3H), 3.52-3.57 (2H), 3.59-3.67 (4H), 3.68-3.73 (2H), 3.80-3.87 (2H), 4.12-4.21 (2H), 6.88-6.94 (4H), 6.96-7.02 (2H), 7.10 (1H), 7.30-7.38 (4H).

[Chemical Formula 60]

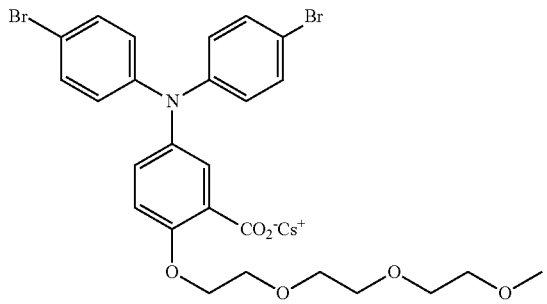

(N)

Example 12

When methanol was added to the compound (N) so as to be a 0.32 wt % methanol solution and the solution was stirred, the compound (N) was completely dissolved. The result is listed in Table 1.

Comparative Example 1

When a compound (O) was synthesized in accordance with a method described in "Non Patent Literature 1." When methanol was added to the compound (O) so as to be a 0.32 wt % methanol solution and the solution was stirred, the compound (O) was not completely dissolved. The result is listed in Table 1.

[Chemical Formula 61]

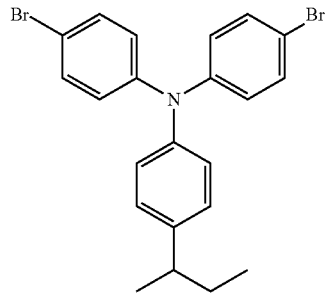

(O)

TABLE 1

| | Compound | Methanol 0.32 wt % |
|---|---|---|
| Example 12 | Compound (N) | Completely dissolved |
| Comparative Example 1 | Compound (O) | Not completely dissolved |

Table 1 reveals that the solubility of the compound (N) in methanol was higher than that of the compound (O).

Thus, the first compound of the present invention has high solubility in methanol, which is a highly polar solvent.

Example 13

Manufacture of Electroluminescent Device 1

Onto an ITO anode (thickness: 45 nm), which had been patterned by film formation on the surface of a glass substrate, a solution of a hole injection material was applied to form a hole injection layer with a film thickness of 60 nm by spin coating.

The substrate formed with the hole injection layer was heated at 200° C. for 10 minutes under a nitrogen atmosphere, then naturally cooled down to room temperature to give the substrate formed with the hole injection layer.

Used as the solution of a hole injection layer was PEDOT: PSS solution (poly(3,4-ethylenedioxythiophene).poly(styrenesulfonate), trade name: Baytron) manufactured by Starck Vitec Co.

Next, a hole-transporting macromolecular material and xylene were mixed to give a composition for forming a hole transport layer comprising the hole-transporting macromolecular material in an amount of 0.7% by weight.

The hole-transporting macromolecular material was synthesized by the following method.

After replacing under an inert gas atmosphere within a reaction vessel, mixed were 2,7-dibromo-9,9-di(octyl)fluorene (1.4 g), 2,7-bis(4,4,5,5-tetramethyl-1,3,2-dioxaborolan-2-yl)-9,9-di(octyl)fluorene (6.4 g), N,N-bis(4-bromophenyl)-N',N'-bis(4-butylphenyl)-1, 4-phenylenediamine (4.1 g), bis(4-bromophenyl)benzocyclobuteneamine (0.6 g), tetraethylammonium hydroxide (1.7 g), palladium acetate (4.5 mg), tri(2-methoxyphenyl)phosphine (0.03 g), and toluene (100 mL), and the resultant mixture was stirred at 100° C. for 2 hours. Phenylboronic acid (0.06 g) was added thereto, and the resultant mixture was stirred for 10 hours. The mixture was left to be cooled, and the aqueous layer was removed therefrom. Thereto was added an aqueous sodium diethyldithiocarbamate solution. After stirring, the aqueous layer was removed therefrom, and the resultant organic layer was washed with water and an aqueous acetic acid solution. The resultant organic layer was poured into methanol to precipitate a solid. The precipitated solid was filtered, dissolved in toluene again, and passed through a silica gel and alumina column. The eluted toluene solution containing a solid was collected and poured into methanol to precipitate the solid. The precipitated solid was filtered and was dried in vacuo at 50° C. to give 12.1 g of a hole-transporting macromolecular material. The weight average molecular weight calculated by polystyrene conversion of the hole-transporting macromolecular material was 3.0×10$^5$.

The hole-transporting macromolecular material is a copolymer containing a constitutional unit represented by the following formula:

[Chemical Formula 62]

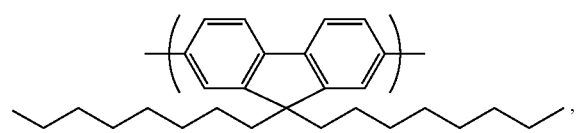

a constitutional unit represented by the following formula:

[Chemical Formula 63]

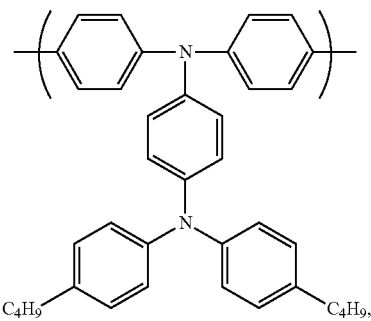

and
a constitutional unit represented by the following formula:

[Chemical Formula 64]

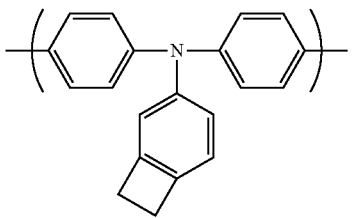

with a molar ratio of 62.5:30:7.5 (a theoretical value from the charging amounts of the base materials).

The composition for forming a hole transport layer was applied onto the hole injection layer of the substrate formed with the hole injection layer obtained as described above to form a hole transport layer by spin coating so as to give a film thickness of 20 nm. The substrate formed with this hole transport layer was heated under a nitrogen gas atmosphere at 180° C. for 60 minutes to make the hole transport layer insolubilize, and naturally cooled down to room temperature to give the substrate formed with the hole transport layer.

Next, a light-emitting macromolecular material and xylene were mixed to give a composition for forming a light-emitting layer containing the light-emitting macromolecular material in an amount of 1.4% by weight.

The light-emitting macromolecular material was synthesized by the following method.

After replacing under an inert gas atmosphere within a reaction vessel, mixed were 2,7-dibromo-9,9-di(octyl)fluorene (9.0 g), N,N'-bis(4-bromophenyl)-N,N'-bis(4-tert-butyl-2,6-dimethylphenyl)1,4-phenylenediamine (1.3 g), 2,7-bis(4,4,5,5-tetramethyl-1,3,2-dioxaborolan-2-yl)-9,9-di(4-hexylphenyl)fluorene (13.4 g), tetraethylammonium hydroxide (43.0 g), palladium acetate (8 mg), tri(2-methoxyphenyl)phosphine (0.05 g), and toluene (200 mL), and the resultant mixture was stirred for 8 hours with heating at 90° C. Phenylboronic acid (0.22 g) was added thereto, and the resultant mixture was stirred for 14 hours. The mixture was left to be cooled, and the aqueous layer was removed therefrom. Thereto was added an aqueous sodium diethyldithiocarbamate solution. After stirring, the aqueous layer was removed therefrom, and the resultant organic layer was washed with water and an aqueous acetic acid solution. The resultant organic layer was poured into methanol to precipitate a solid. The precipitated solid was filtered, dissolved in toluene again, and passed through a silica gel and alumina column. The eluted toluene solution containing a solid was collected and poured into methanol to precipitate the solid. The precipitated solid was filtered and was dried in vacuo at 50° C. to give a light-emitting macromolecular material (12.5 g). The weight average molecular weight calculated by polystyrene conversion was $3.1 \times 10^5$.

The light-emitting macromolecular material is a copolymer containing a constitutional unit represented by the following formula:

[Chemical Formula 65]

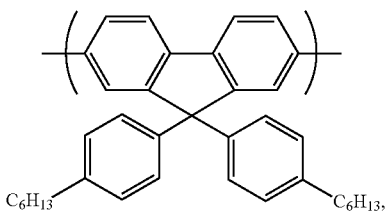

a constitutional unit represented by the following formula:

[Chemical Formula 66]

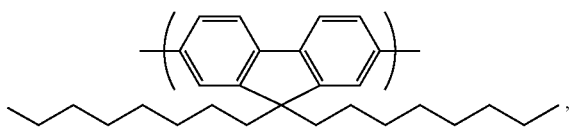

and
a constitutional unit represented by the following formula:

[Chemical Formula 67]

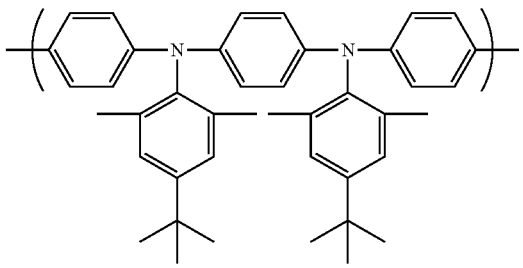

with a molar ratio of 50:45:5 (a theoretical value from the charging amounts of the base materials).

The composition for forming a light-emitting layer was applied onto the hole transport layer of the substrate formed with the hole transport layer obtained as described above to give a light-emitting layer by spin coating so as to give a film thickness of 80 nm. The substrate formed with this light-emitting layer was heated under a nitrogen gas atmosphere at 130° C. for 10 minutes and naturally cooled down to room temperature to give the substrate formed with the light-emitting layer.

Methanol and the compound (M-1) were mixed to give a composition with a content of the compound (M-1) of 0.25% by weight.

The composition was applied onto the light-emitting layer of the substrate formed with the light-emitting layer obtained as described above to form an electron injection layer by spin coating so as to give a film thickness of 10 nm. The substrate formed with this electron injection layer was heated under a nitrogen gas atmosphere at 130° C. for 15 minutes and naturally cooled down to room temperature to give the substrate formed with the electron injection layer.

The substrate formed with the electron injection layer obtained as described above was put into a vacuum apparatus, and Al with a thickness of 80 nm was formed by vacuum deposition to form a cathode, thus forming a stacked structure 1.

The stacked structure 1 obtained as described above was taken out of the vacuum apparatus and sealed with sealing glass and two-liquid mixed type epoxy resin under a nitrogen gas atmosphere to manufacture an electroluminescent device 1.

Example 14

Manufacture of Electroluminescent Device 2

An electroluminescent device 2 was manufactured in the same manner as Example 13 except that the compound (M-2) was used in place of the compound (M-1).

Example 15

Manufacture of Electroluminescent Device 3

An electroluminescent device 3 was manufactured in the same manner as Example 13 except that the compound (M-3) was used in place of the compound (M-1).

Comparative Example 2

Manufacture of Electroluminescent Device 4

An electroluminescent device 4 was manufactured in the same manner as Example 13 except that the layer containing the compound (M-1) was not formed.

A forward voltage of 10 V was applied to the electroluminescent devices 1 to 4 obtained as described above to measure light-emitting brightness and light-emitting efficiency. The results are listed in Table 1.

TABLE 2

| | Organic compound in electron injection layer | Light-emitting brightness (cd/cm$^2$) | Light-emitting efficiency (cd/A) |
|---|---|---|---|
| Example 13 (Electroluminescent device 1) | Compound (M-1) | 2,900 | 5.3 |
| Example 14 (Electroluminescent device 2) | Compound (M-2) | 1,800 | 5.8 |
| Example 15 (Electroluminescent device 3) | Compound (M-3) | 4,700 | 5.7 |
| Comparative Example 2 (Electroluminescent device 4) | Absent | 6.4 | 0.14 |

Table 2 reveals that the electroluminescent device containing the compound of the present invention has remarkably excellent light-emitting efficiency as compared to the electroluminescent device that does not contain the compound of the present invention.

The invention claimed is:

1. A polymer compound comprising a structure represented by Formula (1) as a constitutional unit:

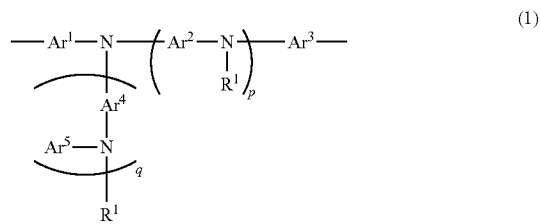

wherein:
$Ar^1$, $Ar^2$, $Ar^3$, and $Ar^4$ each independently represent a divalent aromatic group optionally having substituent(s) and may be bonded to each other to form a ring, when more than one $Ar^2$ is present, such $Ar^2$s may be the same as or different from each other, and when more than one $Ar^4$ is present, such $Ar^4$s may be the same as or different from each other;

$Ar^5$ represents a monovalent aromatic group optionally having substituent(s), and when more than one $Ar^5$ is present, such $Ar^5$s may be the same as or different from each other;

p and q each independently represent an integer of 0 or more; and $R^1$ represents a monovalent group represented by Formula (2), and when more than one $R^1$ is present, such $R^1$s may be the same as or different from each other:

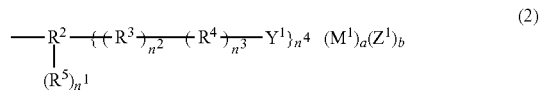

wherein:
$R^2$ represents a $(1+n^1+n^4)$-valent aromatic group optionally having substituent(s);

$R^3$ represents a divalent organic group optionally having substituent(s);

$R^4$ represents a divalent organic group comprising a structure which is capable of interacting with a cation through chelation, and when more than one $R^4$ is present, such $R^4$s may be bonded to each other to form a ring;

$R^5$ is an optionally substituted monovalent organic group remaining after removing one hydrogen atom from a compound represented by a formula selected from the group consisting of formulas 3-1 to 3-4 and 3-6 to 3-27, and when more than one $R^5$ is present, such $R^5$s may be bonded to each other to form a ring:

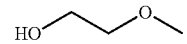

3-1

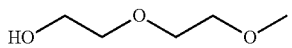

3-2

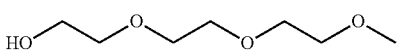

3-3

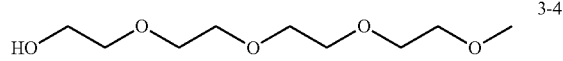

3-4

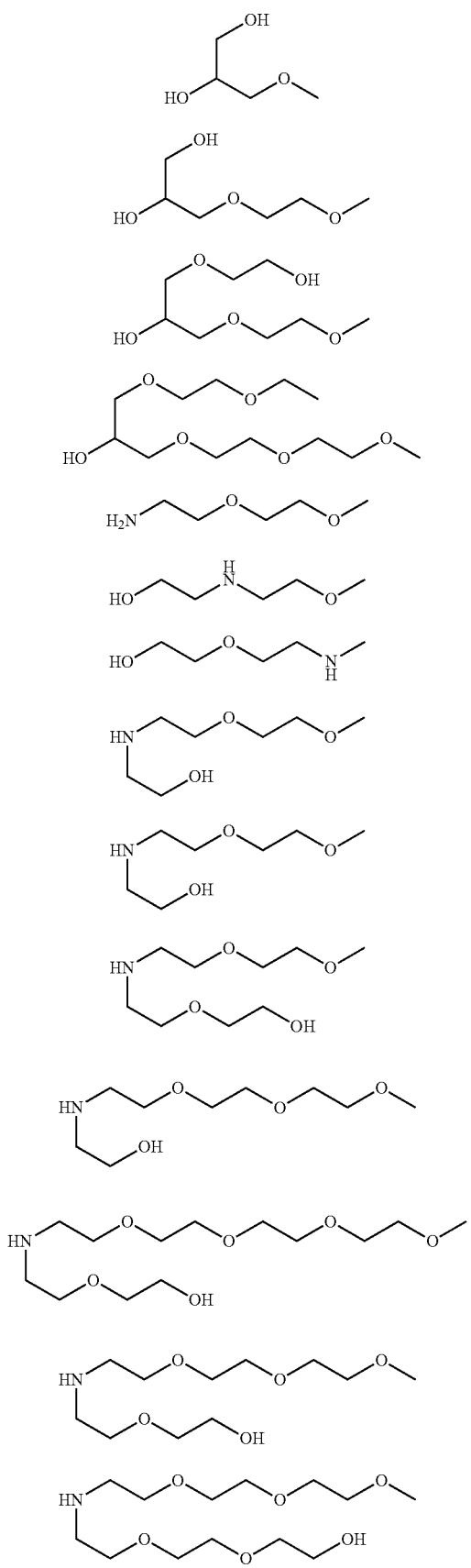

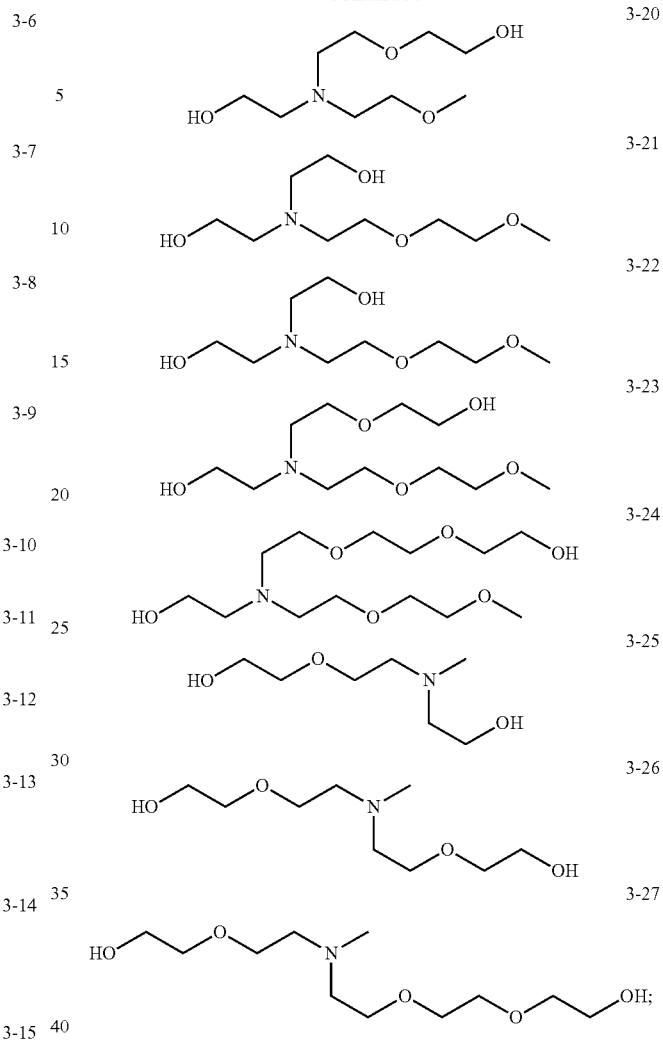

$Y^1$ represents a monovalent group comprising an anion;
$n^1$ represents 1 or 2, $n^2$ represents 0 or 1, $n^3$ represents an integer of 0 or more, $n^4$ represents an integer of 1 or more, and $n^1+n^3 \geq 1$ is satisfied, when more than one $R^3$ is present, such $R^3$s may be the same as or different from each other, when more than one $R^4$ is present, such $R^4$s may be the same as or different from each other, when more than one $R^5$ is present, such $R^5$s may be the same as or different from each other, and when more than one $Y^1$ is present, such $Y^1$s may be the same as or different from each other;

$M^1$ represents a cation;

$Z^1$ represents an anion;

a represents an integer of 1 or more, and b represents an integer of 0 or more, provided that a and b are selected so that electric charge of the structure represented by Formula (1) becomes zero; and when more than one $M^1$ is present, such $M^1$s may be the same as or different from each other, and when more than one $Z^1$ is present, such $Z^1$s may be the same as or different from each other.

2. The polymer compound according to claim 1, wherein the group represented by $Y^1$ is a group selected from $-CO_2^-$, $-SO_2^-$, $-SO_3^-$, $-O^-$, $PO_3^{2-}$, and $-BR^a{}_3^-$, wherein $R^a$ represents a hydrogen atom or a monovalent organic group, and a plurality of $R^a$s may be the same as or different from each other and may be bonded to each other to form a ring.

3. The polymer compound according to claim 2, wherein the group represented by $Y^1$ is a group represented by $-CO_2^-$.

4. The polymer compound according to claim 1, wherein $M^1$ is a cation selected from $Li^+$, $Na^+$, $K^+$, $Rb^+$, $Cs^+$, and $(R^b)_4N^+$, wherein $R^b$ represents a hydrogen atom or a monovalent organic group, and a plurality of $R^b$s may be the same as or different from each other and may be bonded to each other to form a ring.

5. The polymer compound according to claim 1, wherein the group represented by $R^4$ is a divalent organic group having two or more oxygen atoms.

6. The polymer compound according to claim 1, wherein the groups represented by $Ar^1$, $Ar^2$, $Ar^3$, and $Ar^4$ are each a phenylene group optionally having substituent(s).

7. The polymer compound according to claim 1, wherein the group represented by $R^2$ is a $(1+n^1+n^4)$-valent group optionally having substituent(s), wherein the $(1+n^1+n^4)$-valent group optionally having substituent(s) is a remainder of a benzene ring optionally having substituent(s) from which $(1+n^1+n^4)$ hydrogen atoms bonded to the benzene ring are removed.

8. The polymer compound according to claim 1, wherein q is 0.

9. The polymer compound according to claim 8, comprising a structure represented by Formula (3) as a constitutional unit:

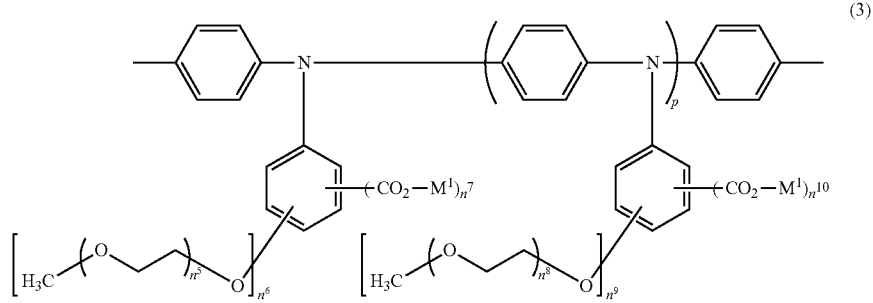

(3)

wherein:
p represents an integer of 0 or more;
$M^1$ represents a cation;
$n^5$ and $n^8$ each independently represent 1, 2, 3, or 4;
$n^6$, $n^7$, $n^9$, and $n^{10}$ each independently represent an integer of 1 to 4, and $n^6+n^7 \leq 5$ and $n^9+n^{10} \leq 5$ are satisfied.

10. The polymer compound according to claim 9, comprising a structure represented by Formula (4) as a constitutional unit:

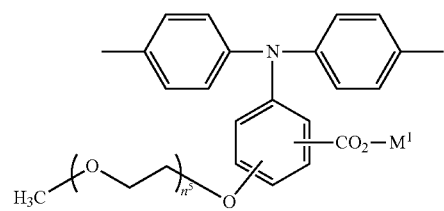

(4)

wherein $M^1$ represents a cation, and $n^5$ represents 1, 2, 3, or 4.

11. A composition comprising:
the polymer compound according to claim 1; and
at least one material selected from the group consisting of a hole transport material, an electron transport material, and a light-emitting material.

12. A stacked structure comprising the polymer compound according to claim 1.

13. The stacked structure according to claim 12, wherein the stacked structure is an electroluminescent device.

14. The stacked structure according to claim 12, wherein the stacked structure is a photoelectric conversion device.

15. A polymer compound comprising a structure represented by Formula (5) as a constitutional unit:

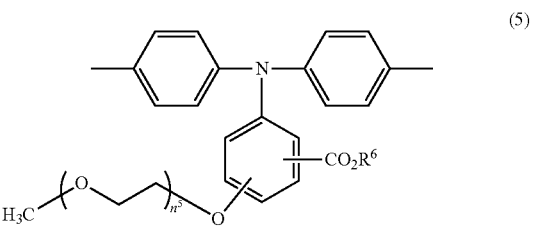

(5)

wherein $n^5$ represents an integer of 1 or more, and $R^6$ represents a monovalent organic group.

16. A compound represented by Formula (6):

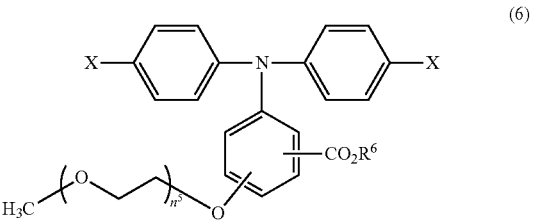

(6)

wherein:
$n^5$ represents an integer of 1 or more, and $R^6$ represents a monovalent organic group;
X represents a chlorine atom, a bromine atom, an iodine atom, a p-toluenesulfonate group, a trifluoromethanesulfonate group, a methanesulfonate group, a dihydroxyboryl group, or a dialkoxyboryl group, and the two X may be the same as or different from each other.

17. A compound represented by Formula (7):
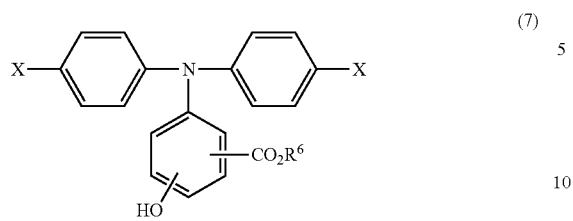
wherein:
R⁶ represents a monovalent organic group; and
X represents a chlorine atom, a bromine atom, an iodine atom, a p-toluenesulfonate group, a trifluoromethanesulfonate group, a methanesulfonate group, a dihydroxyboryl group, or a dialkoxyboryl group, and the two X may be the same as or different from each other.
* * * * *